US011052235B2

(12) United States Patent
Takeuchi

(10) Patent No.: US 11,052,235 B2
(45) Date of Patent: Jul. 6, 2021

(54) LEVER LOCK-TYPE MALE CONNECTOR AND MALE CONNECTOR ASSEMBLY

(71) Applicant: JMS CO., LTD., Hiroshima (JP)

(72) Inventor: Masahiko Takeuchi, Hiroshima (JP)

(73) Assignee: JMS Co., Ltd., Hiroshima (JP)

(*) Notice: Subject to any disclaimer, the term of this patent is extended or adjusted under 35 U.S.C. 154(b) by 396 days.

(21) Appl. No.: 15/571,695

(22) PCT Filed: May 11, 2016

(86) PCT No.: PCT/JP2016/064022
§ 371 (c)(1),
(2) Date: Nov. 3, 2017

(87) PCT Pub. No.: WO2016/185972
PCT Pub. Date: Nov. 24, 2016

(65) Prior Publication Data
US 2018/0133451 A1 May 17, 2018

(30) Foreign Application Priority Data
May 18, 2015 (JP) .............................. JP2015-100945

(51) Int. Cl.
*F16L 37/133* (2006.01)
*A61M 39/10* (2006.01)

(52) U.S. Cl.
CPC ........ *A61M 39/1011* (2013.01); *F16L 37/133* (2013.01); *A61M 2039/1016* (2013.01);
(Continued)

(58) Field of Classification Search
CPC ... F16L 37/0847; F16L 37/096; F16L 37/098; F16L 37/0985; F16L 37/0987;
(Continued)

(56) References Cited

U.S. PATENT DOCUMENTS 2,444,451 A * 7/1948 Kelso ................... F16L 37/127
251/149.9
5,137,524 A * 8/1992 Lynn ..................... A61M 39/04
604/414

(Continued)

FOREIGN PATENT DOCUMENTS

| JP | 7-148271 | 6/1995 |
|----|----------|--------|
| JP | 2004-000483 | 1/2004 |
| JP | 20012-075495 | 4/2012 |
| WO | 2013/154049 | 10/2013 |

*Primary Examiner* — Aaron M Dunwoody
(74) *Attorney, Agent, or Firm* — Hamre, Schumann, Mueller & Larson, P.C.

(57) ABSTRACT

Levers (30) are connected to a base end portion (13) of a male luer via a base (15). Each lever includes a locking portion (31) and an operating portion (35). A locking claw (32) protrudes from each locking portion toward the male luer. A lock ring (8) is provided opposing inner surfaces of the operating portions. The lock ring is movable between a first position at which the lock ring is located close to the base and a second position at which the lock ring is located away from the base. When the lock ring is at the first position, the levers are pivotable such that the locking claws move away from the male luer. When the lock ring is at the second position, the lock ring restricts the levers from pivoting such that the locking claws move away from the male luer.

16 Claims, 47 Drawing Sheets

(52) U.S. Cl.
CPC ............... *A61M 2039/1027* (2013.01); *A61M 2039/1038* (2013.01); *A61M 2039/1066* (2013.01); *A61M 2039/1072* (2013.01)

(58) Field of Classification Search
CPC ....... F16L 37/12; F16L 37/127; F16L 37/138; F16L 37/148; F16L 2201/10; A61M 2039/1016; A61M 2039/1027; A61M 2039/1038; A61M 2039/1066; A61M 39/1011
USPC .............................................. 285/81, 82, 89
See application file for complete search history.

(56) References Cited

U.S. PATENT DOCUMENTS

| | | | | |
|---|---|---|---|---|
| 5,330,235 | A | * | 7/1994 | Wagner ............... F16L 37/0985 285/320 |
| 5,437,650 | A | | 8/1995 | Larkin et al. |
| 2005/0253390 | A1 | * | 11/2005 | Blazek ............... A61M 39/1011 285/420 |
| 2006/0103133 | A1 | * | 5/2006 | Moretti ............... F16L 37/0987 285/305 |
| 2013/0181437 | A1 | * | 7/2013 | Semmel ............... F16L 37/0847 285/88 |
| 2014/0021714 | A1 | * | 1/2014 | Ueda .................. A61M 39/1011 285/81 |
| 2014/0035281 | A1 | * | 2/2014 | Nguyen ............... E21B 17/085 285/314 |
| 2015/0105753 | A1 | | 4/2015 | Okiyama |

\* cited by examiner

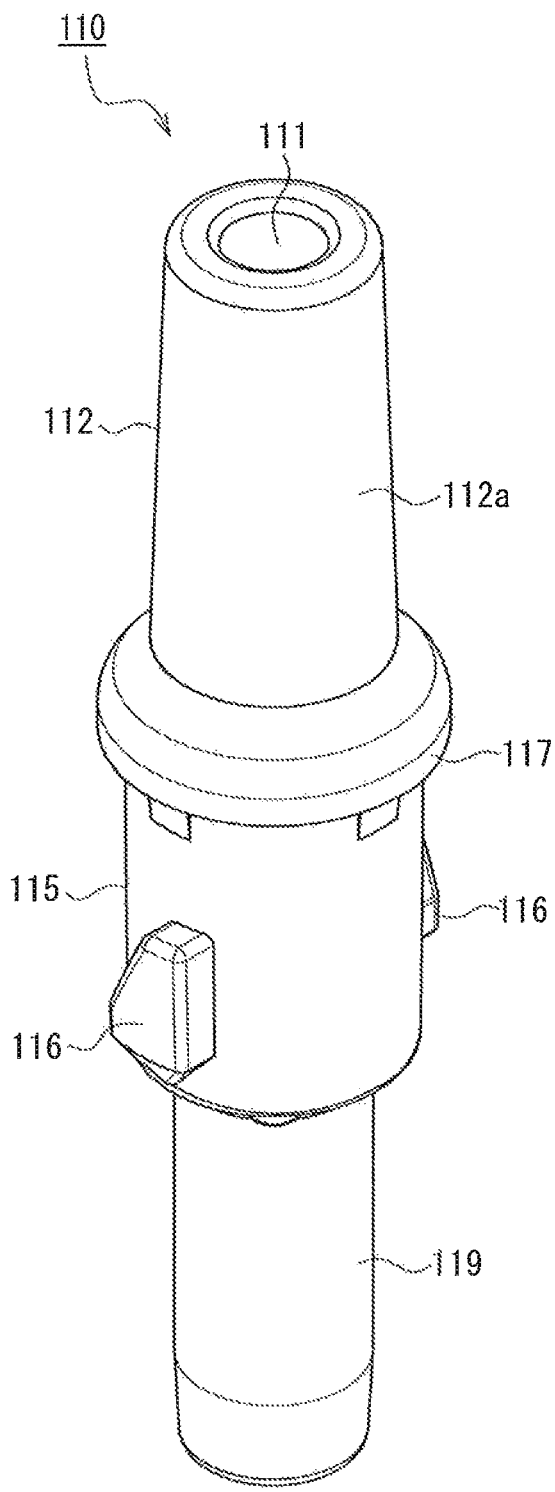
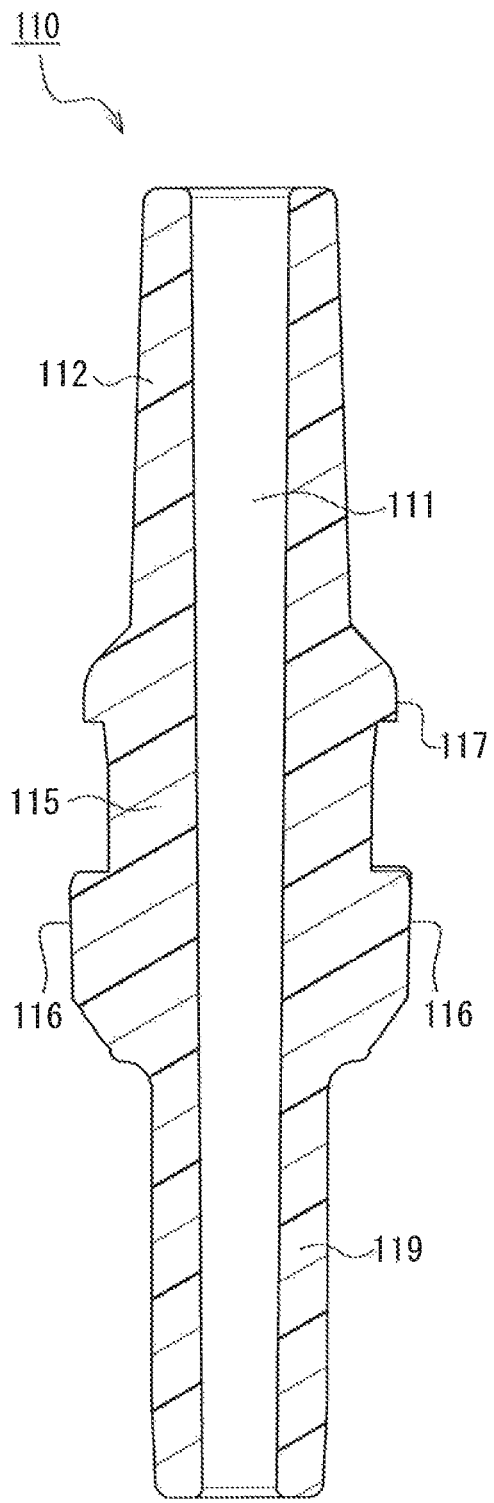
FIG. 6A
FIG. 6B

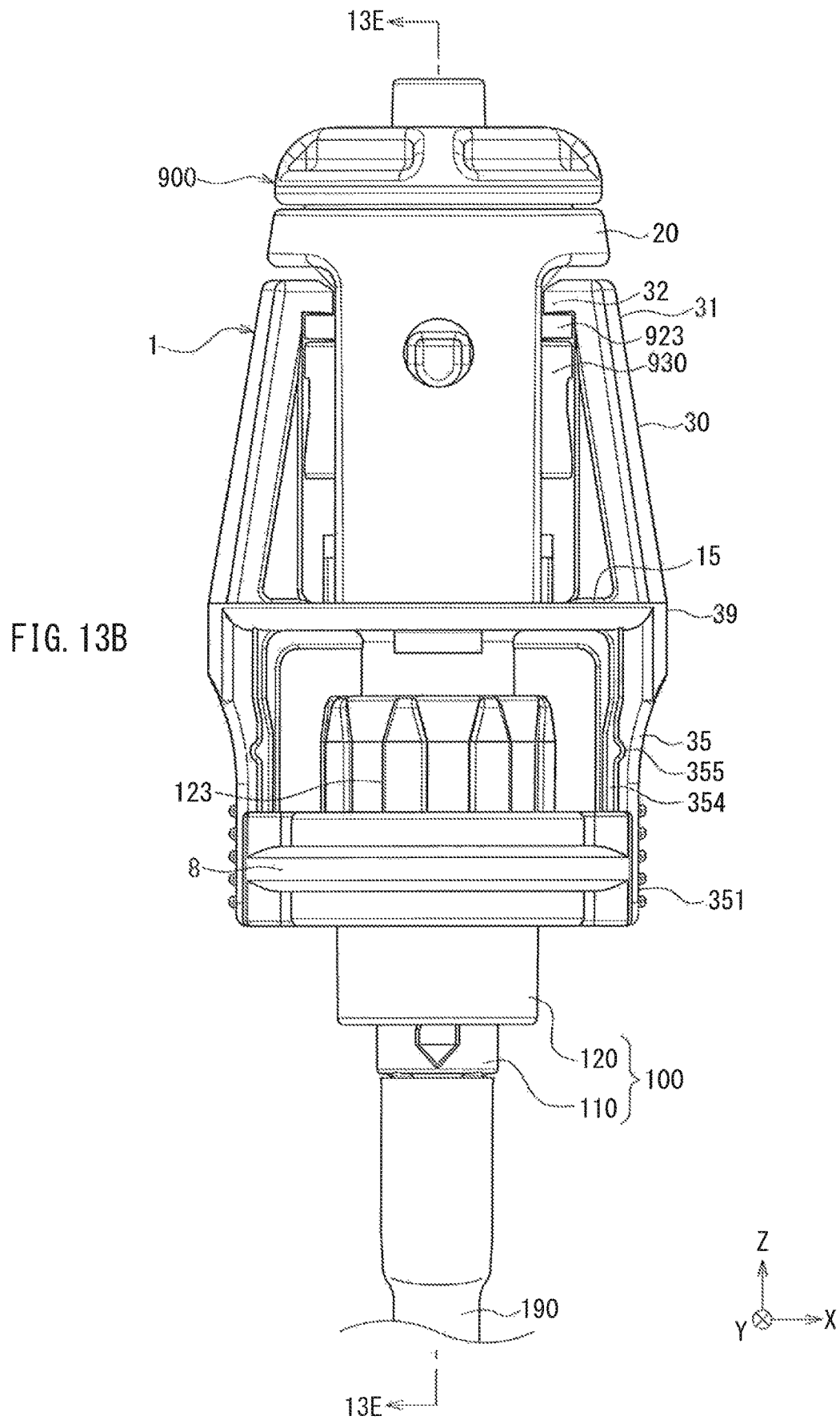

LEVER LOCK-TYPE MALE CONNECTOR AND MALE CONNECTOR ASSEMBLY

TECHNICAL FIELD

The present invention relates to a male connector including a lever-type lock mechanism for maintaining a state in which the male connector is connected to a female connector. The present invention also relates to a male connector assembly including the male connector.

BACKGROUND ART

In the field of medicine, circuits (lines) are used to convey various liquids such as medicinal solutions, infusion solutions, and blood. Such circuits are generally formed by connecting containers, various instruments, tubes, and the like. In order to connect different members, a connecting device constituted by a male connector and a female connector is used.

Many connecting devices for medical use are provided with a lock mechanism for locking a connected state in which the male connector and the female connector are connected to each other so as to prevent unintentional disconnection of the male connector and the female connector during treatment.

Patent Document 1 discloses a screw lock mechanism using a screw. The male connector includes a male luer on which a male tapered surface that becomes gradually narrower at one end is formed, and a lock nut that is rotatable around the male luer. A female thread is formed in the lock nut. The female connector includes a female tapered surface that can be fitted to the male tapered surface of the male luer and a male thread that can be screwed into the female thread of the lock nut. In a state in which the male luer is inserted into the female connector, the female thread of the lock nut is screwed onto the male thread of the female connector (locked state).

A screw lock mechanism has a problem in that it is difficult for a user to accurately know the screwed state of the male thread and the female thread. Thus, if the male thread and the female thread are excessively strongly screwed together, problematic situations, such as the threads breaking and the screwed connection becoming difficult to release, may occur. Conversely, if the male thread and the female thread are loosely screwed together, problematic situations, such as loosening of the screwed connection between the male thread and the female thread as well as the resulting leakage of a liquid through a gap between the male tapered surface and the female tapered surface, disconnection of the male connector and the female connector, and the like, may occur.

Patent Document 2 discloses a lever-type lock mechanism serving as a lock mechanism that addresses the above-described problem with screw lock mechanisms, the lever-type lock mechanism including elastically pivotable levers. The male connector includes a pair of levers such that the male luer is disposed therebetween. The levers are each held in a seesaw manner. A claw is formed at a leading end of each lever. The male luer is inserted into the female connector, and the claws are engaged with the female connector (locked state). In order to disconnect the male connector and the female connector from each other, the levers are caused to pivot by pressing the portions (operating portions) of the levers that are located on the opposite side to the claws. Thus, the claws are disengaged from the female connector.

With a lever-type lock mechanism, the male connector and the female connector can be easily connected and disconnected to and from each other, and therefore, the ease of operation is favorable. Moreover, switching between the locked state and a non-locked state depends on whether or not the claws of the levers are engaged with the female connector, and therefore, the connected state is highly stable and reliable.

CITATION LIST

Patent Documents

Patent Document 1: JP 117-14827A
Patent Document 2: JP 2004-483A

DISCLOSURE OF INVENTION

Problem to be Solved by the Invention

In a conventional lever-type lock mechanism, if an external force is applied to the operating portions of the levers, engagement of the claws with the female connector can be easily released. For this reason, there is a problem in that if an external force acts on the operating portions when, for example, the male connector collides with an object therearound or is pinned under a patient's body, the claws are unintentionally disengaged from the female connector.

The present invention was made to address the above-described problem with conventional lever-type lock mechanisms, and it is an object thereof to reduce the likelihood of a locked state being unintentionally cancelled, while maintaining favorable ease of operation with regard to connection and disconnection.

Means for Solving Problem

A lever lock-type male connector of the present invention includes a connector main body and a lock ring. The connector main body includes a rod-shaped male luer and a lever that is connected to a base end portion of the male luer via a base. The lever includes a locking portion that is disposed on the same side as the male luer relative to the base such that the locking portion opposes the male luer in a first direction, an operating portion that is disposed on the opposite side to the male luer relative to the base, and a locking claw that protrudes toward the male luer from a surface of the locking portion that is located on a side facing the male luer. The lock ring is disposed opposing an inner surface of the operating portion in the first direction. The lock ring is movable between a first position at which the lock ring is located close to the base and a second position at which the lock ring is located away from the base. When the lock ring is at the first position, the lever is elastically pivotable such that the locking claw moves away from the male luer. When the lock ring is at the second position, the lock ring restricts the lever from pivoting such that the locking claw moves away from the male luer.

A male connector assembly of the present invention includes the above-described lever lock-type male connector of the present invention and a screw lock-type connector. The connector main body further includes a tubular portion on the opposite side to the male luer relative to the base, the tubular portion being in communication with the male luer. A female tapered surface is formed on an inner circumferential surface of the tubular portion, the female tapered surface having an internal diameter that increases as the distance to a leading end of the tubular portion decreases. A male thread is formed on an outer circumferential surface of the tubular portion. The screw lock-type connector includes a luer main body provided with a male tapered surface that can be fitted to the female tapered surface of the tubular portion and a lock nut that is rotatable around the luer main body. The lock nut is provided with a female thread that can be screwed onto the male thread of the tubular portion.

Effects of the Invention

The connector main body includes the lever that is held by the base in a seesaw manner. The lever includes the locking claw that is engageable with the female connector. When the lock ring is at the first position, the lever is elastically pivotable such that the locking claw moves away from the male luer. Therefore, as is the case with a male connector including a conventional lever-type lock mechanism, the male connector and the male connector assembly of the present invention, which have the connector main body, provide excellent ease of operations for connection and disconnection to and from the female connector.

When the lock ring is at the second position, the lock ring restricts the lever from pivoting such that the locking claw moves away from the male luer. Thus, the likelihood of a locked state being unintentionally cancelled due to an external force acting on the operating portion can be reduced by moving the lock ring to the second position.

BRIEF DESCRIPTION OF DRAWINGS

FIG. 6A is a perspective view of a luer main body according to Embodiment 1 of the present invention, and FIG. 6B is a cross-sectional view of the luer main body.

FIG. 13B is a front view of the male connector assembly in FIG. 13A.

DESCRIPTION OF THE INVENTION

Figure 1:
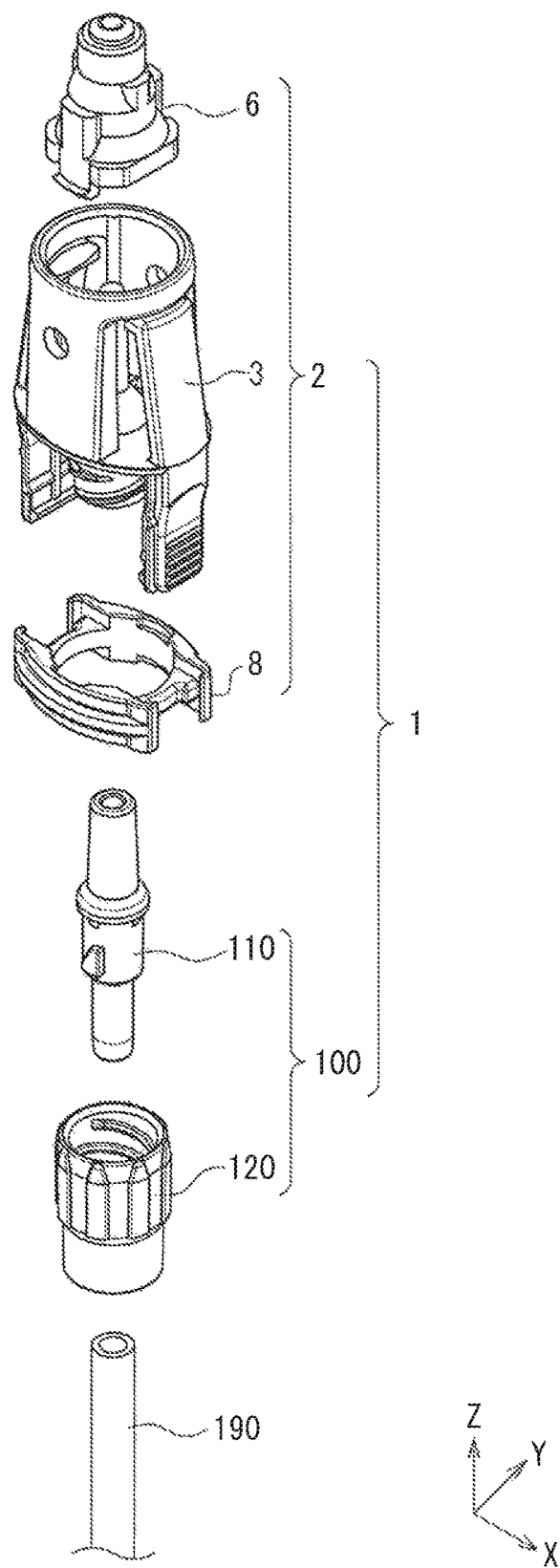
FIG. 1 is an exploded perspective view of a male connector assembly according to Embodiment 1 of the present invention.

In the above-described lever lock-type male connector of the present invention, it is preferable that when the lock ring is at the first position, the inner surface of the operating portion is spaced apart from the lock ring in the first direction. With this configuration, in a state in which the lock ring is at the first position, the lever can be easily pivoted such that the locking claw moves away from the male luer. This is advantageous in improving the ease of operations for connection and disconnection to and from the female connector.

The lock ring may be engageable with the operating portion in the first direction. This is advantageous in preventing the lock ring from falling from the connector main body.

A sliding rib may protrude from a side surface of the operating portion. The sliding rib may extend along a moving direction of the lock ring. In this case, the lock ring may include a claw that is engageable with the sliding rib. With this configuration, the lock ring can be engaged with the operating portion in the first direction using a simple structure.

The claw of the lock ring may include a sliding surface that opposes an outer surface of the sliding rib in the first direction. In this case, when the lock ring is at the first position, the sliding surface may abut against the outer surface of the sliding rib in the first direction. This is further advantageous in preventing the lock ring at the first position from falling from the connector main body. Also, this is advantageous in positioning the lock ring with respect to the first direction when the lock ring is at the first position.

The above-described male connector of the present invention may also be configured such that, in a state in which the lock ring is at the first position, if a female connector is moved toward the base along a longitudinal direction of the male luer, the locking claw collides with the female connector, and the lever pivots such that the locking claw moves away from the male luer, and if the female connector is moved further toward the base, the locking claw engages with the female connector, and the lever elastically recovers. In this case, according to one configuration example, in a state in which the lever has pivoted and the locking claw is not engaged with the female connector, the lock ring at the first position cannot be moved to the second position. With this configuration, the likelihood of performing an erroneous operation of starting to pass a liquid between the male connector and the female connector without being aware of the fact that the locking claw is not engaged with the female connector, and the occurrence of unintentional disconnection of the male connector and the female connector and leakage of the liquid can be reduced.

Alternatively, according to another configuration example, in a state in which the lever has pivoted and the locking claw is not engaged with the female connector, if the lock ring at the first position is moved toward the second position, the lock ring collides with the operating portion prior to reaching the second position, thereby causing the locking claw to be engaged with the female connector. With this configuration, insufficient engagement of the locking claw with the female connector is adjusted, and therefore, the likelihood of performing the above-described erroneous operation can be reduced.

The above-described male connector of the present invention may also be configured such that, in a state in which the lock ring is at the first position, if a female connector is moved toward the base along a longitudinal direction of the male luer, the lock ring is moved toward the second position by the female connector, and at the same time as the locking claw engages with the female connector, the lock ring reaches the second position. With this configuration, when the locking claw engages with the female connector, it is certain that the lock ring has reached the second position. Accordingly, the likelihood of performing an erroneous operation of forgetting to move the lock ring to the second position even though the locking claw has been engaged with the female connector can be reduced. This is advantageous in improving the safety because the likelihood of the state (locked state) in which the locking claw is engaged with the female connector being unintentionally cancelled due to an external force acting on the operating portion of the lever is reduced.

In the foregoing, the male connector may also be configured such that, in a state in which the locking claw is engaged with the female connector, the lock ring can be moved from the second position to the first position. The engagement of the locking claw with the female connector becomes cancellable as a result of moving the lock ring to the first position.

In the above-described male connector of the present invention, the lock ring may include a rod that extends beyond the base toward the male luer. In this case, the rod may be configured such that at least a portion thereof that is located on the male luer side relative to the base collides with a female connector. With this configuration, in the process of connecting the female connector to the male connector, the female connector collides with the at least a portion of the rod. After that, if the female connector is moved toward the base, the lock ring can be moved, via the female connector, from the first position toward the second position. Accordingly, the above-described configuration makes it possible to move the lock ring from the first position to the second position without touching the lock ring with a hand, and this is advantageous in performing the operation for connecting the female connector to the male connector in a simple and quick manner.

The connector main body may include a hood that surrounds the male luer. In this case, the at least a portion of the rod is disposed so as to protrude toward the male luer from an opening of a leading end of the hood when viewed along the longitudinal direction of the male luer. With this configuration, when the female connector is inserted into the hood, the female connector can reliably collide with the at least a portion of the rod. When the female connector is inserted further into the hood, the lock ring can be moved, via the female connector, from the first position toward the second position.

An inclined surface may be provided at an upper surface of the at least a portion of the rod, the inclined surface being inclined such that the distance to the base decreases as the distance to the male luer decreases. This configuration is advantageous in enabling, using a simple configuration, the lock ring to move from the second position toward the first position in a state in which the locking claw is engaged with the female connector.

The above-described male connector of the present invention may also be configured such that, in a state in which the lock ring is at the second position and the locking claw is engaged with the female connector, if a force acting toward the first position is applied to the lock ring, the rod deforms such that the at least a portion of the rod moves away from the male luer. This configuration is advantageous in enabling the lock ring to move from the second position to the first position in a state in which the locking claw is engaged with the female connector. After the lock ring has been moved to the first position, if the locking claw is disengaged from the female connector, the female connector can be disconnected from the male connector. After the disconnection, the deformed rod returns to its initial state.

The above-described male connector of the present invention may further include a first movement prevention mechanism that prevents the lock ring at the first position from moving toward the second position or a second movement prevention mechanism that prevents the lock ring at the second position from moving toward the first position. Furthermore, the male connector of the present invention may include both the first movement prevention mechanism and the second movement prevention mechanism. With the first movement prevention mechanism, deterioration of the ease of operations for connecting and disconnecting the male connector and the female connector due to unintentional movement of the lock ring at the first position toward the second position can be prevented. With the second movement prevention mechanism, unintentional disengagement of the locking claw of the lever and the female connector due to the lock ring at the second position moving toward the first position can be prevented.

A flow channel through which a liquid flows may be provided in the male luer. An opening that is in communication with the flow channel may be provided in an outer circumferential surface of the male luer. The male connector may further include a shield that closes the opening. In this case, it is preferable that when the male luer is inserted into a female connector, the shield is compressively deformed in a longitudinal direction of the male luer, and the opening is exposed. With this configuration, when the male connector or the male connector assembly is not connected to the female connector, leakage of the liquid to the outside from the opening can be prevented. Therefore, even if the locked state that is maintained by the lever-type lock mechanism is cancelled for some reason, and the male luer is unintentionally removed from the female connector, leakage of the liquid can be prevented.

The connector main body may include two of the levers. In this case, it is preferable that the two levers are disposed at symmetrical positions with respect to a central axis passing through the male luer. With this preferred configuration, the female connector can be stably held by the two locking claws, and thus, the locked state can be stably maintained.

In the above-described male connector of the present invention, it is preferable that, when the male connector is viewed along the central axis passing through the male luer, the male connector has a major axis in the first direction (direction in which the male luer opposes the lever). With this configuration, if the male connector or the male connector assembly is pinned under a patient with the central axis extending in the horizontal direction, the male connector or the male connector assembly can easily rotate so that the direction of the major axis becomes the horizontal direction. Therefore, the likelihood of the patient feeling pain or even developing a decubitus ulcer as a result of the skin or soft tissue of the patient being continuously pressed is reduced. Moreover, the likelihood of the weight of the patient acting on the operating portion is reduced, and thus, the likelihood of the state (locked state) in which the locking claw of the lever is engaged with the female connector being unintentionally cancelled in the case where an operator forgets to move the lock ring to the second position is reduced.

In the present invention, the "major axis" means an axis extending along a direction in which the external dimension is largest. Therefore, a male connector "having a major axis in the first direction" when viewed along the central axis (i.e., in plan view) means that the external dimension of the male connector when viewed along the central axis is largest in the first direction (i.e., the direction in which the male luer opposes the lever). The "external dimension" is defined by the distance between two points at which a straight line that is orthogonal to the central axis intersects an outline (projected shape along the central axis) that defines the external shape of the male connector when viewed along the central axis.

In the present invention, as long as the male connector when viewed along the central axis has the major axis in the first direction, the outline shape (i.e., projected shape along the central axis) of the male connector when viewed along the central axis can be any shape. Preferably, the outline shape is symmetrical with respect to the major axis. Also, preferably, a minor axis of the outline shape intersects the major axis at right angles on the central axis. The "minor axis" as used herein means an axis extending along a direction in which the external dimension is smallest. Preferably, the outline shape has only one major axis. Also, preferably, the outline shape has only one minor axis. Therefore, shapes (e.g., regular polygonal shapes such as squares) having two or more major axes and circles having a constant external dimension in any direction around the central axis are not preferred as the outline shapes of the male connector of the present invention. Even when an outline shape has a protrusion or a recess, if the protrusion or the recess is minute in comparison with the overall outline shape, and it is judged that the protrusion or the recess has substantially no effect on the rotation of the male connector or the male connector assembly when pinned under the patient, the major axis, the minor axis, and the outline shape can be defined in disregard of such protrusion or recess.

With regard to the male connector of the present invention, it is preferable that the male connector has a substantially elliptical outline when viewed along the central axis. With this preferred configuration, if the male connector or the male connector assembly is pinned under the patient with the central axis extending in the horizontal direction, the male connector or the male connector assembly can more easily rotate so that the direction of the major axis of the substantially elliptical shape becomes the horizontal direction. Therefore, the likelihood of the patient feeling pain or developing a decubitus ulcer is further reduced. Moreover, when the operator forgets to move the lock ring to the second position, the likelihood of the state (locked state) in which the locking claw of the lever is engaged with the female connector being unintentionally cancelled is further reduced.

The above-described substantially elliptical outline of the male connector may be constituted only by the connector main body or may be constituted by the connector main body and the lock ring.

In the case where the substantially elliptical outline of the male connector is constituted by the connector main body alone, it is preferable that, when viewed along the central axis, the lock ring does not protrude from the substantially elliptical outline of the connector main body. As long as the lock ring does not protrude from the substantially elliptical outline of the connector main body, the lock ring when viewed along the central axis may have any external shape.

On the other hand, employing a configuration in which the substantially elliptical outline of the male connector is formed by combining the connector main body and the lock ring is advantageous in improving the degree of freedom of design of the connector main body and the lock ring.

A leading end of the hood may have a circular shape that is coaxial with the central axis passing through the male luer. In this case, it is preferable that an external diameter of the hood at the leading end is equal to or smaller than a minor diameter of the substantially elliptical shape along the minor axis. With this preferred configuration, the size of a portion that is located above (on the hood side of) the base can be reduced.

It is preferable that the operating portion of the lever is located nearer to the central axis than a portion of the lever that is connected to the base. With this preferred configuration, when the male connector collides with a neighboring device or the male connector is pinned under the patient's body, the likelihood of an unintentional external force acting on the operating portion is low. For this reason, when the operator forgets to move the lock ring to the second position, the likelihood of the state (locked state) in which the locking claw of the lever is engaged with the female connector being unintentionally cancelled is further reduced.

A portion of the connector main body that protrudes furthest from the central axis in the radial direction may be a portion (lever base portion) of the lever that is connected to the base. With this preferred configuration, an unintentional external force is more likely to be applied to the lever base portion, and less likely to be applied to the operating portion. Thus, when the operator forgets to move the lock ring to the second position, the likelihood of the state (locked state) in which the locking claw of the lever is engaged with the female connector being unintentionally cancelled is further reduced.

In the above-described male connector assembly of the present invention, a configuration may also be adopted in which, in a state in which the male tapered surface of the luer main body has been fitted to the female tapered surface of the tubular portion, and the female thread of the lock nut has been screwed onto the male thread of the tubular portion, if the lock ring is moved to the second position, the lock nut is disposed within the lock ring. With this configuration, it is difficult to touch the lock nut. Therefore, the likelihood of the occurrence of an unforeseen situation in which, for example, the patient erroneously rotates the lock nut and loosens the screwed connection between the female thread of the lock nut and the male thread of the tubular portion is reduced.

Hereinafter, the present invention will be described in detail while showing preferred embodiments thereof. However, it goes without saying that the present invention is not limited to the embodiments below. In the drawings that will be referred to in the following description, only the main members of constituent members of the embodiments of the present invention are shown in a simplified manner for the sake of convenience of description. Accordingly, the present invention may include optional members that are not shown in the drawings below. Moreover, it should be understood that the members shown in the drawings below may be changed or omitted within the scope of the present invention. In the drawings that will be referred to in the description of the embodiments below, members corresponding to those members shown in the drawings that are referred to in the description of any preceding embodiment are denoted by the same reference numerals as the members shown in the drawings of that preceding embodiment. With respect to such members, redundant descriptions are omitted, and the description of the preceding embodiment should be taken into account.

Embodiment 1

FIG. 1 is an exploded perspective view of a male connector assembly 1 according to Embodiment 1 of the present invention. The male connector assembly 1 includes a lever lock-type male connector (hereinafter simply referred to as "male connector") 2 and a screw lock-type connector 100. The male connector 2 includes a connector main body 3, a shield 6, and a lock ring 8. The screw lock-type connector 100 includes a luer main body 110 and a lock nut 120. A flexible tube 190 is connected to the male connector 2 via the screw lock-type connector 100.

Hereinafter, the various portions will be sequentially described.

1. Male Connector 1. 1. Connector Main Body

Figure 2A:
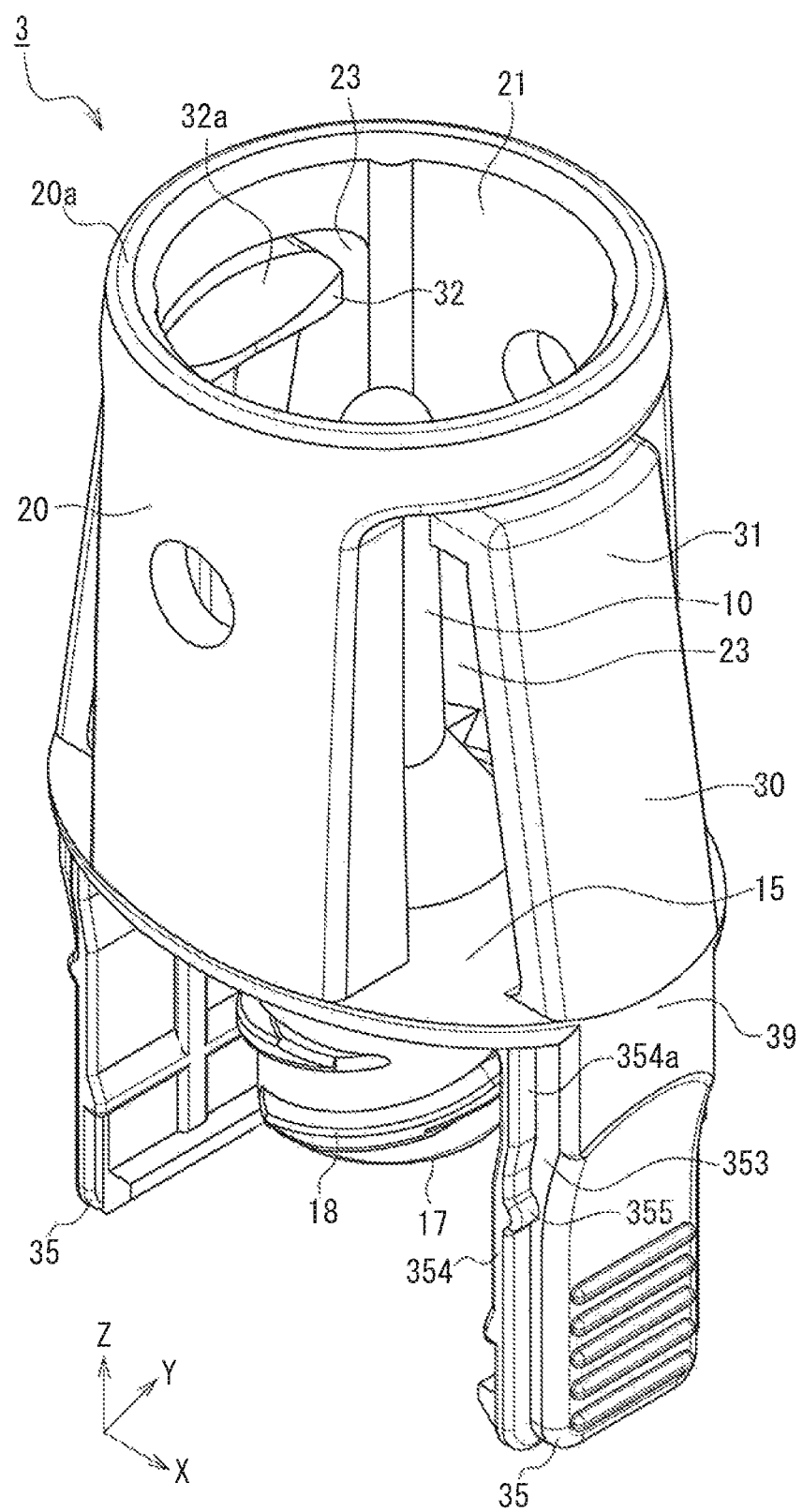
FIG. 2A is a perspective view of a connector main body according to Embodiment 1 of the present invention when viewed from above.
Figure 2B:
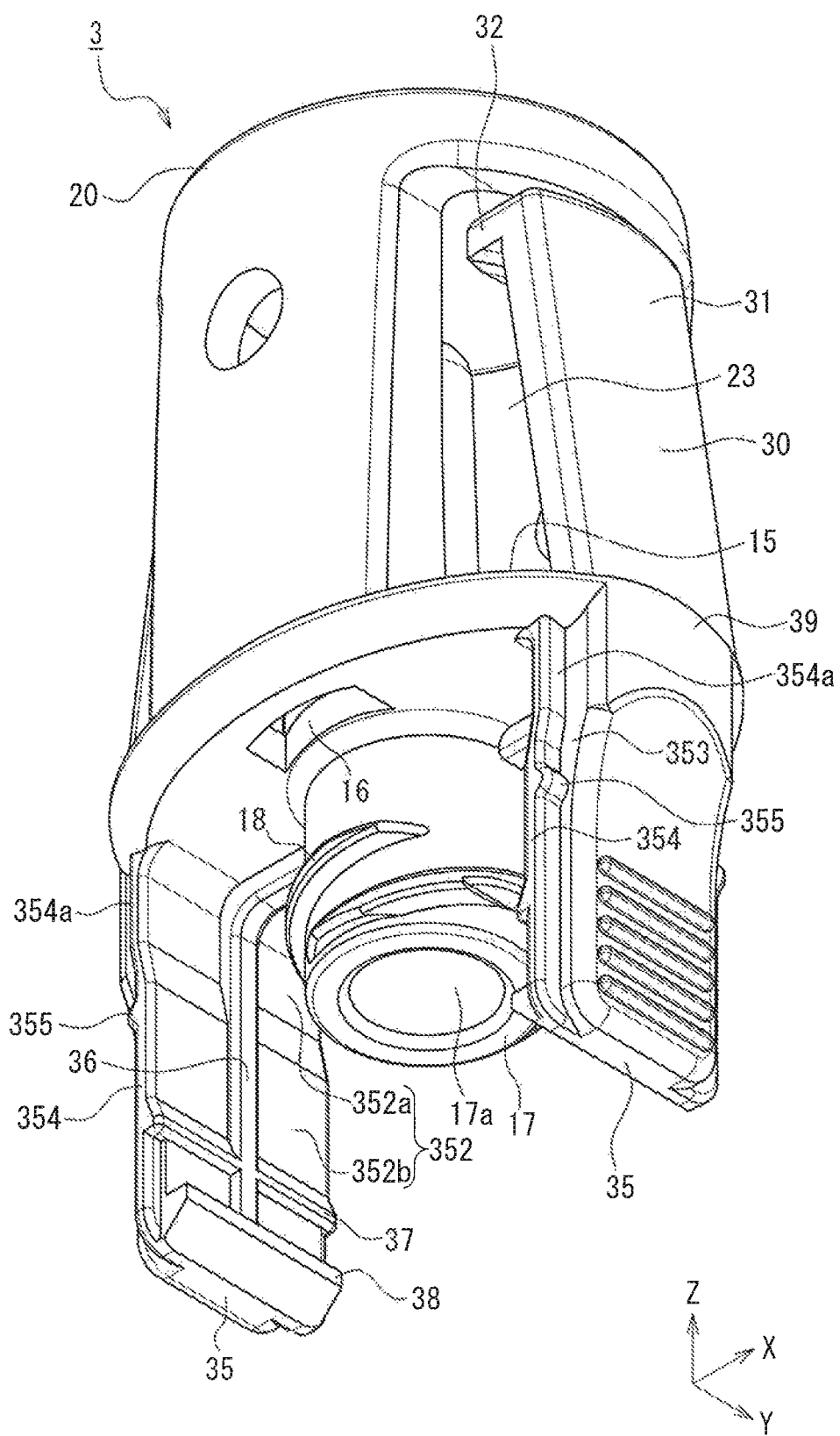
FIG. 2B is a perspective view of the connector main body according to Embodiment 1 of the present invention when viewed from below.
Figure 2C:
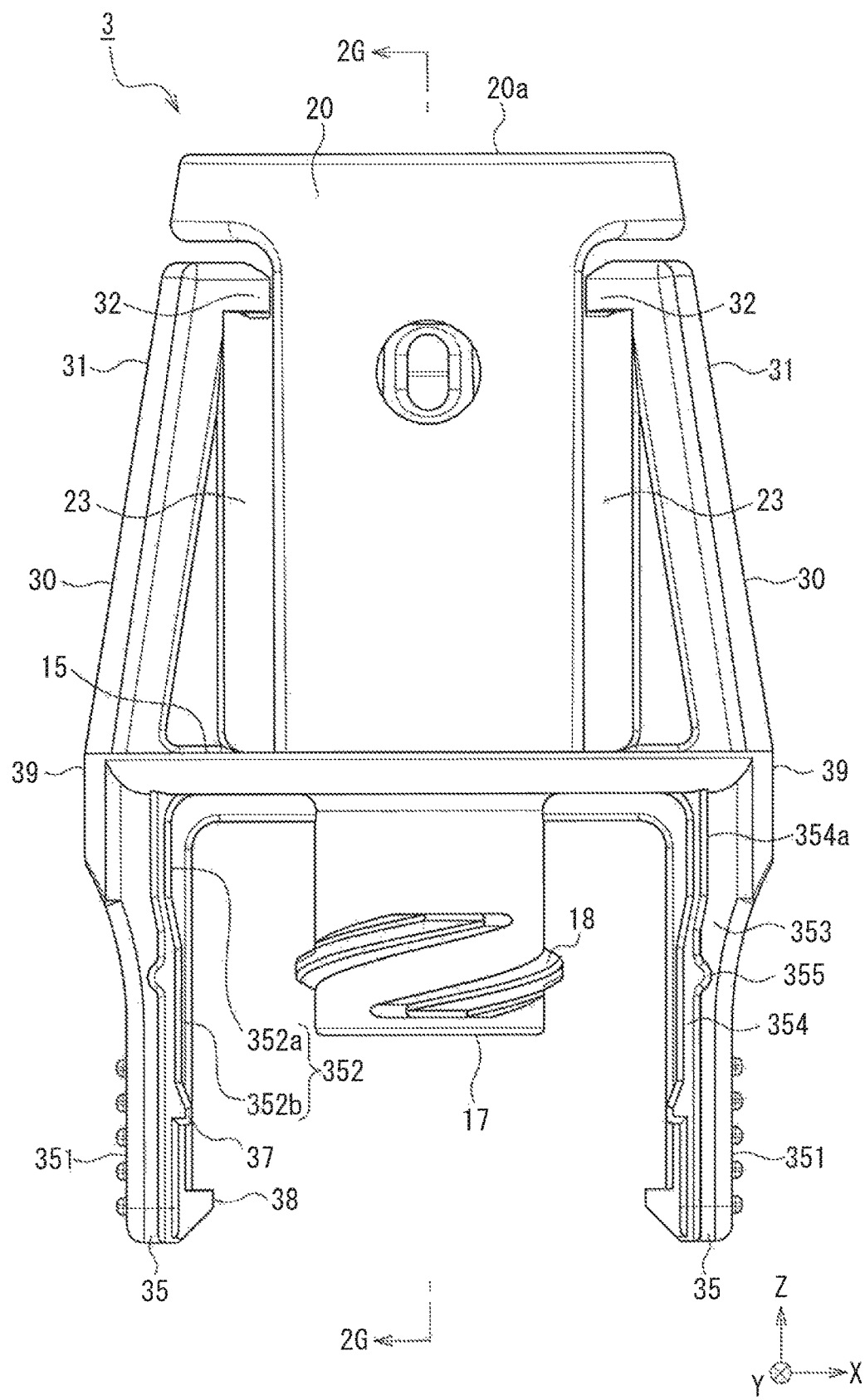
FIG. 2C is a front view of the connector main body according to Embodiment 1 of the present invention.
Figure 2D:
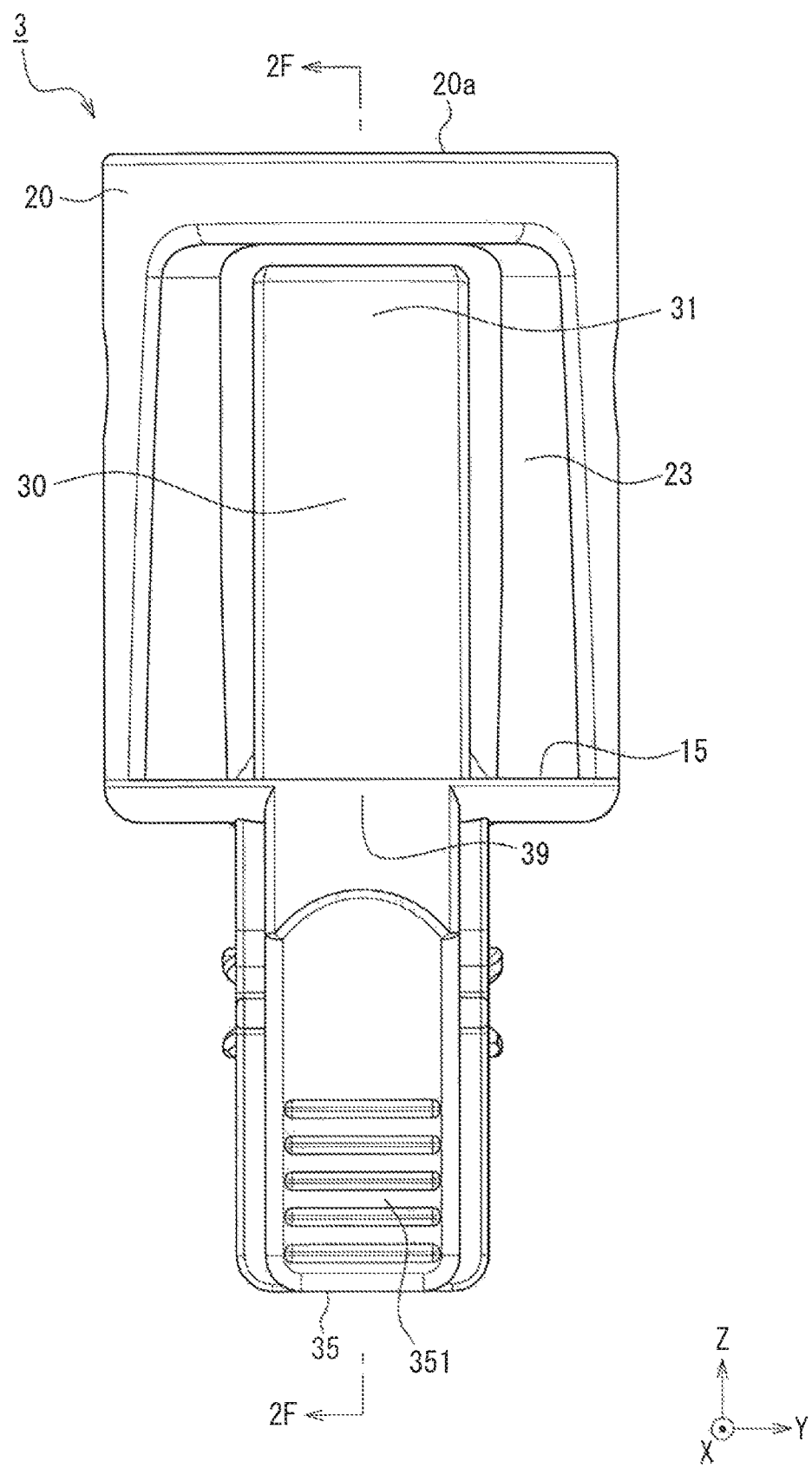
FIG. 2D is a side view of the connector main body according to Embodiment 1 of the present invention.
Figure 2E:
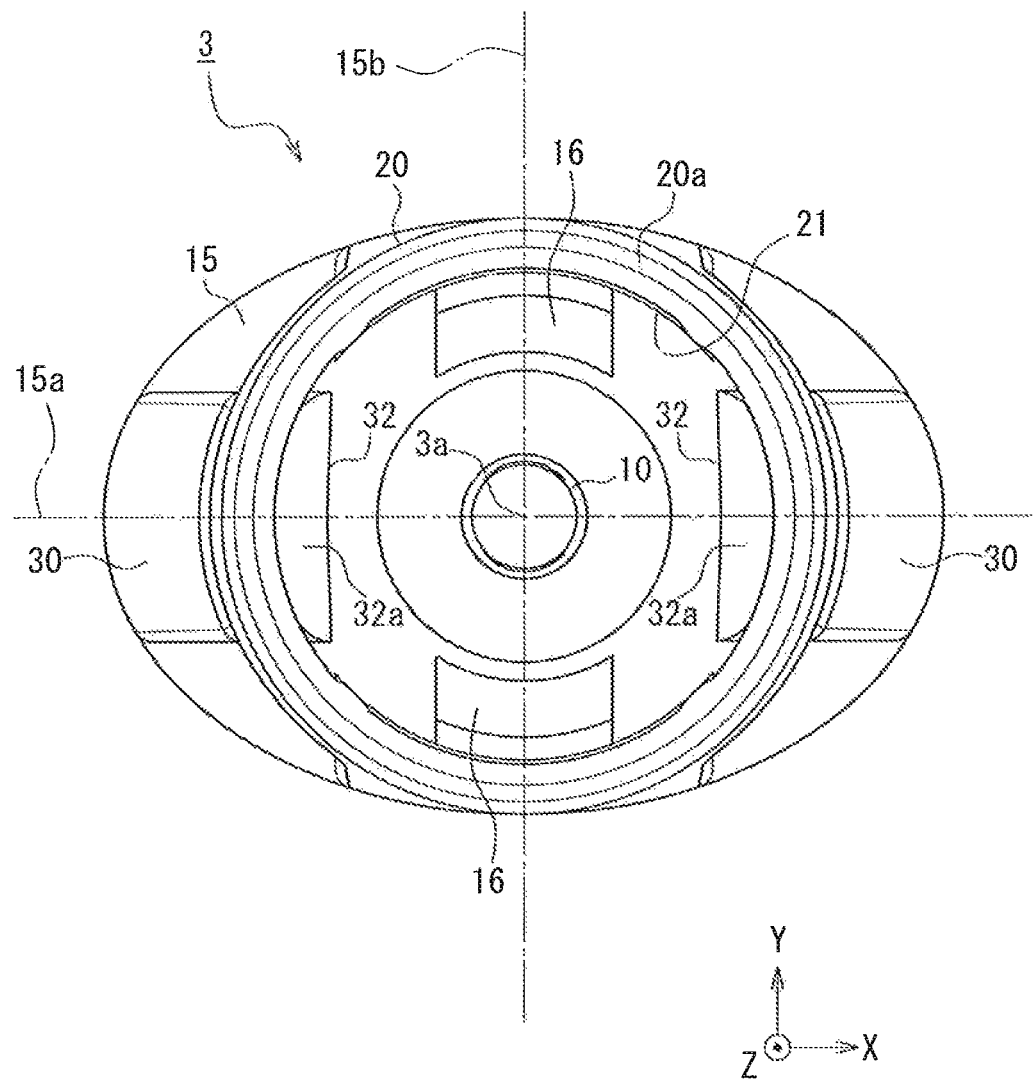
FIG. 2E is a plan view of the connector main body according to Embodiment 1 of the present invention.
Figure 2F:
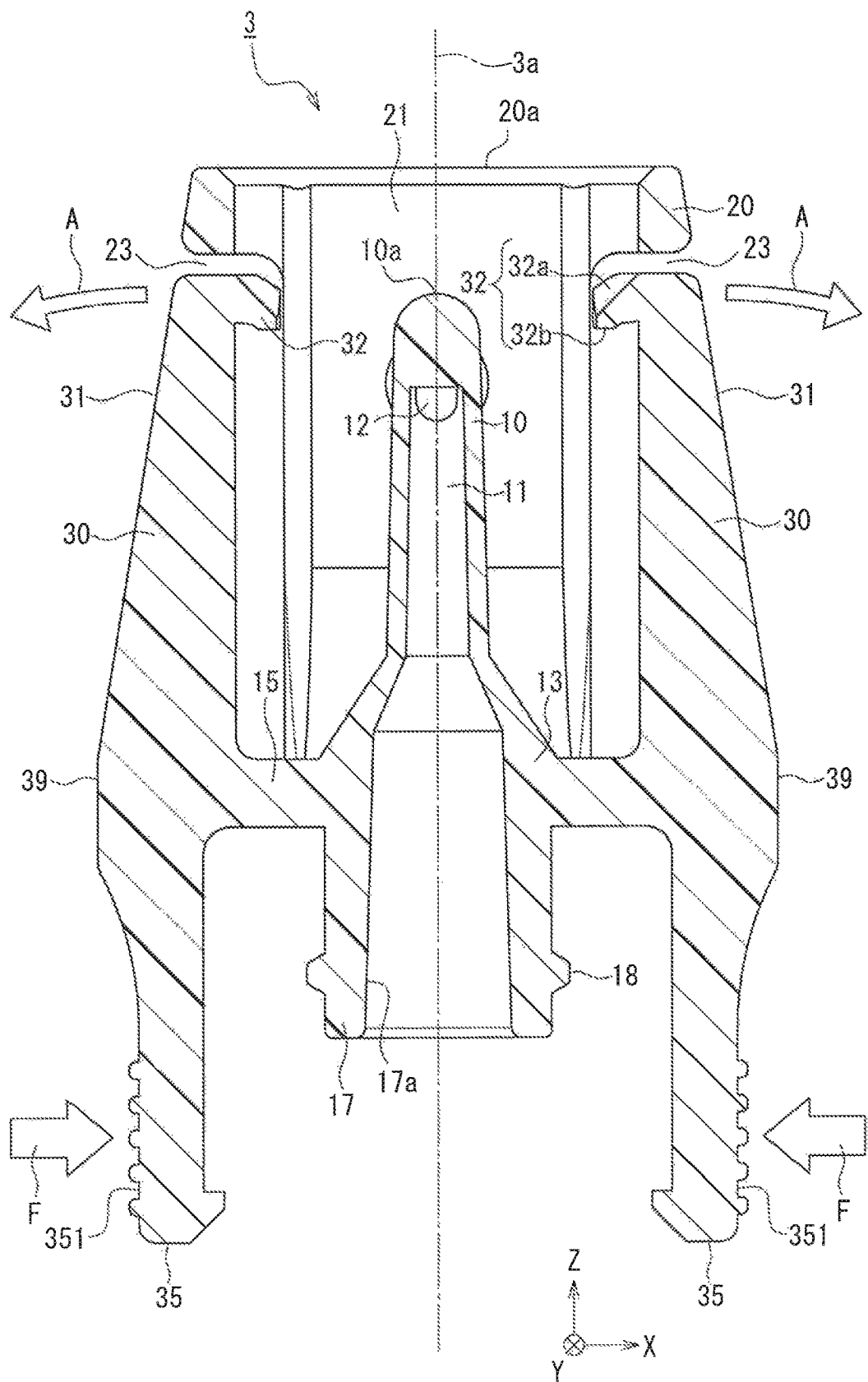
FIG. 2F is a cross-sectional view of the connector main body according to Embodiment 1 of the present invention taken along a vertical plane containing line 2F-2F in FIG. 2D.
Figure 2G:
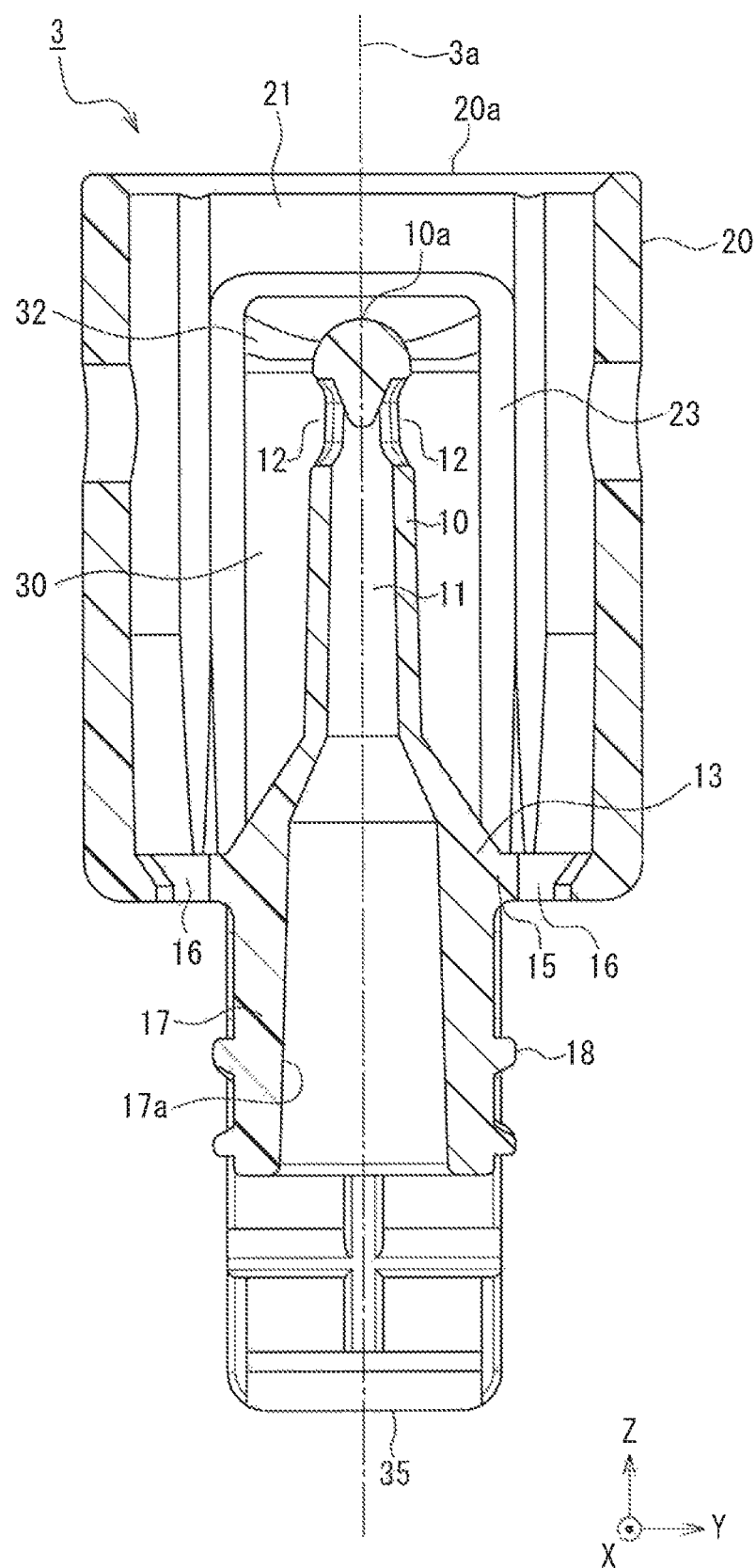
FIG. 2G is a cross-sectional view of the connector main body according to Embodiment 1 of the present invention taken along a vertical plane containing line 2G-2G in FIG. 2C.

The connector main body 3 constituting the male connector 2 will be described. FIG. 2A is a perspective view of the connector main body 3 when viewed from above, and FIG. 2B is a perspective view of the connector main body 3 when viewed from below. FIGS. 2C, 2D, and 2E are a front view, a side view, and a plan view, in that order, of the connector main body 3. FIG. 2F is a cross-sectional view of the connector main body 3 taken along a vertical plane containing line 2F-2F in FIG. 2D. FIG. 2G is a cross-sectional view of the connector main body 3 taken along a vertical plane containing line 2G-2G in FIG. 2C. In FIGS. 2F and 2G, a long dashed short dashed line 3a represents the central axis of the connector main body 3. The central axis 3a also serves as the central axis of all the members (see FIG. 1) that constitute the male connector assembly 1.

For the sake of convenience of the following description, an XYZ orthogonal coordinate system with an axis parallel to the central axis 3a being the Z-axis is set. A direction (Z-axis direction) that is parallel to the central axis 3a is referred to as "vertical direction", a direction that is parallel to a plane (XY plane) that is perpendicular to the central axis 3a is referred to as "horizontal direction", a direction that is orthogonal to the central axis 3a is referred to as "radial direction" or "diameter direction", and the direction of rotation about the central axis 3a is referred to as "circumferential direction". With respect to the radial direction, the side nearer the central axis 3a is referred to as "inner side", and the side further from the central axis 3a is referred to as "outer side". "Up" and "down" are defined based on FIGS. 1 and 2A. However, the "vertical direction" and the "horizontal direction" do not mean the actual orientation of the male connector 2 and the male connector assembly 1 during usage.

As shown in FIGS. 2F and 2G, the connector main body 3 includes a male luer 10 serving as a male member. The male luer 10 is a rod-shaped member extending along and coaxially with the central axis 3a. In Embodiment 1, an outer circumferential surface (side surface) of a portion of the male luer 10 that is near a leading end 10a and that is to be inserted into a female member (septum 910, which will be described later) constitutes a cylindrical surface whose external diameter is constant with respect to the direction of the central axis 3a, and an outer circumferential surface of a portion of the male luer 10 that is near a base end portion 13 constitutes a tapered surface (conical surface) whose external diameter decreases as the distance to the leading end 10a decreases. However, the shape of the outer circumferential surface of the male luer 10 is not limited to the above-described shape, and can be selected as desired. For example, the outer circumferential surface of the male luer 10 may constitute a cylindrical surface whose external diameter is constant from the base end portion 13 to the leading end 10a. Alternatively, the outer circumferential surface of the male luer 10 may constitute a smooth curved surface whose external diameter gradually decreases from the base end portion 13 toward the leading end 10a.

A flow channel 11 is formed along the central axis 3a within the male luer 10. The flow channel 11 is not open in the leading end 10a of the male luer 10. Two lateral holes 12 that are in communication with the flow channel 11 are formed in the outer circumferential surface of the male luer 10 at respective positions near the leading end 10a. Each lateral hole 12 penetrates the male luer 10 in the radial direction and is open in the outer circumferential surface of the male luer 10. It should be noted that the number of lateral holes 12 is not necessarily required to be two, and may also be one, or three or more.

A base 15 protrudes outward from the base end portion 13 of the male luer 10. The base 15 is a flat plate-shaped member that is parallel to the horizontal direction. As can be understood from FIG. 2E, when viewed along the central axis 3a, the base 15 has a substantially elliptical shape having a major axis 15a that is parallel to the X-axis and a minor axis 15b that is parallel to the Y-axis.

A tubular portion 17 protrudes downward from the base 15. The tubular portion 17 has a substantially cylindrical tubular shape that is coaxial with the central axis 3a, and a flow channel that is in communication with the flow channel 11 of the male luer 10 is formed in the tubular portion 17. An inner circumferential surface 17a of the tubular portion 17 constitutes a female tapered surface (e.g., a 6% tapered surface) whose internal diameter increases as the distance from the base 15 increases. A male thread 18 is formed on an outer circumferential surface of the tubular portion 17.

A hood 20 extends upright from an outer end edge of the base 15 toward the same side as the male luer 10. The hood 20 has a hollow tubular shape that surrounds the male luer 10. The hood 20 is open upward. A leading end (upper end) 20a of the hood 20 that surrounds an opening 21 has a circular shape that is coaxial with the central axis 3a. The leading end 20a of the hood 20 is located at a higher position than the leading end 10a of the male luer 10.

A pair of cut-outs 23 are provided in a side wall of the hood 20. The cut-outs 23 are holes (openings) penetrating the hood 20 in the radial direction. The pair of cut-outs 23 oppose each other in the X-axis direction with the male luer 10 disposed therebetween. Each cut-out 23 has an inverted "U"-shape (see FIG. 2D), and a lower end thereof reaches the base 15. However, the cut-outs 23 do not reach the leading end 20a of the hood 20.

As is best shown in FIG. 2F, a pair of levers 30 oppose each other in the X-axis direction (first direction) with the central axis 3a disposed therebetween. The levers 30 are rectangular strip-shaped members that extend substantially parallel to the central axis 3a. The longitudinal direction of the levers 30 extends along a vertical plane (XZ plane) containing the central axis 3a and the major axis 15a. The levers 30 are connected to the outer end edge of the base 15. Each lever 30 includes a locking portion 31 that is disposed on the same side (upper side) as the male luer 10 relative to the base 15 and an operating portion 35 that is disposed on the opposite side (lower side) to the male luer 10 relative to the base 15. A portion of each lever 30 which is located between the locking portion 31 and the operating portion 35 and to which the base 15 is connected is referred to as a lever base portion 39. The locking portions 31 each oppose the male luer 10 in the X-axis direction.

The locking portions 31 are disposed within the respective cut-outs 23 that are formed in the hood 20. In other words, the locking portions 31 are surrounded by the respective inverted "U"-shaped slits 23 that penetrate the hood 20 in the radial direction (see FIG. 2D).

A locking claw 32 protrudes toward the male luer 10 from a surface (inner surface) of each locking portion 31 that faces the male luer 10. Each locking claw 32 includes an inclined surface 32a and an engagement surface 32b. The inclined surface 32a is inclined such that the distance from the male luer 10 increases as the distance from the base 15 increases. The engagement surface 32b is a flat surface that is disposed nearer to the base 15 than the inclined surface 32a and that is substantially parallel to a horizontal plane (XY plane). As shown in FIG. 2E, when viewed from above, the top portion (portion that is nearest to the male luer 10) of each claw 32 protrudes toward the male luer 10 beyond the leading end 20a that surrounds the opening 21 of the hood 20.

As will be described later, when the male connector 2 is connected to a female connector, the locking claws 32 are engaged with the female connector (see FIG. 13D, which will be described later). The levers 30 function as a "lever-type lock mechanism" that maintains the state in which the male connector 2 and the female connector are connected to each other. Since the two levers 30 are disposed at respective positions that are symmetrical with respect to the central axis 3a (i.e., the male luer 10), the two locking claws 32 can be engaged with the female connector at respective positions that are symmetrical with respect to the central axis 3a. Accordingly, the female connector can be stably held, and thus, the reliability of the lever-type lock mechanism is improved. The state in which the locking claws 32 are engaged with the female connector is referred to as "locked state".

Each lever 30 has a mechanical strength that is high enough for the entire lever 30 from the upper end (locking portion 31) to the lower end (operating portion 35) to be regarded as a substantially rigid body. In contrast, the mechanical strength of the base 15 that joins the base end portion 13 of the male luer 10 to each lever 30 is relatively low. Therefore, when a force F acting toward the central axis 3a is applied to outer surfaces 351 of the operating portions 35 as shown in FIG. 2F, the base 15 can elastically deform and bend, thereby allowing the levers 30 to pivot (or swing) such that the locking portions 31 and the locking claws 32 formed on the respective locking portions 31 move away from the male luer 10 (in the directions of arrows A).

As shown in FIG. 2B, an inner surface (surface that faces the tubular portion 17) 352 of each operating portion 35 has two regions 352a and 352b that are located at different distances to the central axis 3a. The recessed region 352a that is disposed near the base 15 is relatively distanced from the central axis 3a, while the lock region 352b that is disposed below the recessed region 352a is relatively close to the central axis 3a. In a natural state (initial state) in which no external force is applied to the levers 30, the lock regions 352b are parallel to the YZ plane.

A rib 36 protruding toward the central axis 3a from the inner surface 352 of each operating portion 35 extends in the vertical direction from the base 15 to a lower end of the operating portion 35. The ribs 36 improve the strength of the operating portions 35. Furthermore, a locking projection (second locking projection) 37 and a stopping projection 38 that protrude toward the central axis 3a are provided on the lock region 352b of each inner surface 352. The stopping projections 38 are each located at or near the lower end of the respective operating portions 35. The locking projections 37 are located at positions that are slightly spaced upward from the respective stopping projections 38. The amount by which the stopping projections 38 protrude from the respective lock regions 352b is larger than that of the locking projections 37.

Sliding ribs 354 protrude in the Y-axis direction from respective side surfaces (surfaces parallel to the XZ plane) 353 of each operating portion 35. The sliding ribs 354 extend substantially in the vertical direction from the base 15 to the lower ends of the operating portions 35. A portion of an outer surface (surface that faces away from the tubular portion 17) of each sliding rib 354 that is located at the substantially same position as the recessed region 352a with respect to the vertical direction is shifted away from the central axis 3a compared with portions below this portion and constitutes a pressure contact portion 354a. A locking projection (first locking projection) 355 protruding outward from the outer surface of each sliding rib 354 is provided at a position below the pressure contact portion 354a.

As shown in FIGS. 2B and 2G, a pair of holes 16 penetrating the base 15 in the vertical direction are formed in the base 15. The holes 16 are disposed on the minor axis 15b (see FIG. 2E) of the base 15 having the substantially elliptical shape.

As shown in FIG. 2C, when viewed along a direction (Y-axis direction) that is orthogonal to the central axis 3a and the major axis 15a (in front view), the connector main body 3 has the largest horizontal dimension at the position of the base 15 (i.e., lever base portions 39). A portion of the connector main body 3 that is located above the base 15 has a tapered shape (or a trapezoidal shape) whose horizontal dimension gradually decreases as the distance from the base 15 increases in the upward direction. The locking portion 31 of each lever 30 and a portion of the hood 20 that is located above the locking portions 31 extend along a common straight line. On the other hand, the operating portion 35 of each lever 30 is located nearer to the tubular portion 17 (or the central axis 3a) than the lever base portion 39. In this manner, of the lever base portion 39, the locking portion 31, and the operating portion 35 of each lever 30, the lever base portion 39 protrudes furthest outward from the central axis 3a in the horizontal direction.

As shown in FIG. 2D, when viewed along a direction (X-axis direction) that is orthogonal to the central axis 3a and the minor axis 15b (in side view), the portion of the connector main body 3 that is located above the base 15 has a rectangular shape whose horizontal dimension is substantially constant from the base 15 to the leading end 20a of the hood 20. The horizontal dimension of the operating portion 35 of each lever 30 is smaller than the horizontal dimensions of the base 15 and the portion that is located above the base 15.

As shown in FIG. 2E, when viewed from above along the central axis 3a (in plan view), the external dimension of the connector main body 3 is largest in the direction (left-right direction in FIG. 2E) in which the male luer 10 opposes the levers 30, and is smallest in the direction (up-down direction in FIG. 2E) that is orthogonal to this direction. The outline (projected shape) of the connector main body 3 of Embodiment 1 has a substantially elliptical shape having the major axis 15a in the direction in which the external dimension is largest and the minor axis 15b in the direction in which the external dimension is smallest. The substantially elliptical shape is based on the shape of the connector main body 3 at the position of the base 15 (or the lever base portions 39). The major axis 15a and the minor axis 15b intersect at right angles on the central axis 3a. The leading end 20a of the hood 20 has a circular shape that is coaxial with the central axis 3a and is inscribed in the above-described substantially elliptical outline of the connector main body 3.

As shown in FIG. 2A, the shape of an outer circumferential surface of the portion of the connector main body 3 that is located above the base 15 is substantially a curved surface that smoothly connects the circular shape of the leading end 20a of the hood 20 and the substantially elliptical shape at the position of the base 15. This curved surface is constituted by the outer circumferential surface of the hood 20 and the outer circumferential surfaces of the levers 30.

It is preferable that the connector main body 3 is made of a hard material. Specifically, a resin material such as polyacetal, polycarbonate, polystyrene, polyamide, polypropylene, or rigid polyvinyl chloride may be used. The connector main body 3 can be integrally produced as a single component through injection molding or the like using such a resin material.

1. 2. Shield

Figure 3A:
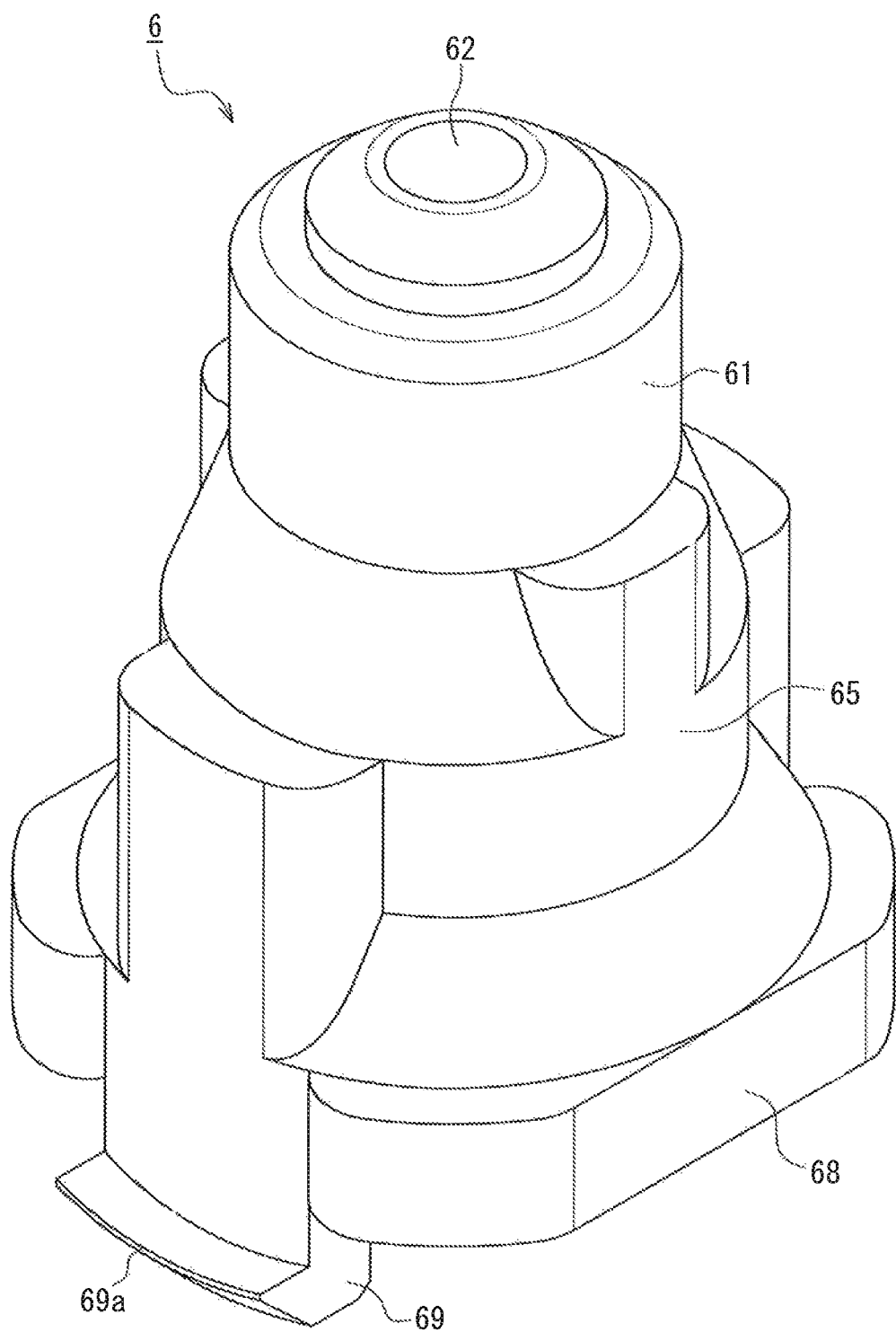
FIG. 3A is a perspective view of a shield according to Embodiment 1 of the present invention when viewed from above.
Figure 3B:
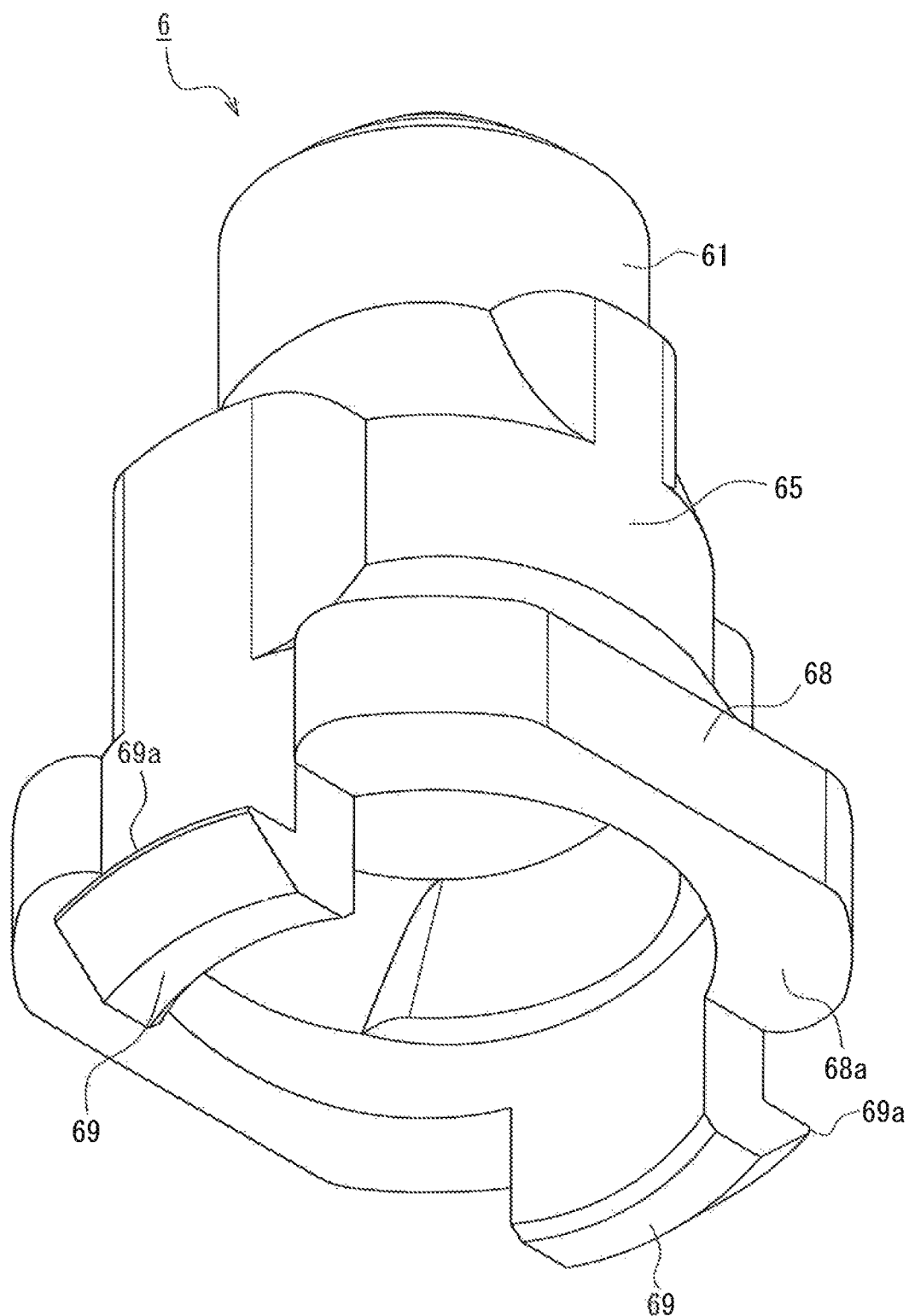
FIG. 3B is a perspective view of the shield according to Embodiment 1 of the present invention when viewed from below.
Figure 3C:
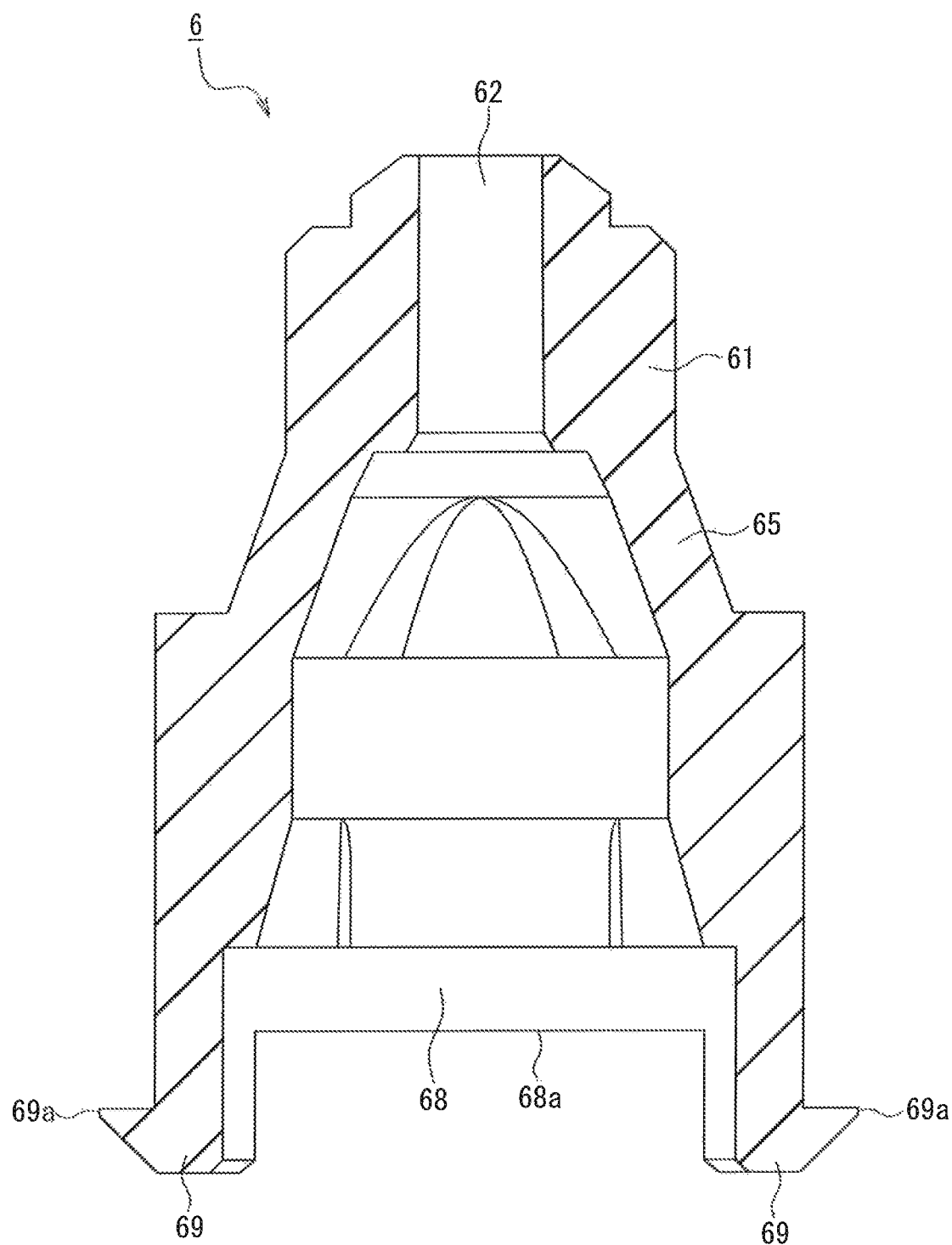
FIG. 3C is a cross-sectional view of the shield according to Embodiment 1 of the present invention taken along a vertical plane.

The shield 6 that constitutes the male connector 2 will be described below. FIG. 3A is a perspective view of the shield 6 when viewed from above, FIG. 3B is a perspective view of the shield 6 when viewed from below, and FIG. 3C is a cross-sectional view of the shield 6. The shield 6 includes a head portion 61, an outer circumferential wall 65, and a base portion 68 in this order from the top to the bottom. As shown in FIG. 3C, the shield 6 has a substantially tubular shape having a space penetrating the shield 6 in the vertical direction.

The shield 6 is integrally formed as a single component using a soft material (so-called elastomer) having rubber elasticity (or flexibility). The material for the shield 6 is not limited, but, for example, isoprene rubber, silicone rubber, butyl rubber, a thermoplastic elastomer, and the like can be used.

As shown in FIG. 3C, a through hole 62 is formed penetrating the head portion 61 in the vertical direction. It is preferable that an inner circumferential surface of the through hole 62 has a shape that conforms to the outer circumferential surface of the male luer 10 so as to come into intimate contact with the outer circumferential surface of the male luer 10 of the connector main body 3. In Embodiment 1, the inner circumferential surface of the through hole 62 constitutes a cylindrical tubular surface whose internal diameter is constant with respect to the vertical direction. It is preferable that the internal diameter of the through hole 62 is equal to or slightly smaller than the external diameter of the male luer 10 of the connector main body 3.

When a compressive force in the vertical direction is applied to the shield 6, the outer circumferential wall 65 is elastically compressively deformed such that its vertical dimension is reduced (see FIGS. 13D and 13E, which will be described later). As shown in FIG. 3C, the outer circumferential wall 65 has a larger internal diameter than the through hole 62 of the head portion 61. When the shield 6 is attached to the connector main body 3, the outer circumferential wall 65 is spaced apart from the male luer 10 in the radial direction (see FIGS. 5C and 5D, which will be described later). Thus, the likelihood of the inner circumferential surface of the outer circumferential wall 65 colliding with the male luer 10 when the outer circumferential wall 65 is compressively deformed in the vertical direction is reduced. This is advantageous in increasing the amount of compressive deformation of the outer circumferential wall 65 in the vertical direction.

Moreover, in the outer circumferential wall 65, a tapered (conical) portion where the external and internal diameters of the outer circumferential wall 65 increase as the distance from the head portion 61 increases and a cylindrical tubular portion where the external and internal diameters of the outer circumferential wall 65 are constant with respect to the vertical direction are alternatingly arranged in the vertical direction. Thus, the outer circumferential wall 65 as a whole has a conical shape that becomes gradually narrower toward the head portion 61. When a compressive force in the vertical direction is applied to the shield 6, this shape allows the outer circumferential wall 65 to deform such that the tapered portion is depressed into the cylindrical tubular portion below the tapered portion (see FIGS. 13D and 13E, which will be described later). This is advantageous in increasing the amount of compressive deformation of the outer circumferential wall 65 in the vertical direction.

The base portion 68 has a flat bottom surface 68a. A pair of fixing projections 69 protrude downward from the bottom surface 68a. A fixing claw 69a protrudes outward from an outer circumferential surface of each fixing projection 69. The fixing projections 69 and the fixing claws 69a are used to fix the shield 6 to the connector main body 3.

1. 3. Lock Ring

Figure 4A:
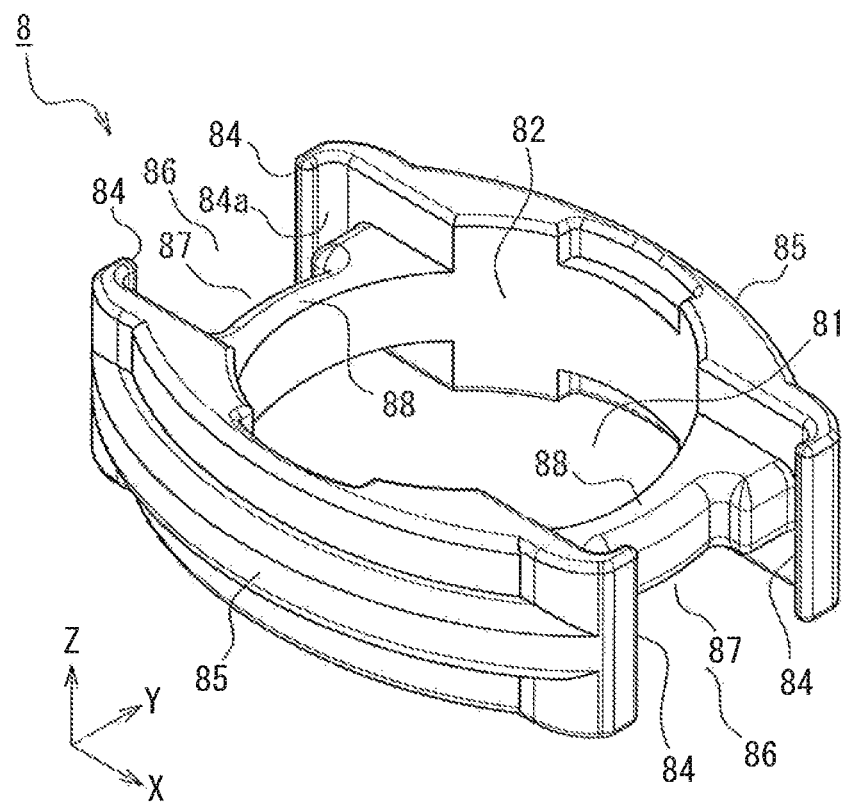
FIG. 4A is a perspective view of a lock ring according to Embodiment 1 of the present invention when viewed from above.
Figure 4B:
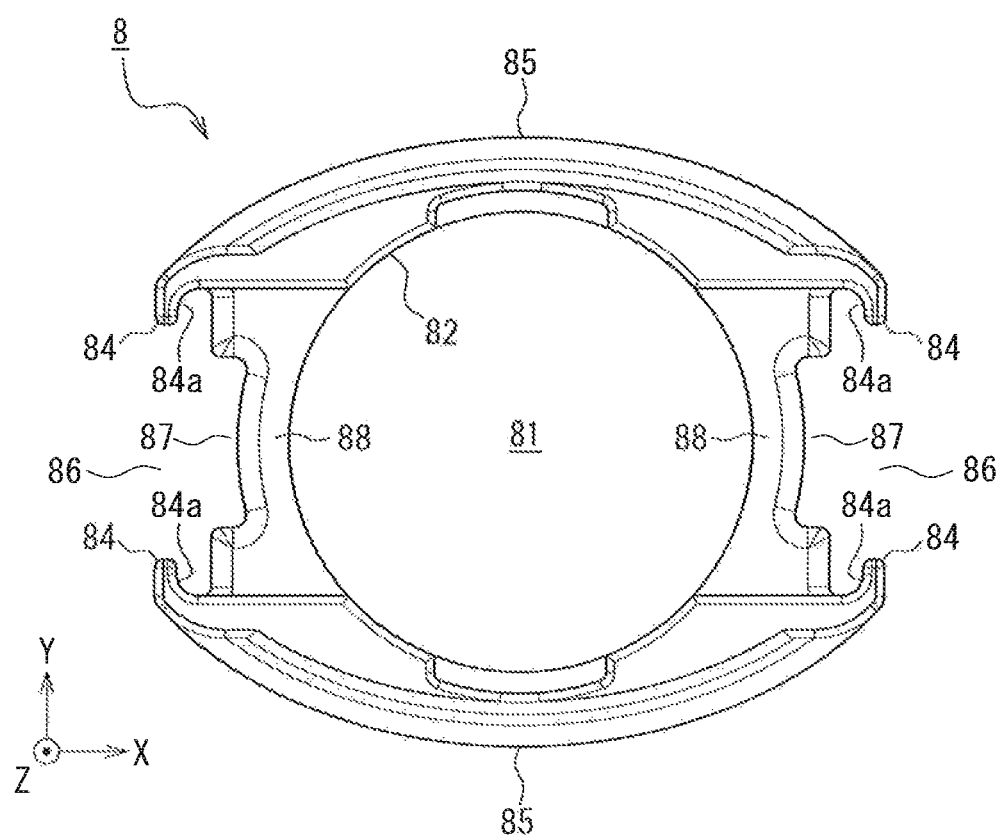
FIG. 4B is a plan view of the lock ring.

The lock ring 8 that constitutes the male connector 2 will be described below. FIG. 4A is a perspective view of the lock ring 8 when viewed from above, and FIG. 4B is a plan view of the lock ring 8.

The lock ring 8 has an annular shape in which a circular opening 81 is formed at the center. An inner circumferential surface 82 that surrounds the opening 81 constitutes a cylindrical tubular surface.

The lock ring 8 includes a pair of arch-shaped portions 85 that are arranged opposing each other in the Y-axis direction. A pair of bridging portions 88 couple the pair of arch-shaped portions 85 to each other. As shown in FIG. 4B, when the lock ring 8 is viewed from above (in plan view), outer surfaces of the arch-shaped portions 85 conform to a substantially elliptical shape that is almost the same as the substantially elliptical outline (see FIG. 2E) of the connector main body 3 in plan view. The arch-shaped portions 85 are disposed on the minor axis of the above-described elliptical shape. The bridging portions 88 are disposed on the major axis of the above-described ellipse and at respective positions that are individually shifted inward from the above-described ellipse. In other words, the substantially elliptical shape is cut out using a pair of cut-outs 86 that are provided on the major axis thereof. The surface of each bridging portion 88 that faces outward constitutes a flat surface that is parallel to the YZ plane. A groove 87 extending along the vertical direction is formed in this flat surface.

Claws 84 protrude from respective ends of each arch-shaped portion 85 toward the opposing arch-shaped portion 85. The claws 84 extend along the vertical direction. Each claw 84 includes a sliding surface 84a that opposes a corresponding one of the bridging portions 88.

The lock ring 8 has two-fold rotational symmetry (when rotated 180 degrees, the lock ring 8 coincides with its state prior to rotation). Although omitted from the drawings, even if the lock ring 8 is inverted, the lock ring 8 has the same shape.

It is preferable that the lock ring 8 is made of a hard material. Specifically, a resin material such as polyacetal, polycarbonate, polystyrene, polyamide, polypropylene, or rigid polyvinyl chloride may be used. The lock ring 8 can be integrally produced as a single component through injection molding or the like using such a resin material.

1. 4. Assembling of Male Connector

Figure 5A:
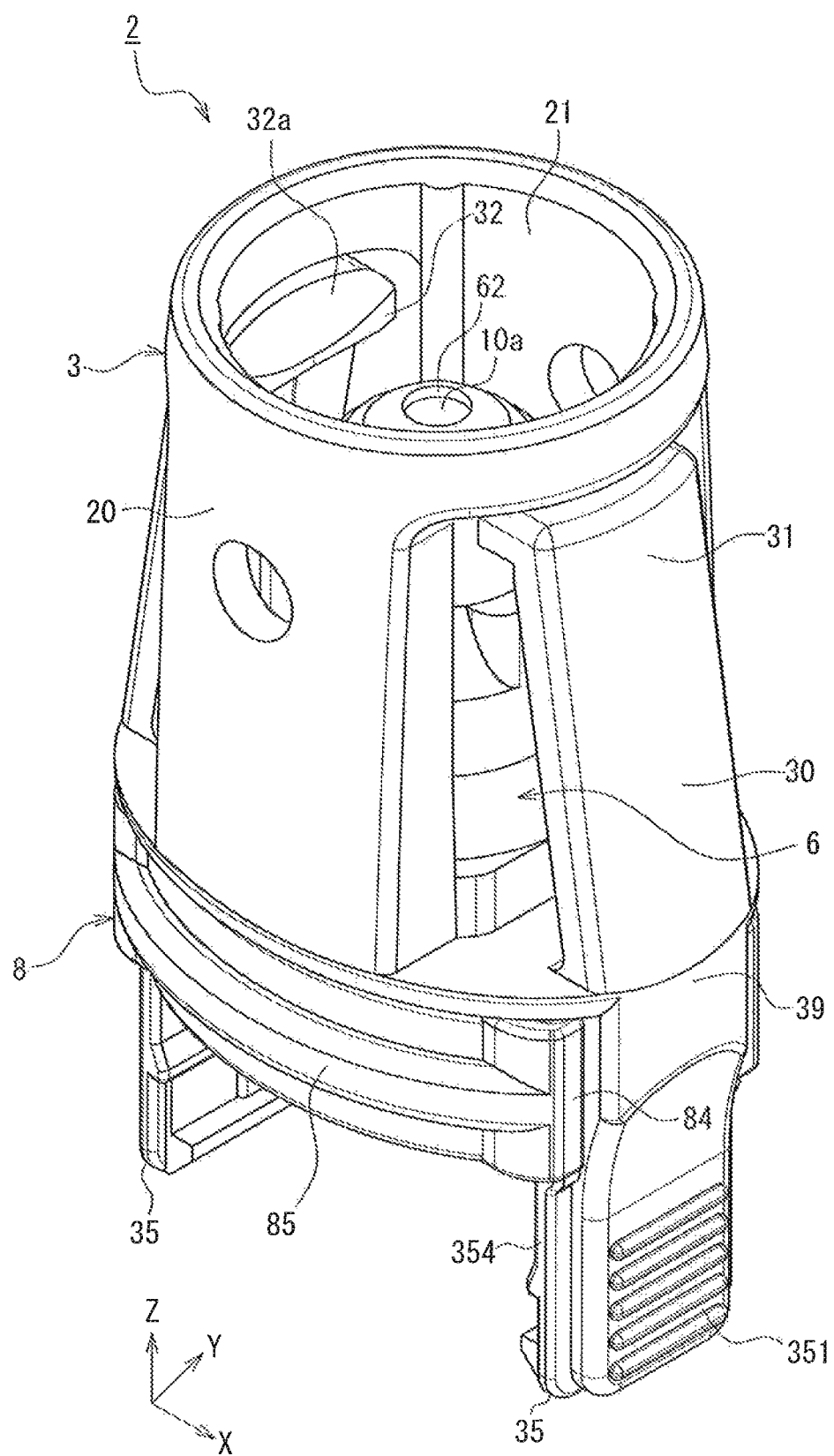
FIG. 5A is a perspective view of a lever lock-type male connector according to Embodiment 1 of the present invention when viewed from above.
Figure 5B:
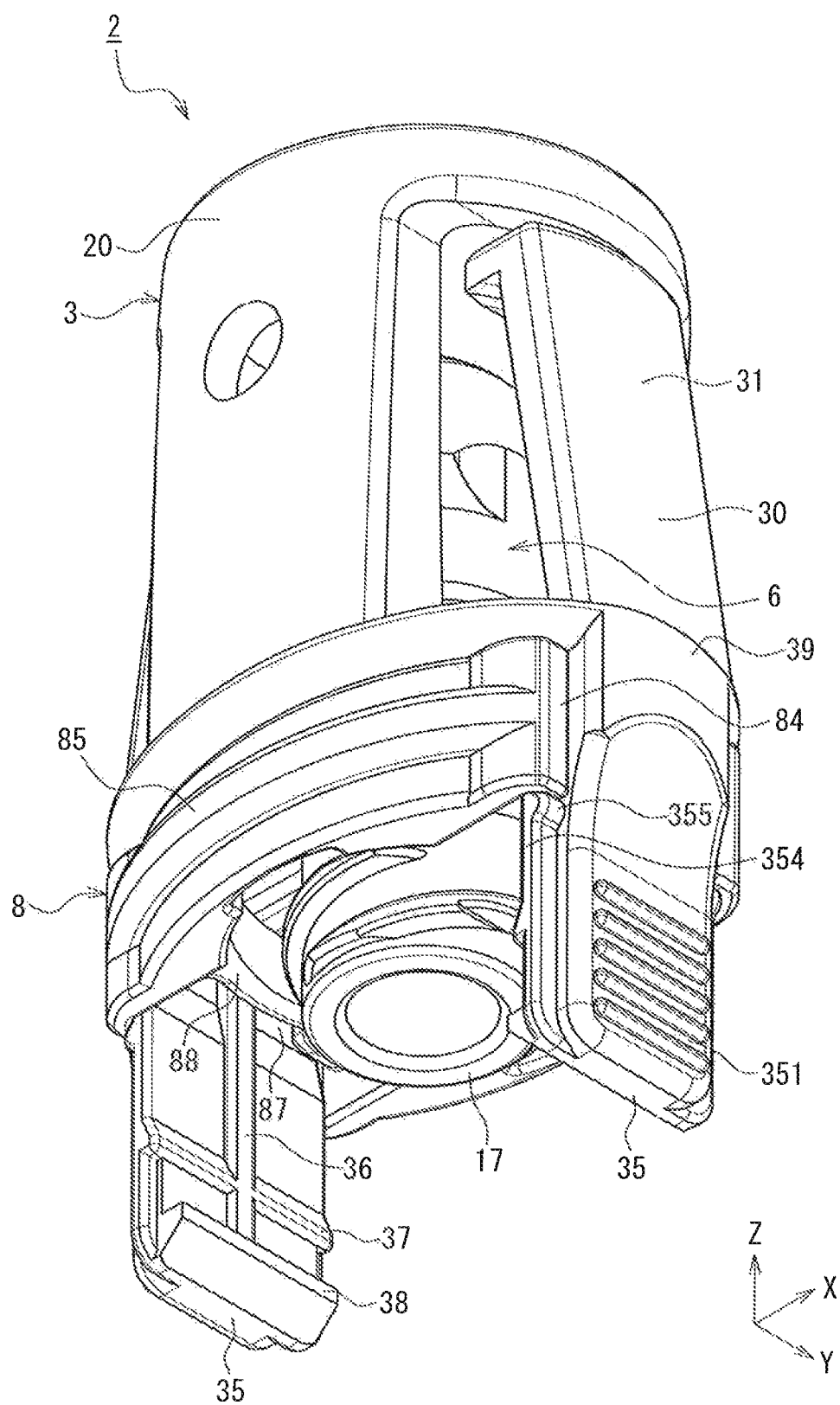
FIG. 5B is a perspective view of the lever lock-type male connector according to Embodiment 1 of the present invention when viewed from below.
Figure 5C:
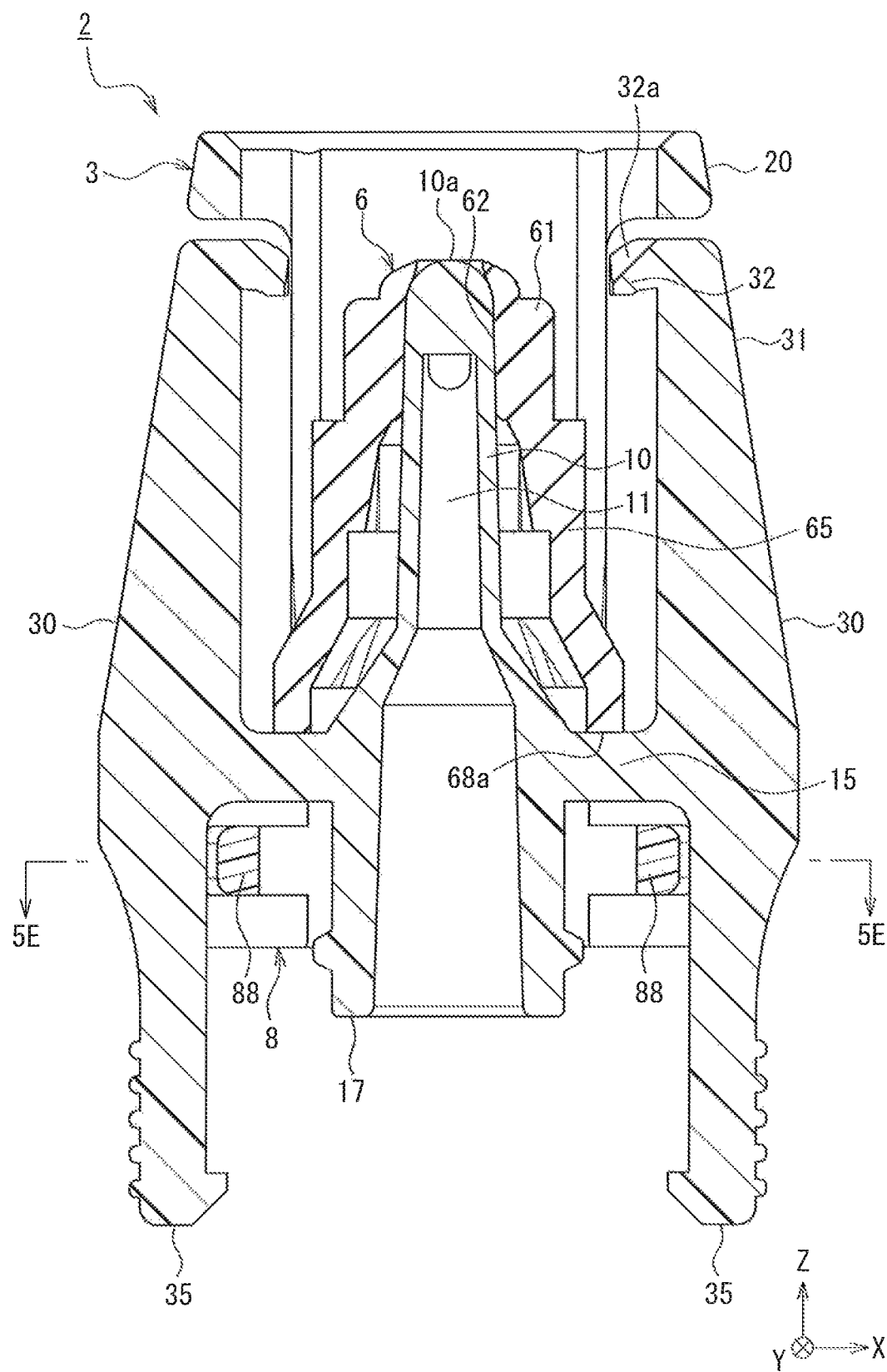
FIG. 5C is a cross-sectional view of the lever lock-type male connector according to Embodiment 1 of the present invention.
Figure 5D:
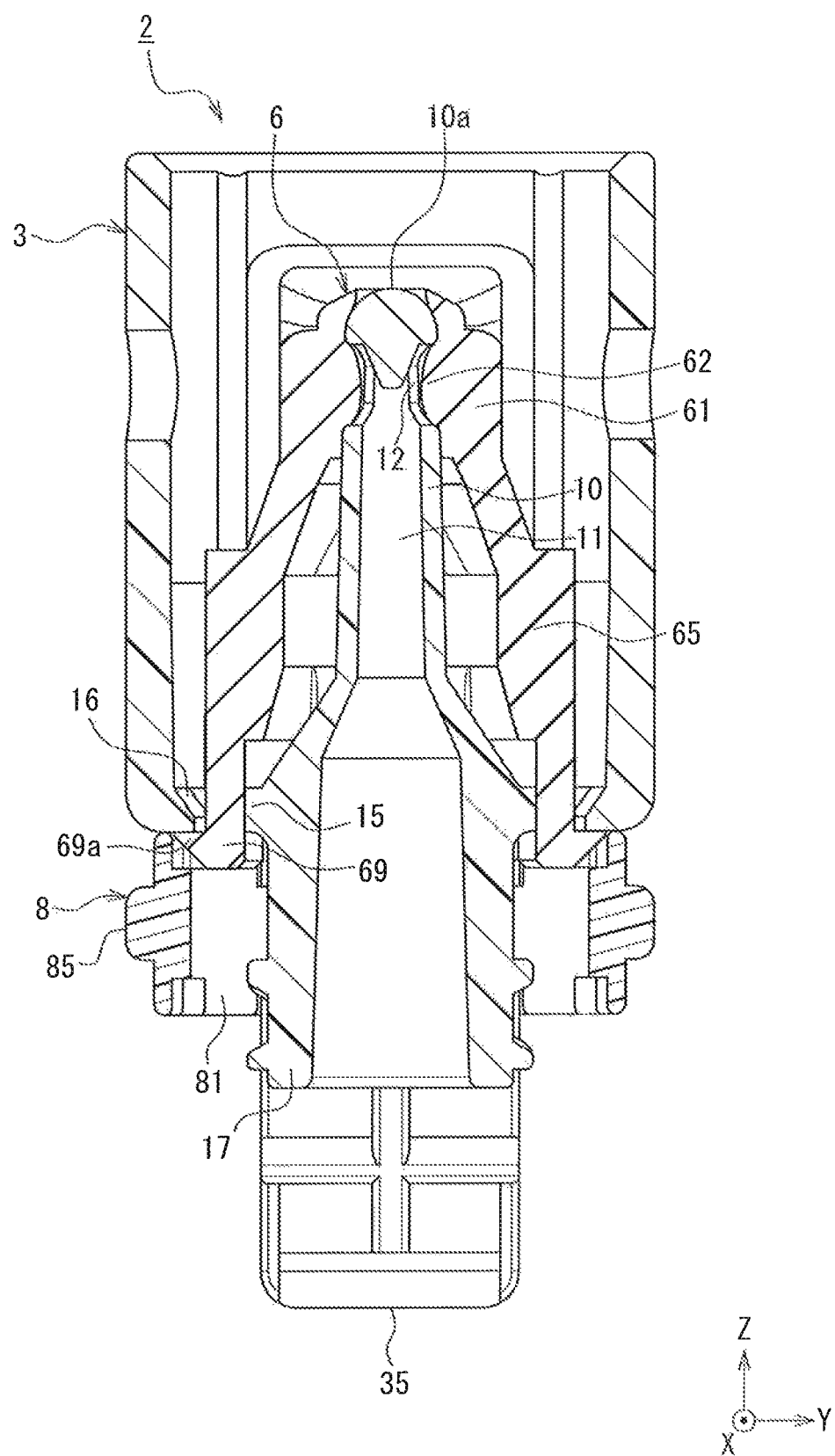
FIG. 5D is a cross-sectional view of the lever lock-type male connector according to Embodiment 1 of the present invention taken along another plane.
Figure 5E:
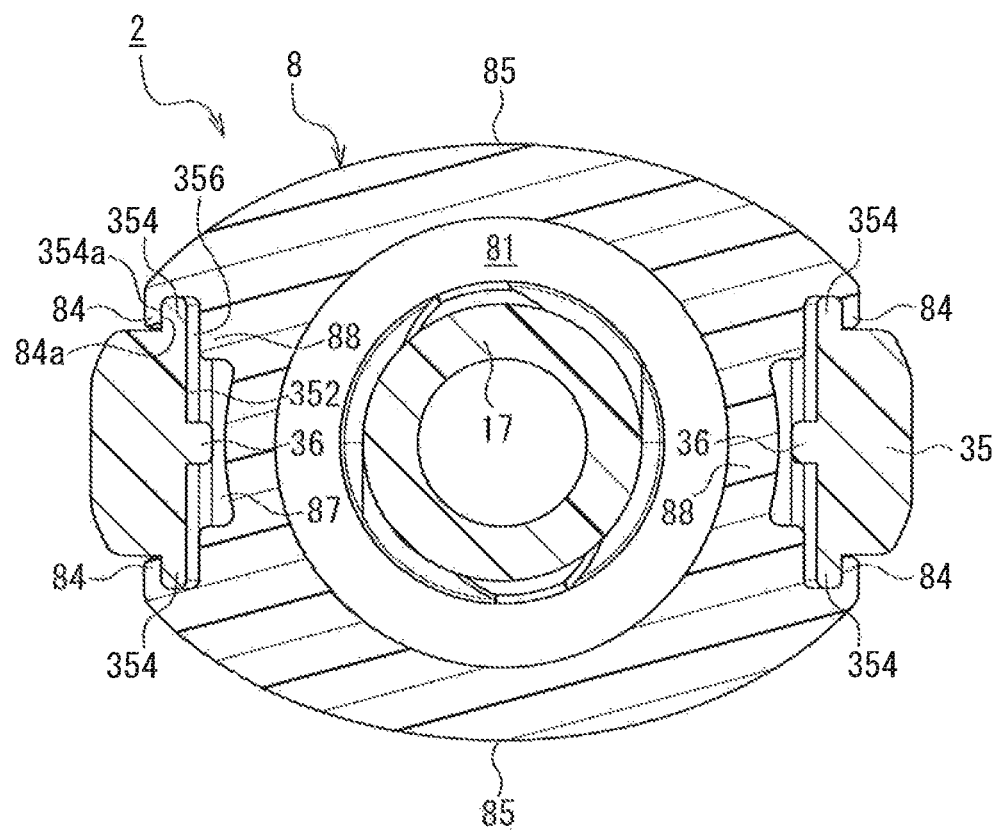
FIG. 5E is a cross-sectional view of the lever lock-type male connector according to Embodiment 1 of the present invention taken along a horizontal plane containing line 5E-5E in FIG. 5C.

As shown in FIG. 1, the shield 6 is inserted into the hood 20 from above the connector main body 3. Also, the lock ring 8 is inserted between the pair of operating portions 35 from below the connector main body 3. FIG. 5A is a perspective view of the male connector 2 when viewed from above, with the shield 6 and the lock ring 8 attached to the connector main body 3, and FIG. 5B is a perspective view of the male connector 2 when viewed from below. FIG. 5C is a cross-sectional view of the male connector 2 taken along a plane (XZ plane) containing the central axis 3a and the major axis 15a, and FIG. 5D is a cross-sectional view of the male connector 2 taken along a plane (YZ plane) containing the central axis 3a and the minor axis 15b. FIG. 5E is a cross-sectional view of the male connector 2 taken along a horizontal plane containing line 5E-5E in FIG. 5C. A plan view of the male connector 2 is not given because it is the same as that shown in FIG. 2E except that the shield 6 is provided.

As shown in FIG. 5D, the fixing projections 69 of the shield 6 are inserted in the respective holes 16 that are provided in the base 15 of the connector main body 3. The fixing claws 69a have passed through the holes 16 and are engaged with a lower surface of the base 15. The bottom surface 68a of the shield 6 is in intimate contact with an upper surface of the base 15 (FIG. 5C).

The leading end 10a and its neighboring portion of the male luer 10 are inserted into the through hole 62 of the head portion 61 of the shield 6. The leading end 10a of the male luer 10 is exposed in the through hole 62 of the head portion 61. The inner circumferential surface of the through hole 62 appropriately deforms in accordance with the external shape of the outer circumferential surface of the male luer 10 and is in intimate contact with that outer circumferential surface. The openings of the lateral holes 12 of the male luer 10 are closed off in a liquid-tight manner by the inner circumferential surface of the through hole 62.

The outer circumferential wall 65 of the shield 6 is spaced apart from the male luer 10 in the radial direction. Thus, a liquid-tight space is formed between the shield 6 and the connector main body 3. Moreover, the outer circumferential wall 65 is spaced apart from both the hood 20 and the levers 30 in the radial direction.

As shown in FIG. 5B, the tubular portion 17 of the connector main body 3 is inserted into the opening 81 (see FIG. 4A) of the lock ring 8. The operating portions 35 of the connector main body 3 are fitted in the respective cut-outs 86 (see FIG. 4A) of the lock ring 8. The ribs 36 of the operating portions 35 are located within the respective grooves 87 provided in the bridging portions 88, and thus, collision of the ribs 36 with the bridging portions 88 is avoided.

Each pair of the claws 84 of the lock ring 8, which oppose each other in the Y-axis direction, hold a corresponding one of the operating portions 35 that is disposed therebetween, from both sides. Thus, the lock ring 8 is not rotatable relative to the connector main body 3.

On the other hand, the lock ring 8 is movable in the vertical direction in a state in which each operating portion 35 is held between the claws 84 as described above. Upward movement of the lock ring 8 is restricted by the lock ring 8 colliding with the lower surface of the base 15. Downward movement of the lock ring 8 is restricted by the lock ring 8 (in particular, bridging portions 88 thereof) colliding with the stopping projections 38 provided on the operating portions 35. FIGS. 5A to 5E show a state in which the lock ring 8 has been moved uppermost (highest position; first position).

When the lock ring 8 is at its highest position, the locking projections (first locking projections) 355, which protrude from the sliding ribs 354, are located immediately below the respective claws 84, and the claws 84 are close to or abut against the locking projections 355 in the vertical direction. Thus, the lock ring 8 is prevented from being lowered from the highest position due to gravity, vibrations, and the like. That is to say, the locking projections 355 that are close to or abut against the lock ring 8 constitute a "first movement prevention mechanism" that prevents the lock ring 8 at its highest position from being unintentionally lowered. Since the lock ring 8 is held at its highest position, the ease of operations for connecting and disconnecting the male connector 2 (FIGS. 5A to 5E) to and from the screw lock-type connector 100 (FIGS. 8A and 8B) (the details of which will be described later) and the ease of operations for connecting and disconnecting the male connector assembly 1 (FIGS. 9A and 9B) to and from a female connector 900 (FIGS. 10A and 10B) (the details of which will be described later) do not deteriorate.

When the lock ring 8 is at its highest position, the bridging portions 88 (see FIG. 4A) of the lock ring 8 oppose the recessed regions 352a (see FIG. 2B) of the operating portions 35, respectively, in the X-axis direction. Accordingly, as shown in FIG. 5E, the inner surface 352 (recessed region 352a) of each operating portion 35 is spaced apart from a corresponding one of the bridging portions 88 of the lock ring 8 in the X-axis direction, and a gap 356 is formed therebetween. Thus, when a force F is applied to the outer surfaces 351 of the operating portions 35 in a state in which the lock ring 8 is at its highest position, as described above with reference to FIG. 2F, the levers 30 can be pivoted such that the locking portions 31 and the locking claws 32 move away from the male luer 10 (in the directions of arrows A). Moreover, as will be described later, when the female connector 900 is inserted into the hood 20 in a state in which the lock ring 8 is at its highest position, the female connector 900 collides with the locking claws 32 and can cause the levers 30 to pivot such that the locking claws 32 move away from the male luer 10 (in the directions of arrows A in FIG. 2F). Accordingly, the ease of operations for connecting and disconnecting a female connector is improved.

When the inner surfaces 352 of the operating portions 35 are spaced apart from the respective bridging portions 88 of the lock ring 8 in the X-axis direction as described above, a problematic situation may occur in which the lock ring 8 inclines relative to the connector main body 3 such that one end of the lock ring 8 is raised with respect to the X-axis direction, while the other end is lowered, and eventually, the lock ring 8 falls downward from between the pair of operating portions 35. According to Embodiment 1, the lock ring 8 is engaged with the operating portions 35 in the X-axis direction, and thus, this situation is prevented from occurring. More specifically, the claws 84 of the lock ring 8 are engaged with the sliding ribs 354 of the operating portions 35. Therefore, if the lock ring 8 inclines relative to the connector main body 3 as described above, the sliding surfaces 84a (see FIGS. 4A and 4B) of the claws 84 collide with the outer surfaces of the respective sliding ribs 354. Thus, the lock ring 8 is restricted from inclining, so that it is possible to prevent the lock ring 8 from falling downward from between the pair of operating portions 35 as a result of the lock ring 8 being inclined.

According to Embodiment 1, when the lock ring 8 is at its highest position, the sliding surfaces 84a of the claws 84 oppose the pressure contact portions 354a (see FIG. 2B) of the respective sliding ribs 354 in the X-axis direction. Preferably, as shown in FIG. 5E, the sliding surfaces 84a of the claws 84 abut against the pressure contact portions 354a of the respective sliding ribs 354 in the X-axis direction. Therefore, the lock ring 8 is prevented from inclining as described above, and consequently, the lock ring 8 can be more reliably prevented from falling from between the pair of operating portions 35. Moreover, the lock ring 8 can be positioned relative to the connector main body 3 with respect to the X-axis direction.

In the present invention, a state in which, as shown in FIGS. 5A to 5E, substantially no external force acts on the levers 30, the shield 6 is not compressively deformed in the vertical direction, and the lock ring 8 has been moved to the highest position is referred to as the "initial state" of the male connector 2.

2. Screw Lock-Type Connector 2. 1. Luer Main Body

The luer main body 110 that constitutes the screw lock-type connector 100 will be described below. FIG. 6A is a perspective view of the luer main body 110, and FIG. 6B is a cross-sectional view of the luer main body 110.

The luer main body 110 has a substantially cylindrical tubular shape as a whole, in which a through hole (flow channel) 111 along the longitudinal direction of the luer main body 110 is formed. The luer main body 110 includes a male luer 112, a tubular portion 115, and a connecting portion 119 in this order from the top to the bottom.

An outer circumferential surface 112a of the male luer 112 constitutes a male tapered surface (e.g., a 6% tapered surface) whose external diameter gradually decreases toward the leading end. An outer circumferential surface of the tubular portion 115 constitutes a cylindrical tubular surface whose external diameter is constant with respect to the vertical direction. A pair of protruding portions 116 protrude outward from the outer circumferential surface of the tubular portion 115. An annular projection 117 continuously extending in the circumferential direction is provided at the boundary between the male luer 112 and the tubular portion 115. The annular projection 117 has an external diameter that is larger than those of the male luer 112 and the tubular portion 115.

It is preferable that the luer main body 110 is made of a hard material. Specifically, a resin material such as polyacetal, polycarbonate, polystyrene, polyamide, polypropylene, or rigid polyvinyl chloride may be used. The luer main body 110 can be integrally produced as a single component through injection molding or the like using such a resin material.

2. 2. Lock Nut

Figure 7A:
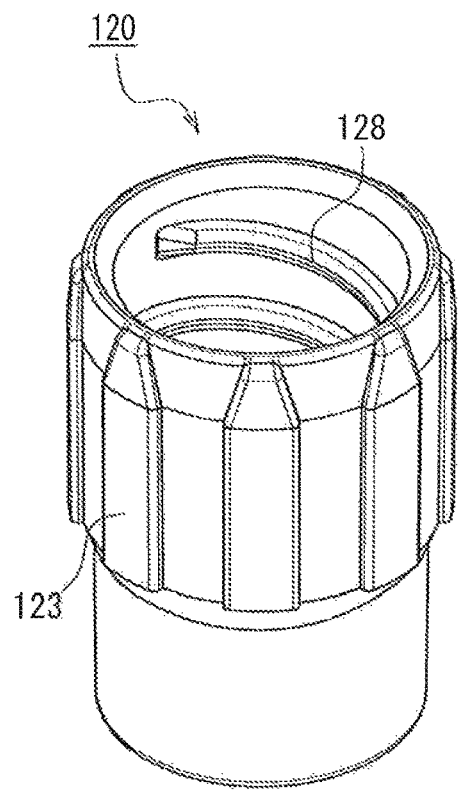
FIG. 7A is a perspective view of a lock nut according to Embodiment 1 of the present invention when viewed from above.
Figure 7B:
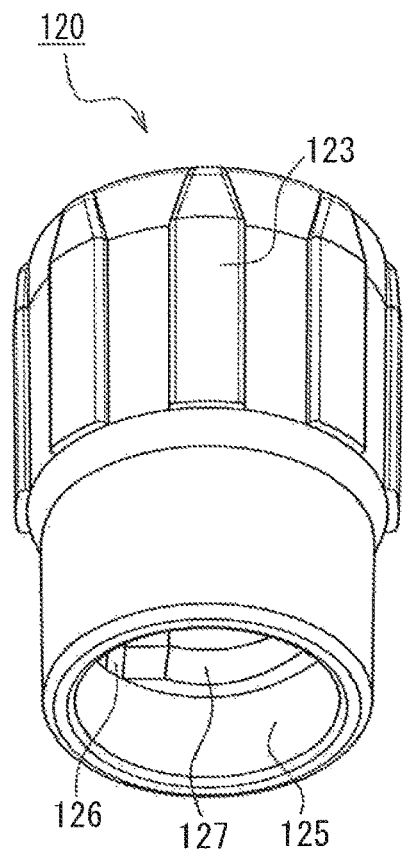
FIG. 7B is a perspective view of the lock nut when viewed from below.
Figure 7C:
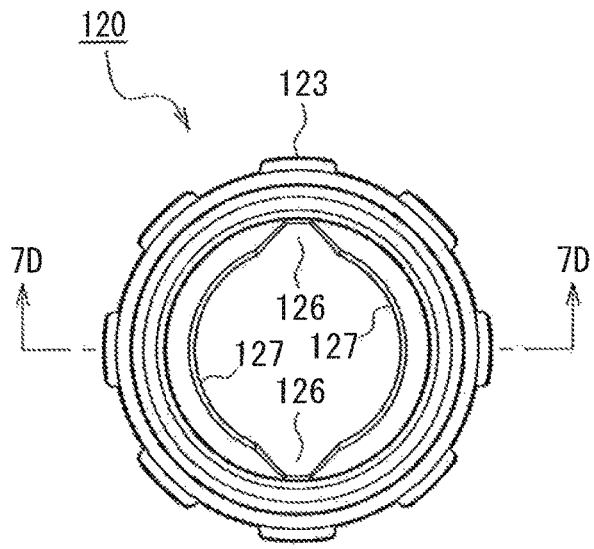
FIG. 7C is a plan view of the lock nut.
Figure 7D:
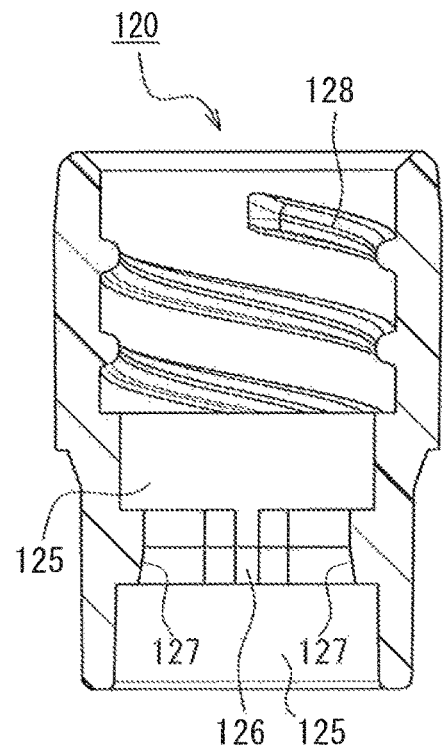
FIG. 7D is a cross-sectional view of the lock nut taken along a vertical plane containing line 7D-7D in FIG. 7C.

The lock nut 120 that constitutes the screw lock connector 100 will be described below. FIG. 7A is a perspective view of the lock nut 120 when viewed from above, FIG. 7B is a perspective view of the lock nut 120 when viewed from below, FIG. 7C is a plan view of the lock nut 120, and FIG. 7D is a cross-sectional view of the lock nut 120. The lock nut 120 has a hollow, substantially cylindrical tubular shape as a whole.

The outer circumferential surface of the lock nut 120 is constituted by two cylindrical tubular surfaces having different external diameters. A plurality of ribs 123 protrude outward from the upper cylindrical tubular surface having a relatively large external diameter. The ribs 123 extend along the vertical direction. In Embodiment 1, the number of ribs 123 is eight; however, the present invention is not limited to this, and the number of ribs 123 may be more than eight or less than eight. In the case where two or more ribs 123 are provided, preferably the ribs 83 are arranged at regular intervals in the circumferential direction. In Embodiment 1, the outer circumferential surface of the lock nut 120 is constituted by the two cylindrical tubular surfaces; however, the present invention is not limited to this. For example, the entire outer circumferential surface from the upper end to the lower end may be constituted by a single cylindrical tubular surface. Alternatively, the outer circumferential surface may contain a surface (e.g., a polygonal prism-shaped surface) other than a cylindrical tubular surface.

A female thread 128 is formed on an inner circumferential surface of the lock nut 120, the female thread 128 extending in a region from an upper end to the substantially middle of the inner circumferential surface of the lock nut 120. A portion of the inner circumferential surface of the lock nut 120 that is located below the female thread 128 constitutes a cylindrical tubular surface 125 having a constant internal diameter. A position-restricting projection 127 extending in the circumferential direction protrudes from the cylindrical tubular surface 125. A pair of guide passages 126 are formed in the position-restricting projection 127. The guide passages 126 extend in the vertical direction. The guide passages 126 divide the position-restricting projection 127 in the circumferential direction.

It is preferable that the lock nut 120 is made of a hard material. Specifically, a resin material such as polyacetal, polycarbonate, polystyrene, polyamide, polypropylene, or rigid polyvinyl chloride may be used. The lock nut 120 can be integrally produced as a single component through injection molding or the like using such a resin material.

2. 3. Assembling of Screw Lock-Type Connector

Figure 8A:
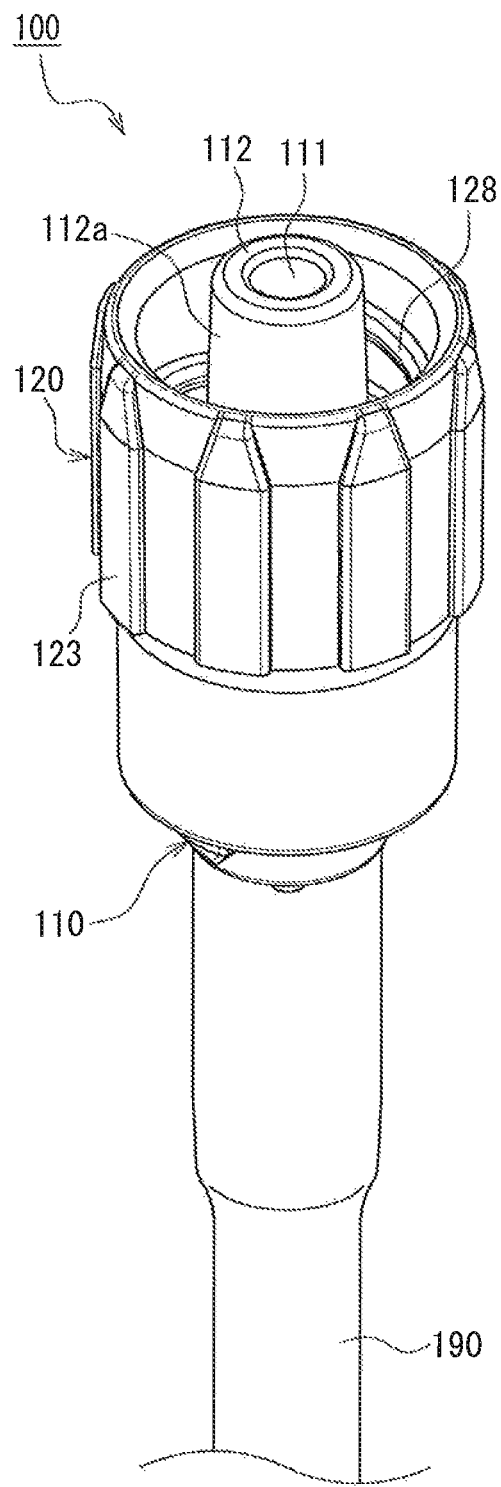
FIG. 8A is a perspective view of a screw lock-type connector according to Embodiment 1 of the present invention.

As shown in FIG. 1, the flexible tube 190 is passed through the lock nut 120. Then, the connecting portion 119 of the luer main body 110 is inserted into an upper end of the tube 190. Subsequently, the lock nut 120 is moved upward. The luer main body 110 is inserted into the inside of the female thread 128 of the lock nut 120. The protruding portions 116 protruding from the outer circumferential surface of the luer main body 110 may possibly collide with the position-restricting projection 127 protruding from the inner circumferential surface of the lock nut 120. If this is the case, the lock nut 120 is slightly rotated relative to the luer main body 110. When the positions of the protruding portions 116 of the luer main body 110 with respect to the circumferential direction coincide with the positions of the respective guide passages 126 of the lock nut 120 with respect to the circumferential direction, the protruding portions 116 can pass through the guide passages 126. In this manner, the screw lock connector 100 can be assembled as shown in FIGS. 8A and 8B.

Figure 8B:
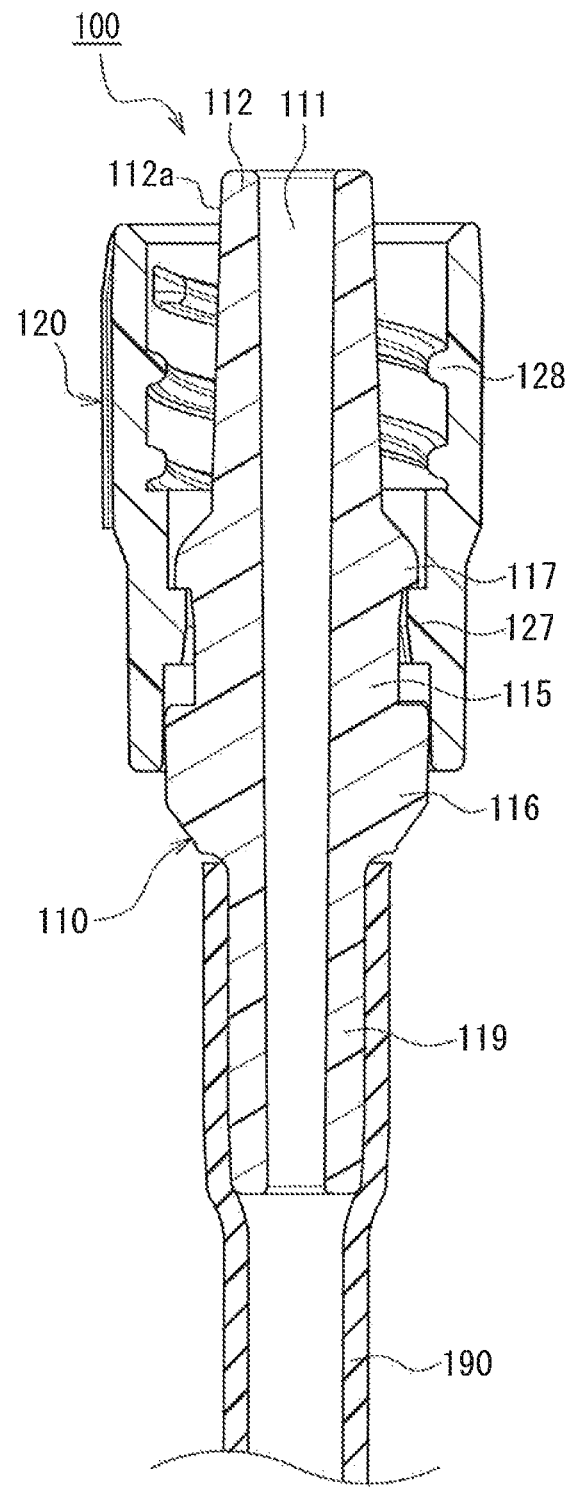
FIG. 8B is a cross-sectional view of the screw lock-type connector.

As shown in FIG. 8B, the position-restricting projection 127 of the lock nut 120 is located between the annular projection 117 and the protruding portions 116 of the luer main body 110. Due to the position-restricting projection 127 colliding with the annular projection 117 and the protruding portions 116, the lock nut 120 is restricted from moving upward (toward the tapered surface 112) and downward (toward the connecting portion 119) relative to the luer main body 110. However, the lock nut 120 can freely rotate around the luer main body 110.

3. Connection of Male Connector and Screw Lock-Type Connector (Assembling of Male Connector Assembly)

The male connector 2 (FIGS. 5A to 5E) and the screw lock connector 100 (FIGS. 8A and 8B) can be connected to each other by inserting the male luer 112 of the luer main body 110 into the tubular portion 17 of the connector main body 3 and screwing the female thread 128 of the lock nut 120 onto the male thread 18 of the tubular portion 17.

Figure 9A:
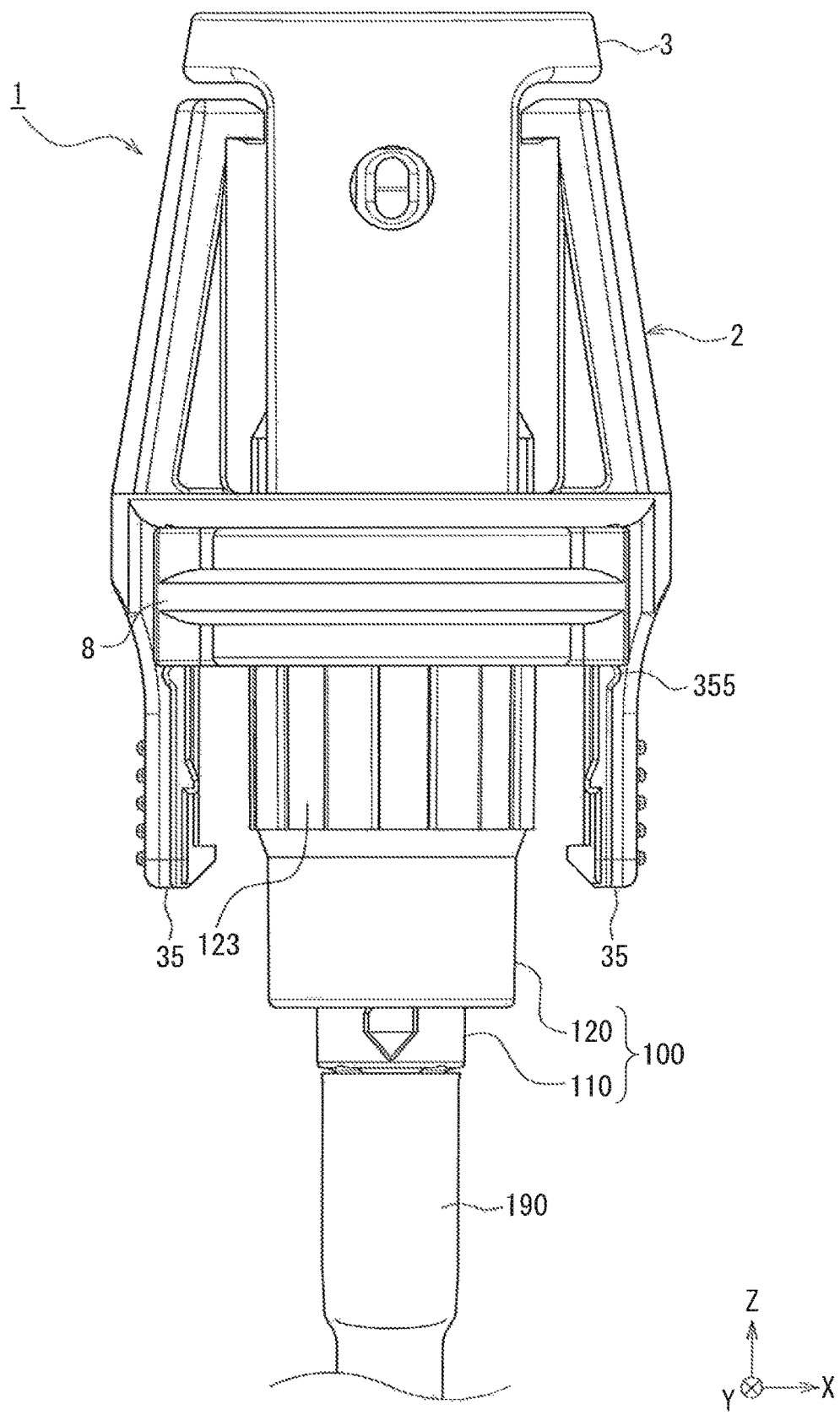
FIG. 9A is a side view of a male connector assembly according to Embodiment 1 of the present invention.
Figure 9B:
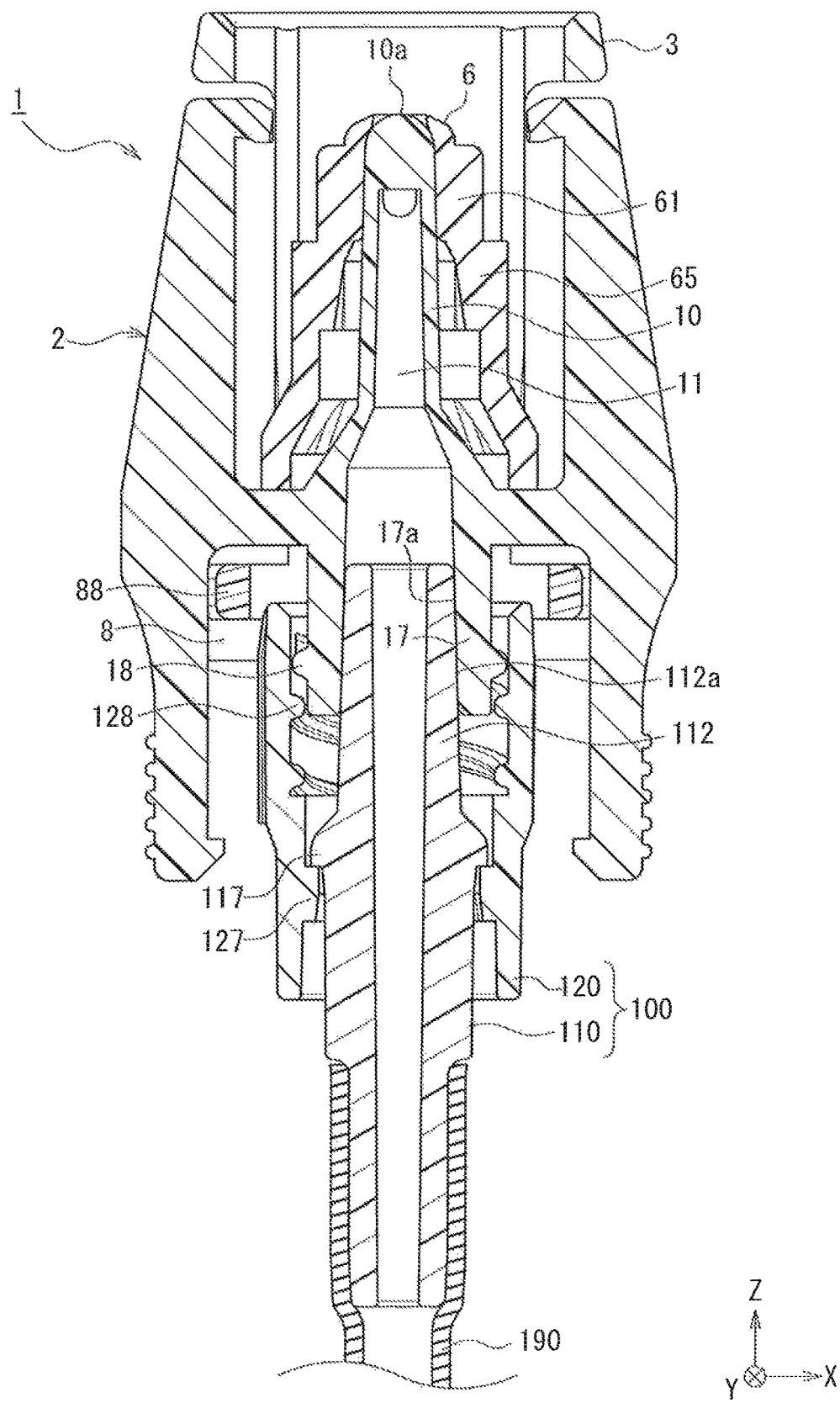
FIG. 9B is a vertical cross-sectional view of the male connector assembly according to Embodiment 1 of the present invention.

FIG. 9A is a side view of the male connector assembly 1 that is obtained by connecting the male connector 2 and the screw lock connector 100 to each other, and FIG. 9B is a vertical cross-sectional view of the male connector assembly 1.

The outer circumferential surface 112a of the male luer 112 and the inner circumferential surface 17a of the tubular portion 17 are the tapered surfaces having the same diameter and taper angle. Accordingly, as shown in FIG. 9B, the outer circumferential surface 112a and the inner circumferential surface 17a come into intimate contact with each other in a liquid-tight manner. Thus, the tube 190 and the flow channel 11 of the male luer 10 are in communication with each other.

The female thread 128 of the lock nut 120 and the male thread 18 of the tubular portion 17 are screwed together. Moreover, the position-restricting projection 127 of the lock nut 120 and the annular projection 117 of the luer main body 110 are engaged with each other. Thus, the male luer 112 and the tubular portion 17 are securely connected to each other. Even when an unintentional pull force acts between the male connector 2 (or the connector main body 3) and the screw lock-type connector 100 (or the luer main body 110), the male connector 2 and the screw lock-type connector 100 will not be disconnected from each other.

As shown in FIG. 9A, the lock nut 120 is disposed between the pair of operating portions 35. In the initial state in which the lock ring 8 has been moved to its highest position, a large portion of the lock nut 120 is located below the lock ring 8. Therefore, it is possible to rotate the lock nut 120 while using the ribs 123, which are formed on the outer circumferential surface of the lock nut 120, as an anti-slipping structure, to screw or unscrew the female thread 128 onto or from the male thread 18.

4. Method of Use 4. 1. Female Connector

Figure 10A:
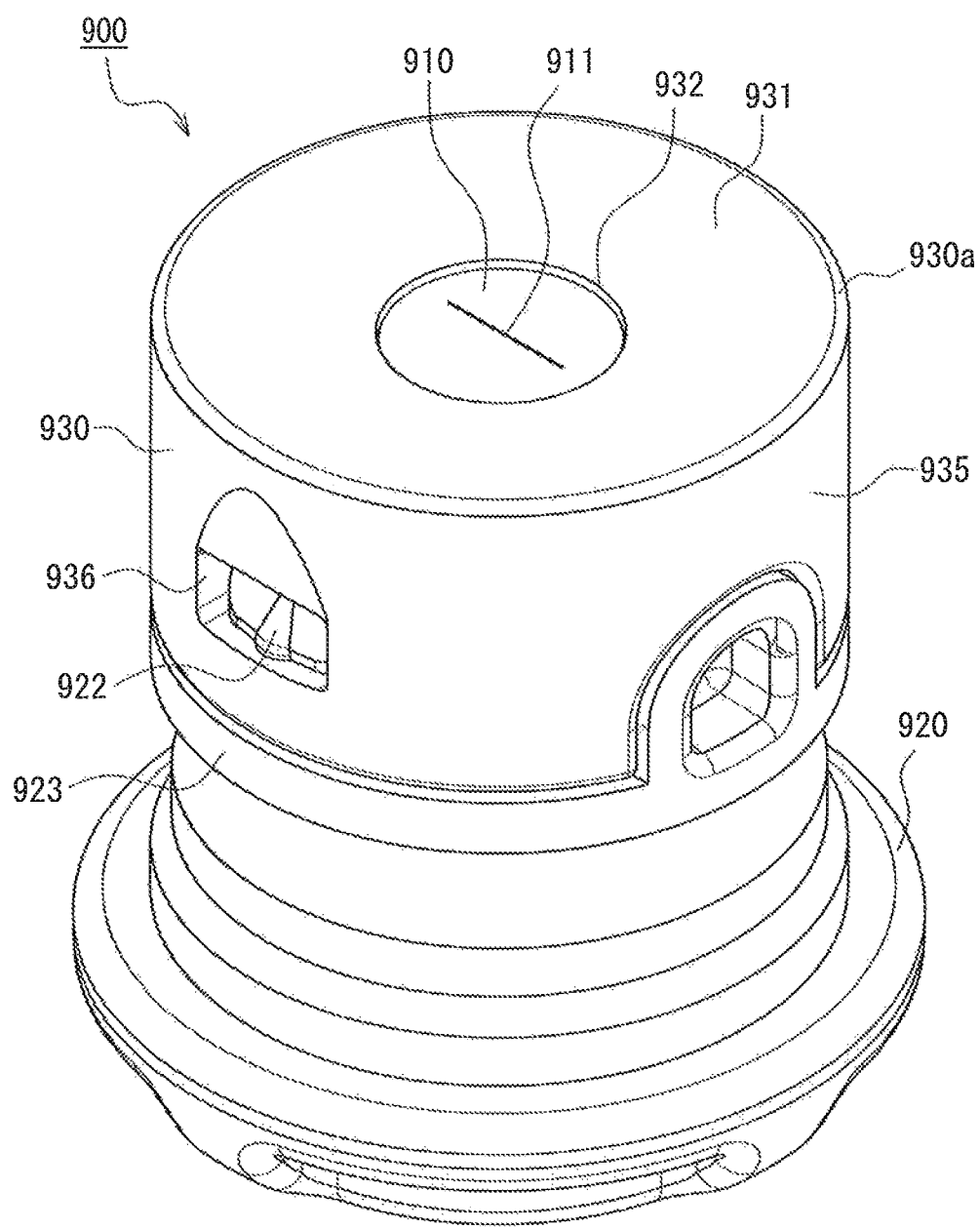
FIG. 10A is a perspective view of an example of a female connector to which the male connector assembly according to Embodiment 1 of the present invention is connectable.
Figure 10B:
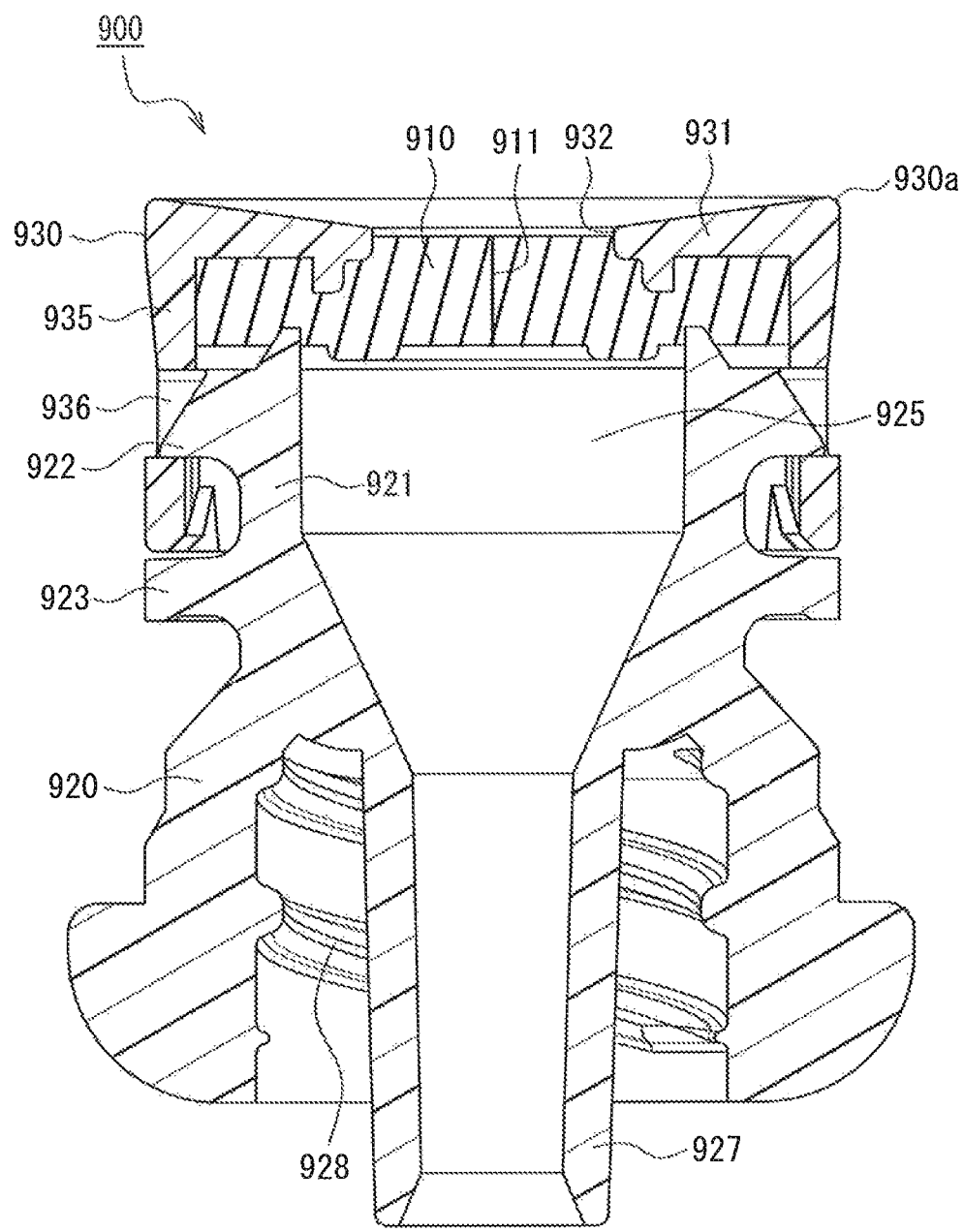
FIG. 10B is a cross-sectional view of the female connector.

The male connector assembly 1 is used connected to a female connector. FIGS. 10A and 10B show an example of the female connector. FIG. 10A is a perspective view of the female connector 900, and FIG. 10B is a cross-sectional view of the female connector 900.

The female connector 900 includes the circular plate-shaped partition member (hereinafter referred to as "septum") 910 as well as a mount 920 and a cap 930 that sandwich and fix the septum 910 in the vertical direction.

A straight line-shaped slit (cut portion) 911 penetrating the septum 910 in the vertical direction is formed at the center of the septum 910. The material for the septum 910 is not limited, but a soft material having rubber elasticity is preferable, and for example, isoprene rubber, silicone rubber, butyl rubber, a thermoplastic elastomer, and the like can be used.

The mount 920 includes, in an upper portion thereof, a seat 921 having a substantially cylindrical tubular shape. An outer circumferential surface of the seat 921 constitutes a cylindrical tubular surface. A pair of engagement claws 922 and an annular projection 923 protrude outward form the outer circumferential surface of the seat 921. The annular projection 923 is slightly spaced downward from the engagement claws 922.

A male luer 927 that is in communication with a cavity 925 in the seat 921 and a female thread 928 that is coaxial with the male luer 927 are provided below the seat 921. An outer circumferential surface of the male luer 927 constitutes a male tapered surface (conical surface) whose external diameter decreases as the distance to the leading end decreases (that is, as the distance from the seat 921 increases).

The cap 930 includes a top plate 931 having a circular plate-like shape, and a peripheral wall 935 extending downward from an outer circumferential end edge of the top plate 931 and having a cylindrical tubular shape. A circular opening (through hole) 932 is formed at the center of the top plate 931. A pair of engagement holes 936 are formed in the peripheral wall 235. The engagement holes 936 are through holes that penetrate the peripheral wall 935 in the radial direction.

As shown in FIG. 10B, the septum 910 is placed on the upper end of the seat 921, and the septum 910 is covered with the cap 930 from above. The engagement claws 922 formed on the seat 921 are fitted into the respective engagement holes 936 formed in the cap 930, and thus, the cap 930 is engaged with the engagement claws 922. As a result, the cap 930 is fixed to the mount 920 (see FIG. 10A). The septum 910 is sandwiched between the upper end of the seat 921 and the top plate 931 of the cap 930 in the thickness direction (i.e., vertical direction). The slit 911 of the septum 910 is exposed in the opening 932 that is formed in the top plate 931. The annular projection 923 formed on the mount 920 is located below and adjacent to the peripheral wall 935 of the cap 930. A top surface of the annular projection 923 constitutes a cylindrical tubular surface that is substantially the same as the outer circumferential surface of the peripheral wall 235.

The female connector 900 including the septum 910 in which the slit 911 is formed is generally called a needleless port.

4. 2. Connection and Disconnection of Male Connector Assembly and Female Connector The male connector assembly 1 and the female connector 900 can be connected to each other in the following manner.

Figure 11:
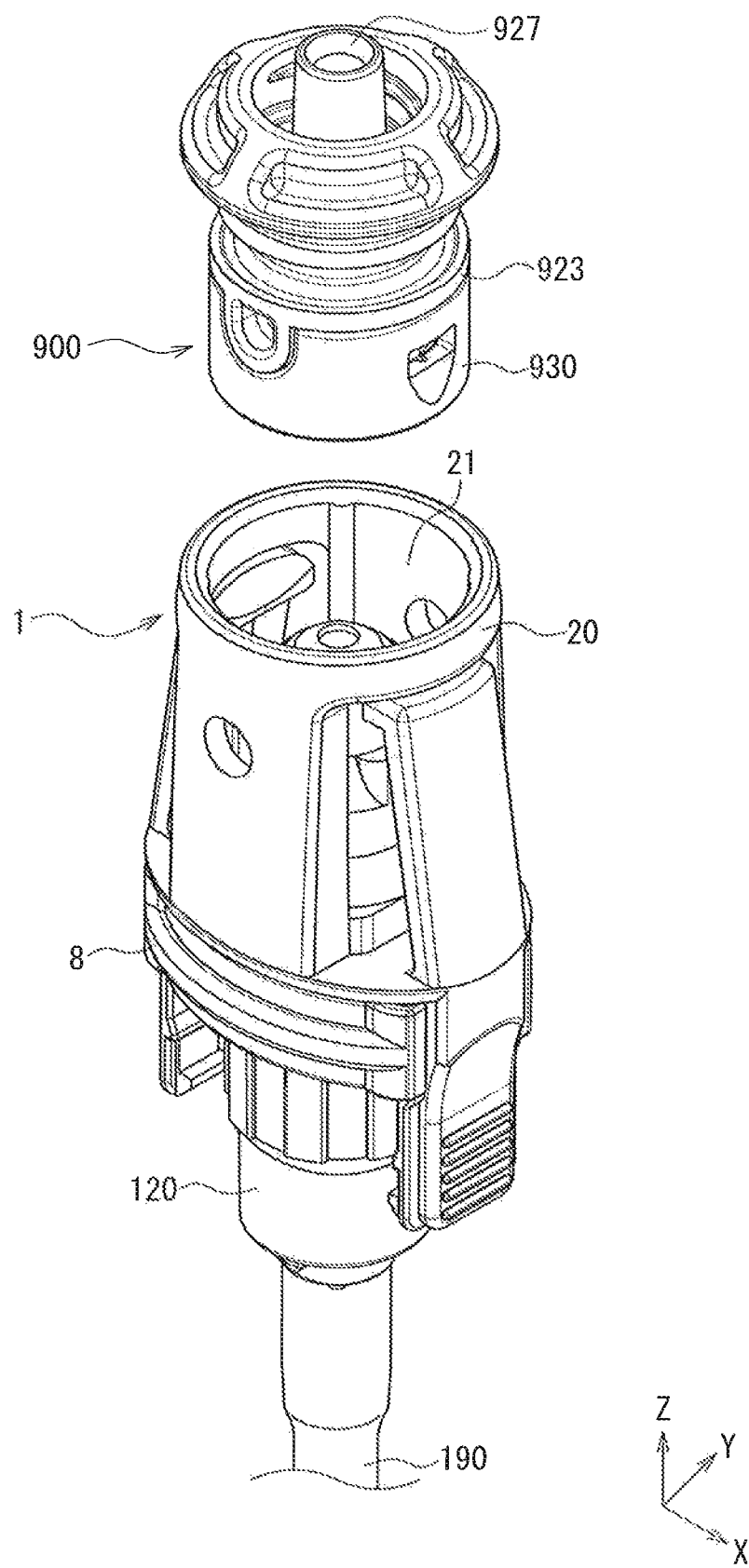
FIG. 11 is a perspective view of the male connector assembly according to Embodiment 1 of the present invention immediately prior to being connected to the female connector.

First, as shown in FIG. 11, the male connector assembly 1 and the female connector 900 are coaxially placed opposing each other. Although not shown in the drawings, a flexible tube is connected to the male luer 927 of the female connector 900 directly or indirectly via a certain member.

From the state shown in FIG. 11, the female connector 900 and the male connector assembly 1 are brought close to each other. The cap 930 of the female connector 900 is inserted into the hood 20 and pushed further inward toward the base 15.

An outer end edge 930a (see FIGS. 10A and 10B) of the top plate 931 of the cap 930 abuts against the inclined surfaces 32a (see FIGS. 2F, 5A, and 5C) of the locking claws 32 of the levers 30. While sliding on the inclined surfaces 32a, the end edge 930a elastically displaces the levers 30 so as to move the locking claws 32 away from the male luer 10. Subsequently, the locking claws 32 slide on the peripheral wall 935 of the cap 930.

In parallel with this, the leading end 10a (see FIG. 9B) of the male luer 10 abuts against the septum 910 (see FIGS. 10A and 10B) that is exposed in the opening 932 of the cap 930, and subsequently advances into the slit 911 while deforming the septum 910. Almost simultaneously, the head portion 61 of the shield 6 abuts against the septum 910 or the top plate 931 of the cap 930. As the male luer 10 advances further into the septum 910, the shield 6 is compressed in the vertical direction, and the outer circumferential wall 65 deforms such that its vertical dimension is reduced.

Figure 12:
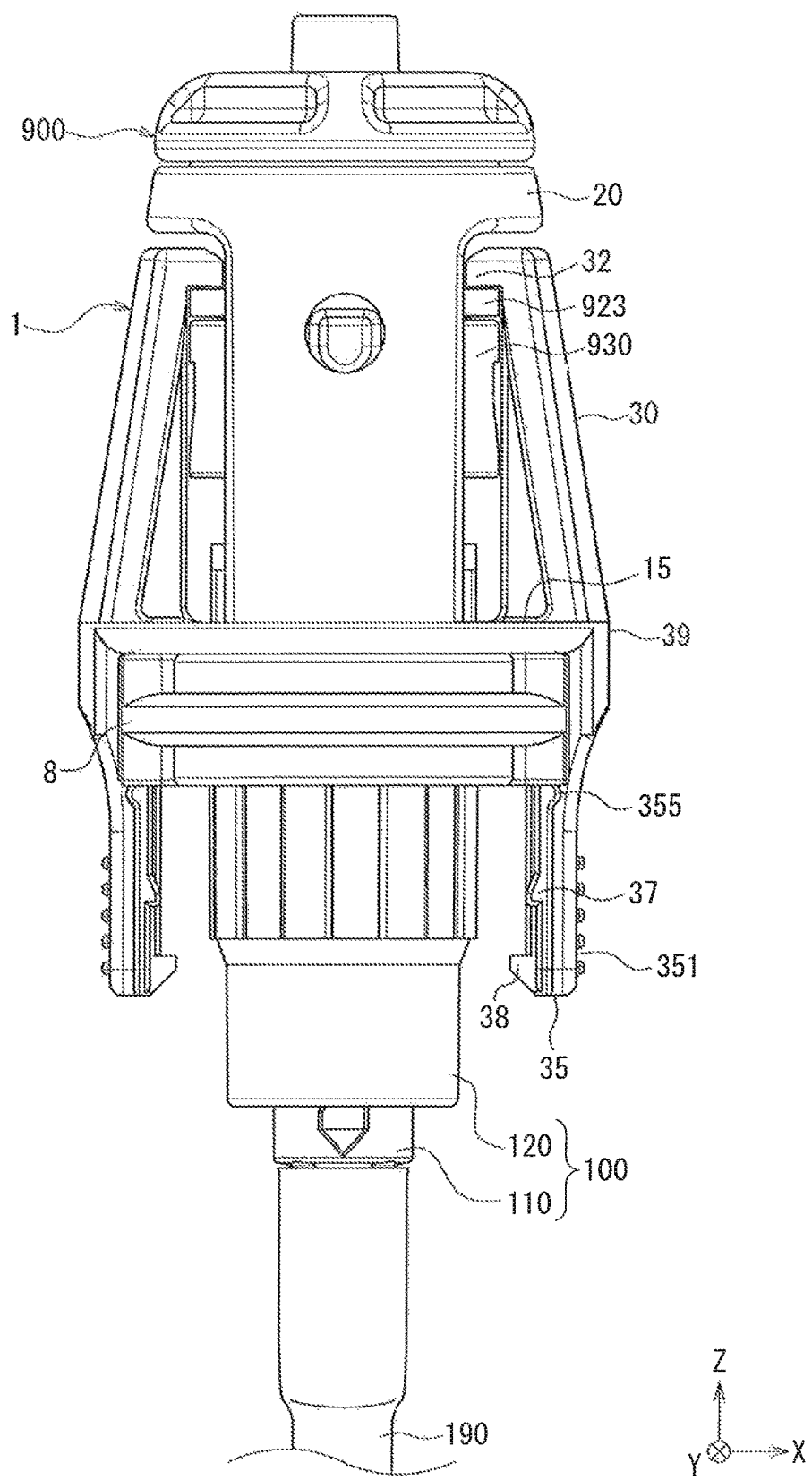
FIG. 12 is a perspective view of the male connector assembly according to Embodiment 1 of the present invention in which locking claws of levers are engaged with the female connector and the lock ring is at a highest position.

The locking claws 32 of the levers 30 slide on the annular projection 923 after sliding on the peripheral wall 935 of the cap 930. When the locking claws 32 have passed the annular projection 923, the base 15 of the connector main body 3 elastically recovers, and the locking claws 32 are engaged with the annular projection 923 (locked state). FIG. 12 is a side view showing this state. The positions of the levers 30 and the lock ring 8 are the same as those in the initial state shown in FIGS. 5A and 9A.

Subsequently, the lock ring 8 is moved downward until it collides with the stopping projections 38 provided on the respective operating portions 35. The locking projections 37 are provided above the stopping projections 38, on the inner surfaces of the respective operating portions 35 (see FIG. 5B). In the process of moving the lock ring 8 downward, the bridging portions 88 move over the locking projections 37. When the bridging portions 88 pass over the locking projections 37, the bridging portions 88 elastically and slightly displaces the operating portions 35 outward (in the direction away from the central axis 3a). After the bridging portions 88 have passed over the locking projections 37, the operating portions 35 elastically recover. When the bridging portions 88 pass over the locking projections 37, the force for moving the lock ring 8 changes. An operator can feel a change in the force at the time when the bridging portions 88 finish passing over the locking projections 37 as a clicking sensation and thus recognize that the lock ring 8 has reached its lowest position (second position).

Figure 13A:
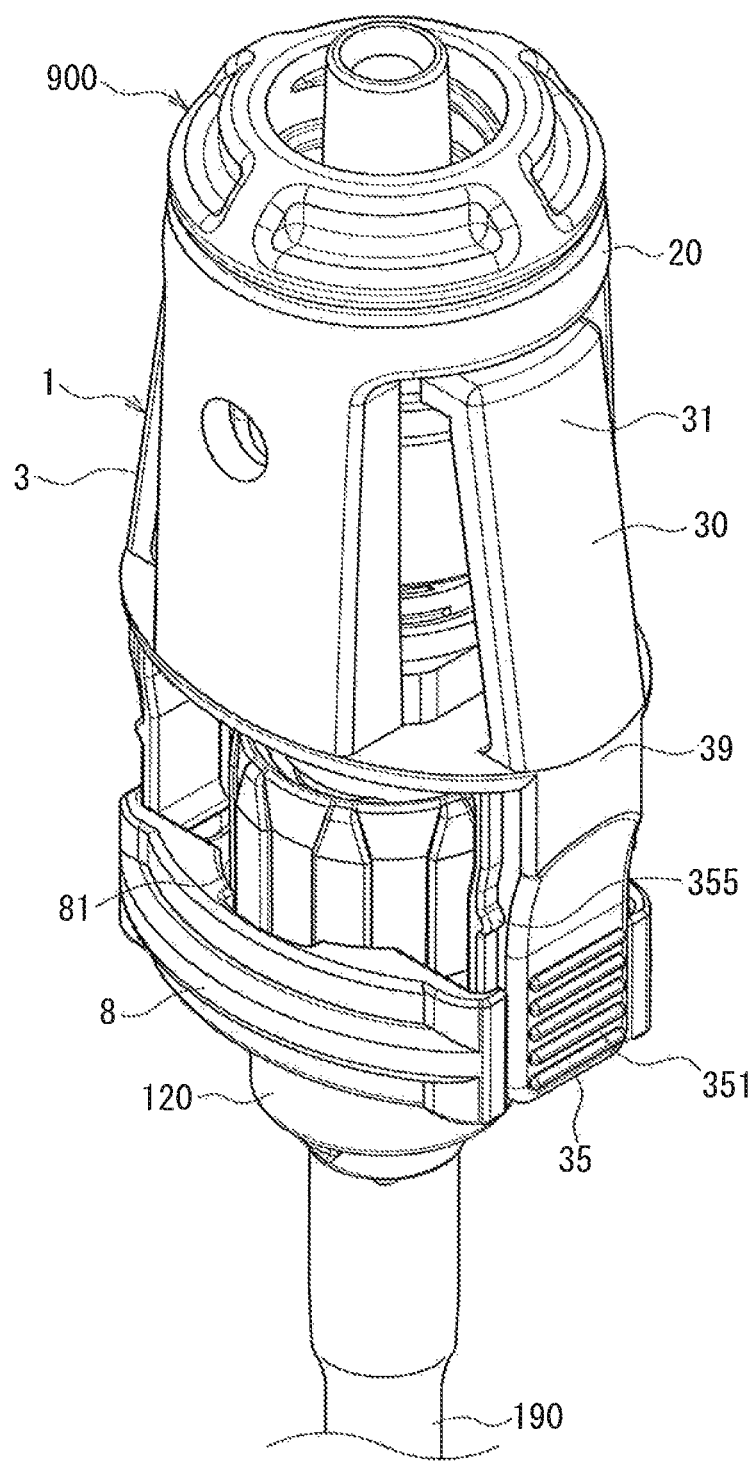
FIG. 13A is a perspective view of the male connector assembly according to Embodiment 1 of the present invention after the connection to the female connector has been completed.
Figure 13C:
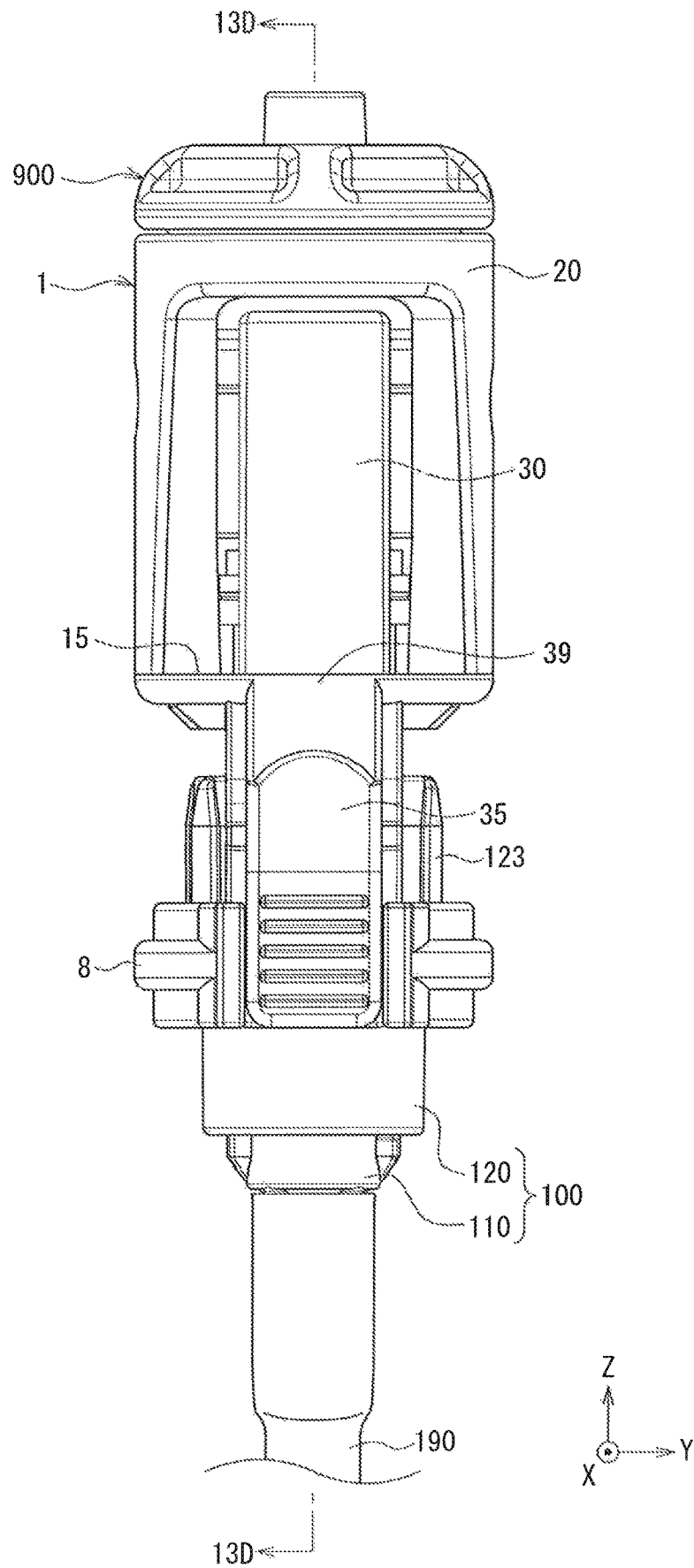
FIG. 13C is a side view of the male connector assembly in FIG. 13.
Figure 13D:
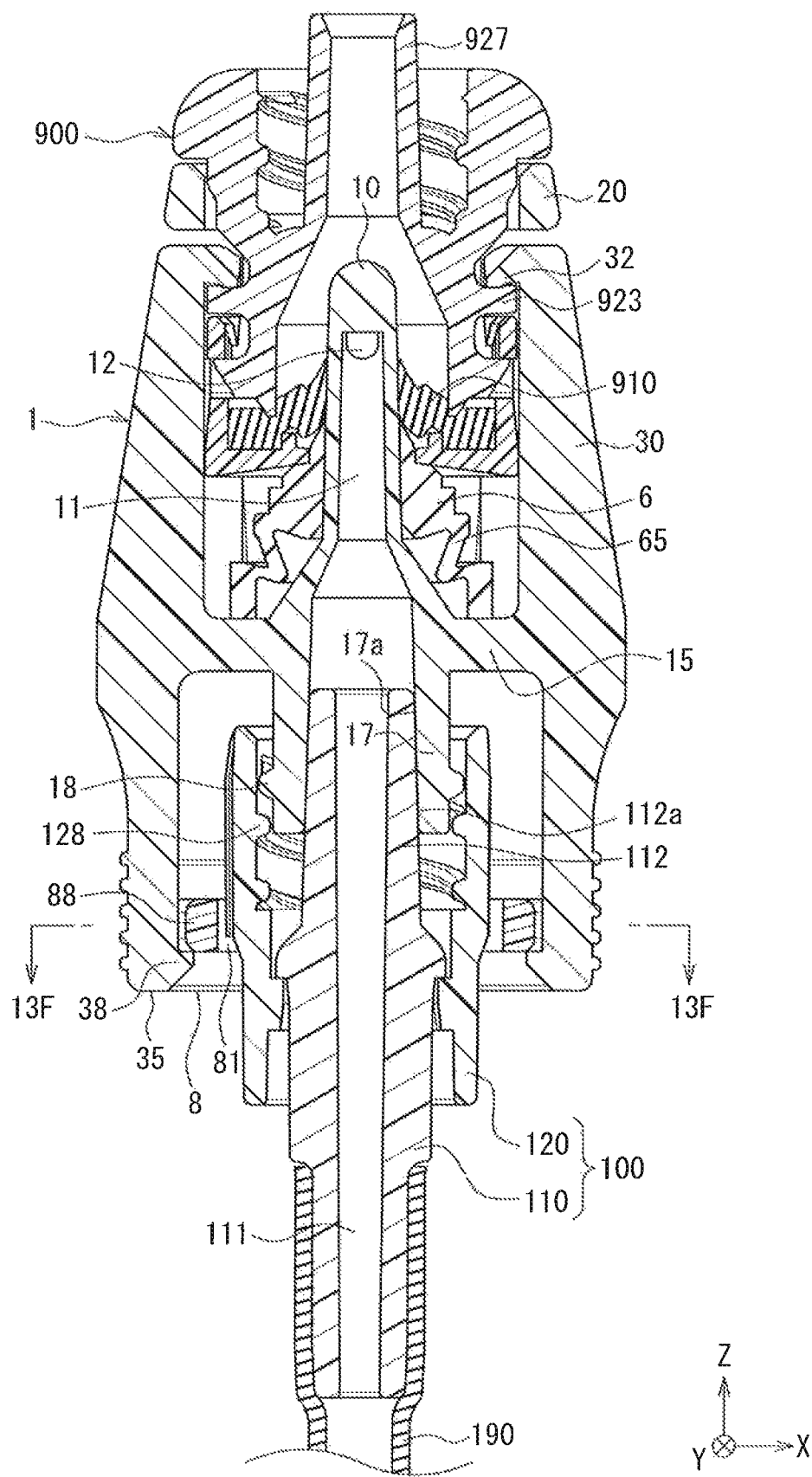
FIG. 13D is a cross-sectional view taken along a plane containing line 13D-13D in FIG. 13C and seen in the direction of the arrows.

FIGS. 13A, 13B, and 13C are a perspective view, a front view, and a side view, respectively, that show a state in which the lock ring 8 has been moved to its lowest position. FIG. 13D is a cross-sectional view taken along a plane containing line 13D-13D in FIG. 13C and seen in the direction of the arrows. FIG. 13E is a cross-sectional view taken along a plane containing line 13E-13E in FIG. 13B and seen in the direction of the arrows. FIG. 13F is a cross-sectional view taken along a plane containing line 13F-13F in FIG. 13D and seen in the direction of the arrows.

Figure 13E:
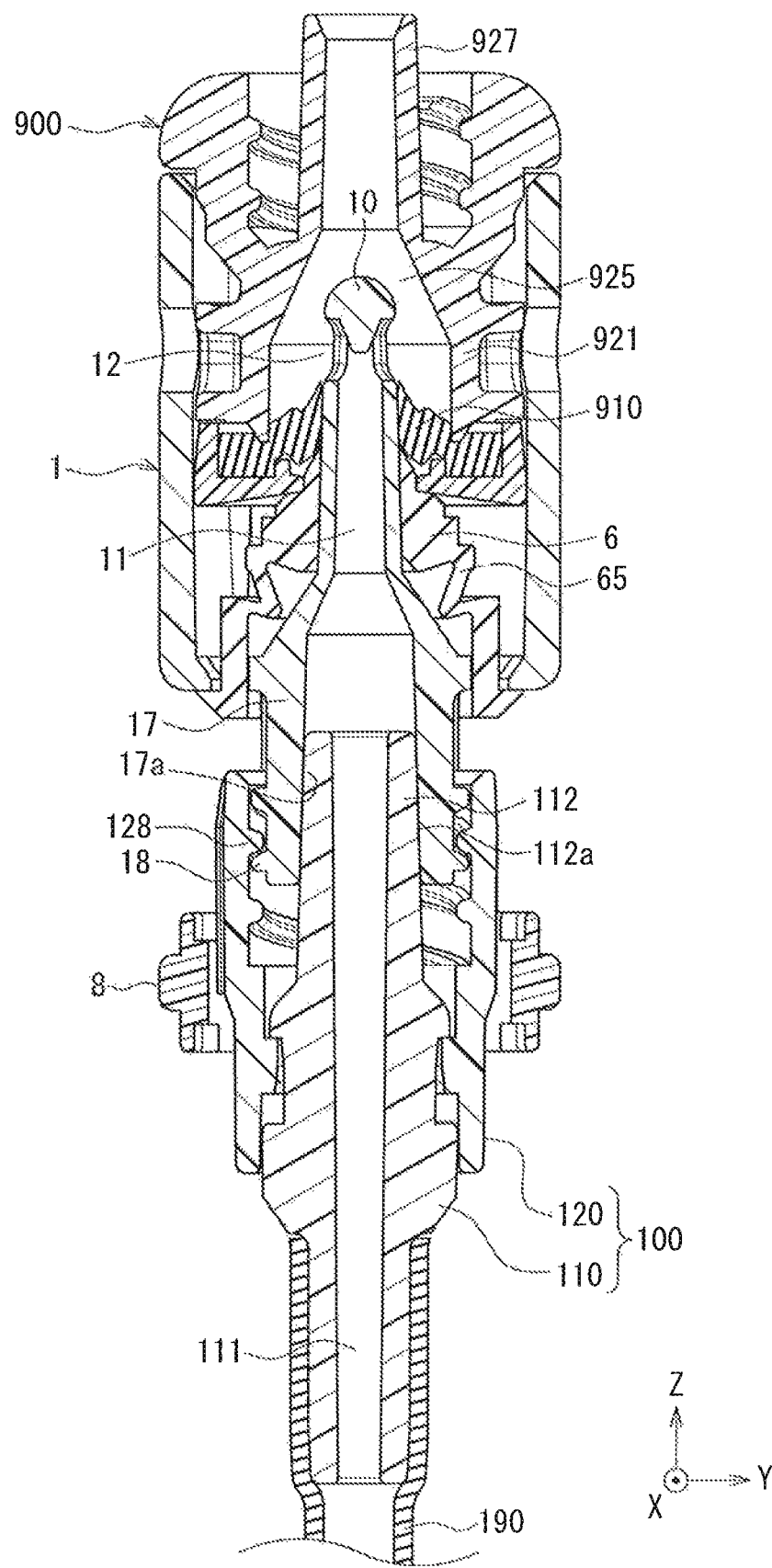
FIG. 13E is a cross-sectional view taken along a plane containing line 13E-13E in FIG. 13B and seen in the direction of the arrows.
Figure 13F:
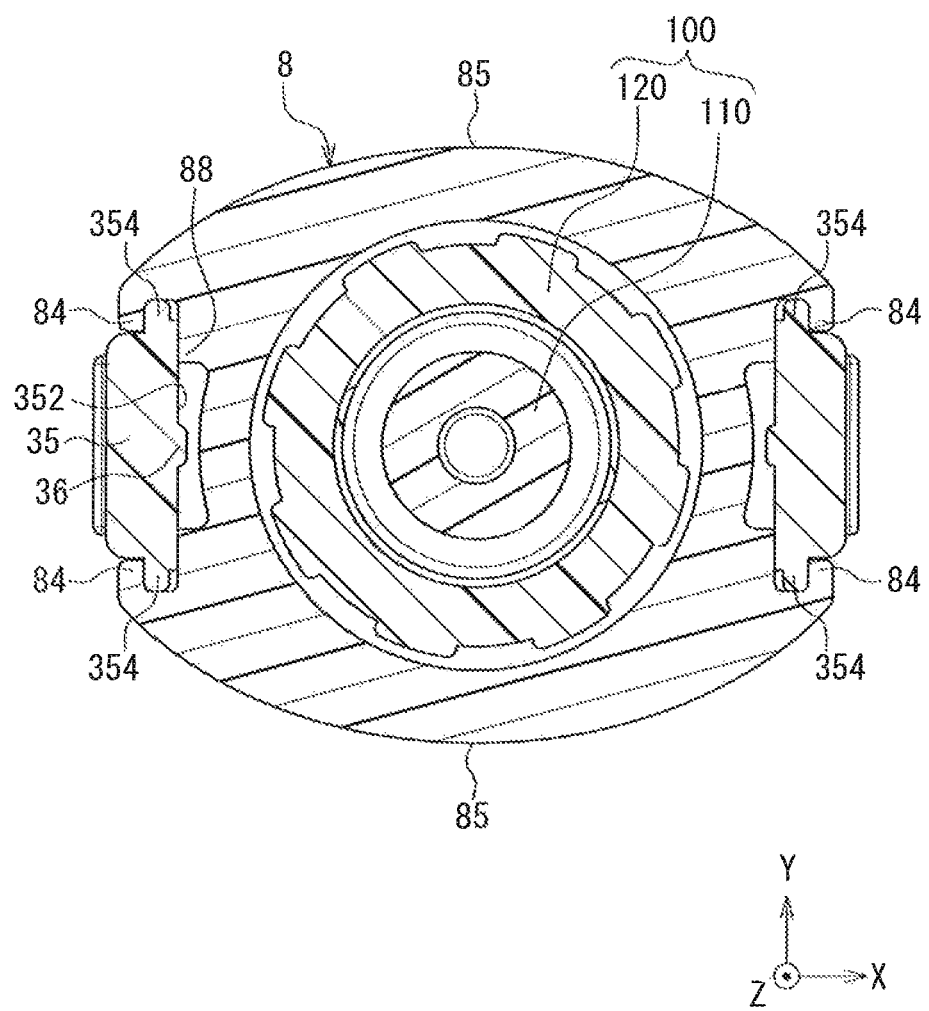
FIG. 13F is a cross-sectional view taken along a plane containing line 13F-13F in FIG. 13D and seen in the direction of the arrows.

As shown in FIG. 13E, the male luer 10 penetrates the slit 911 (see FIGS. 10A and 10B) of the septum 910, and thus, the septum 910 deforms toward the cavity 925 of the seat 921. The openings of the lateral holes 12 of the male luer 10 are exposed in the cavity 925 of the seat 921. Therefore, the flow channel 11 of the male luer 10 and the cavity 925 of the seat 921 are in communication with each other. In this state, a liquid is allowed to flow from the tube 190 to the flow channel 111 of the luer main body 110, the flow channel 11 of the male luer 10, the cavity 925 of the seat 921, and the male luer 927, or in the reverse direction.

The shield 6 receives the compressive force in the vertical direction. In particular, the outer circumferential wall 65 of the shield 6 deforms such that its vertical dimension is reduced.

As shown in FIGS. 13A and 13B, when the lock ring 8 is at its lowest position, the lock nut 120 is disposed in the opening 81 (see FIGS. 4A and 4B) of the lock ring 8. In other words, the outer circumferential surface of the lock nut 120 is surrounded by the lock ring 8. The ribs 123 of the lock nut 120 are located at substantially the same height as or above the lock ring 8. The lock nut 120 makes it difficult to touch the ribs 123, which are convenient for rotating the lock ring 8, with a finger. For this reason, the likelihood of occurrence of an unforeseen situation in which, for example, the patient erroneously rotates the lock nut 120 and loosens the screwed connection between the female thread 128 of the lock nut 120 and the male thread 18 of the tubular portion 17, thereby causing leakage of the liquid from between the outer circumferential surface 112a of the male luer 112 and the inner circumferential surface 17a of the tubular portion 17 or dislodgement of the male luer 112 from the tubular portion 17 is low. In this manner, when moved to the lowest position, the lock ring 8 functions as an "erroneous operation prevention mechanism" that prevents an erroneous operation of erroneously rotating the lock nut 120.

As shown in FIG. 13F, the inner surfaces 352 (in particular, lock regions 352b thereof (see FIG. 2B)) of the operating portions 35 are located close to or abut against the respective bridging portions 88 of the lock ring 8 in the X-axis direction. The gaps 356 (see FIG. 5E) that are present between the inner surfaces 352 of the operating portions 35 and the respective bridging portions 88 of the lock ring 8 when the lock ring 8 is at its highest position substantially disappear when the lock ring 8 is moved to its lowest position. Accordingly, when the lock ring 8 is at its lowest position, even if a force acting toward the tubular portion 17 is applied to the outer surfaces 351 of the operating portions 35, the levers 30 cannot pivot because the inner surfaces 352 of the operating portions 35 abut against the lock ring 8. That is to say, the lock ring 8, when moved to its lowest position, functions as a "lever pivotal movement prevention mechanism" that prevents the levers 30 from pivoting.

Since the levers 30 cannot pivot, the state (locked state, see FIG. 13D) in which the locking claws 32 are engaged with the annular projection 923 cannot be cancelled. For this reason, an unforeseen situation in which the locking claws 32 are disengaged from the annular projection 923 by an unintentional external force acting on the operating portions 35, and the male connector assembly 1 (or the male connector 2) and the female connector 900 are disconnected from each other will not occur.

The lock ring 8 functions as both the "erroneous operation prevention mechanism" for the lock nut 120 and the "lever pivotal movement prevention mechanism" for the levers 30. Thus, compared with a case in which these two mechanisms are constituted by different members, the number of members that constitute the male connector assembly 1 can be reduced, and the configuration of the male connector assembly 1 can be simplified.

When the lock ring 8 is at its highest position (first position, see FIG. 12), both of the mechanisms do not function, and if the lock ring 8 is moved to its lowest position (second position, see FIGS. 13A to 13F), both of the mechanisms function. In this manner, activation and deactivation of the erroneous operation prevention mechanism and the lever pivotal movement prevention mechanism can be simultaneously switched through an extremely simple operation of moving a single member, the lock ring 8, along the central axis 3a.

As shown in FIG. 13D, when the lock ring 8 is at its lowest position, the stopping projections 38 are located close to or abut against the bridging portions 88 of the lock ring 8. Therefore, the stopping projections 38 prevent the lock ring 8 from being dislodged downward from between the operating portions 35.

Although not shown in the drawings, when the lock ring 8 is at its lowest position, the locking projections 37 (see FIG. 5B) are located directly above the bridging portions 88, and each bridging portion 88 and a corresponding one of the locking projections 37 are located close to or abut against each other in the vertical direction. For this reason, the lock ring 8 is prevented from being unintentionally moved upward from the lowest position due to vibrations, an external force, and the like. That is to say, the locking projections (second locking projections) 37 constitute a "second movement prevention mechanism" that prevents the lock ring 8 at its lowest position from being unintentionally moved upward. The lock ring 8 is held at its lowest position, and thus, the likelihood of the state in which the erroneous operation prevention mechanism and the lever pivotal movement prevention mechanism are activated being unintentionally cancelled is reduced.

Briefly, the male connector assembly 1 and the female connector 900 can be disconnected from each other by performing the above-described procedures in reverse order.

That is to say, in the state shown in FIGS. 13A to 13F, the lock ring 8 is moved upward until it collides with the lower surface of the base 15, that is, until it reaches its highest position (first position, see FIG. 12). In the process of moving the lock ring 8 to the highest position, it is necessary for the claws 84 of the lock ring 8 to move over the respective locking projections (first locking projections) 355 protruding from the sliding ribs 354. When the claws 84 pass over the respective locking projections 355, the force for moving the lock ring 8 changes. The operator can feel a change in force when the claws 84 finish passing over the locking projections 355 as a clicking sensation, and thus can recognize that the lock ring 8 has reached its highest position (first position).

When the lock ring 8 has been moved to its highest position, the gaps 356 are formed between the inner surfaces 352 of the operating portions 35 and the respective bridging portions 88 of the lock ring 8 (see FIG. 5E). In the state in which the lock ring 8 is at its highest position, an external force is applied to the outer surfaces 351 of the operating portions 35 to cause the levers 30 to pivot, and thus, the locking claws 32 are disengaged from the annular projection 923. Subsequently, in the state in which the levers 30 have pivoted, the male connector assembly 1 and the female connector 900 are pulled apart from each other, and thus, the male connector assembly 1 and the female connector 900 can be disconnected from each other (see FIG. 11). The septum 910 elastically recovers immediately after the removal of the male luer 10, and thus, the slit 911 is closed. The shield 6 expands due to the elastic recovery force it has, and the inner circumferential surface of the head portion 62 closes the openings of the lateral holes 12 of the male luer 10. If the external force applied to the operating portions 35 is released, the levers 30 elastically return to the initial state.

Furthermore, if necessary, the female thread 128 and the male thread 18 may be unscrewed by rotating the lock nut 120, and then, the male connector 2 and the screw lock-type connector 100 may be disconnected from each other.

5. Effects

In the male connector assembly 1 of Embodiment 1, the levers 30 including the locking claws 32 function as the "lever-type lock mechanism" for maintaining (locking) the state in which the male connector assembly 1 is connected to the female connector 900. In order to connect the male connector assembly 1 to the female connector 900, it is only necessary to insert the female connector 900 into the opening 21 of the hood 20 and push the female connector 900 further into the male connector assembly 1. Since the locking claws 32 are provided with the inclined surfaces 32*a*, when the female connector 900 is advanced into the hood 20, the levers 30 pivot. Afterward, when the female connector 900 has been inserted to a predetermined depth into the hood 20, the levers 30 return to their initial positions, and the locking claws 32 are engaged with the female connector 900. The engagement of the locking claws 32 with the female connector 900 (locked state) can be easily confirmed based on changes in the positions of the levers 30 (in particular, the locking portions 31) with respect to the radial direction, and furthermore, based on a "click" sound that is produced when the locking claws 32 are engaged with the female connector 900 and the levers 30 return to their initial positions. Since the end edge of the opening 21 of the hood 20 positions the female connector 900 with respect to the horizontal direction, a stable engagement operation can be performed at any time. The operator is not required to touch the levers 30 in order to engage the locking claws 32 with the female connector 900.

Moreover, the locking claws 32 can be disengaged from the female connector 900 simply by pressing the outer surfaces 351 of the operating portions 35 and slightly pivoting the levers 30.

As described above, the male connector assembly 1 of Embodiment 1 including the lever-type lock mechanism provides excellent ease of operations for connecting and disconnecting the male connector assembly 1 to and from the female connector 900.

The male connector assembly 1 includes the lock ring 8 that is disposed opposing the inner surfaces 352 of the operating portions 35 in the X-axis direction. The lock ring 8 is movable in the vertical direction between the highest position (first position) at which it is located close to the base 15 and the lowest position (second position) at which it is located away from the base 15.

When the lock ring 8 is at its lowest position (second position), the levers 30 are restricted from pivoting by the operating portions 35 colliding with the lock ring 8 (in particular, bridging portions 88 thereof) (see FIG. 13F). Thus, even if an external force acts on the operating portions 35 when, for example, the male connector assembly 1 collides with an object therearound or the male connector assembly 1 is pinned under the patient's body, it is unlikely that the state (locked state) in which the locking claws 32 are engaged with the female connector 900 will be unintentionally cancelled.

As described above, the male connector assembly 1 of Embodiment 1 includes a double lock mechanism that has, in addition to the lever-type lock mechanism (first lock mechanism) for maintaining a state in which the male connector assembly 1 is connected to the female connector 900, the lock ring 8 (second lock mechanism) for maintaining the locked state that is maintained by the lever-type lock mechanism. Thus, the likelihood of the locked state that is maintained by the lever-type lock mechanism (first lock mechanism) being unintentionally cancelled is reduced.

It should be noted that, when the lock ring 8 is at its lowest position, it is not necessary that the operating portions 35 are in contact with the bridging portions 88 of the lock ring 8 as shown in FIG. 13F. As long as the levers 30 are restricted from pivoting so as not to allow the engagement of the locking claws 32 with the female connector 900 to be released, the operating portions 35 may be slightly spaced apart from the respective bridging portions 88 in the X-axis direction.

On the other hand, when the lock ring 8 is at its highest position (first position), the operating portions 35 are spaced apart from the lock ring 8 in the X-axis direction (see FIG. 5E). Thus, the locking claws 32 can be engaged with or disengaged from the female connector 900 by pivoting the levers 30 without the operating portions 35 colliding with the lock ring 8. Accordingly, the ease of operations for connecting and disconnecting the male connector assembly 1 and the female connector 900 is further improved.

When the female connector 900 is inserted into the opening 21 of the hood 20, and the female connector 900 collides with the locking claws 32, the levers 30 pivot, and when the female connector 900 is inserted further into the hood 20 toward the base 15, the locking claws 32 engage with the female connector 900, and the levers 30 return to their initial positions. Preferably, in a state after the collision of the locking claws 32 with the female connector 900 and prior to the engagement of the locking claws 32 with the female connector 900, in which the levers 30 have pivoted, the lock ring 8 cannot be moved from the highest position to the lowest position. This is because the bridging portions 88 of the lock ring 8 collide with the respective inner surfaces 352 of the operating portions 35 of the levers 30 that have pivoted. Accordingly, for example, even if the operator is under the illusion that engagement of the locking claws 32 with the female connector 900 has been completed despite the fact that the engagement is insufficient and attempts to move the lock ring 8 from the highest position to the lowest position, the lock ring 8 cannot be moved to the lowest position. Thus, the operator can recognize that the locking claws 32 have not correctly engaged with the female connector 900. Therefore, the likelihood of the operator performing an erroneous operation of starting to pass the liquid between the male connector assembly 1 and the female connector 900 without being aware that the locking claws 32 are not engaged with the female connector 900, and the occurrence of unintentional disconnection of the male connector assembly 1 and the female connector 900 can be reduced.

In the case where the connector main body 3 includes a plurality of levers 30 as in Embodiment 1, when the female connector 900 is inserted into the hood 20 in a state in which the female connector 900 is inclined relative to the central axis 3*a*, a state (so-called "unevenly engaged state") in which only the locking claw 32 of a certain lever 30 of the plurality of levers 30 is engaged with the female connector 900 while the locking claw 32 of the other lever 30 is not engaged with the female connector 900 may occur. The configuration in which the lock ring 8 cannot be moved to the lowest position unless the levers 30 have returned to their initial positions enables the operator to easily become aware of the above-described unevenly engaged state.

It should be noted that, if engagement of the locking claws 32 with the female connector 900 is insufficient, the engagement may be adjusted so that the locking claws 32 are correctly engaged with the female connector 900, due to the bridging portions 88 of the lock ring 8 colliding with the inner surfaces 352 of the operating portions 35 in the process of moving the lock ring 8 from the highest position to the lowest position.

As described above, according to Embodiment 1, the lock ring 8 can be moved to the lowest position only when the locking claws 32 are correctly engaged with the female connector 900. In other words, if the lock ring 8 can be moved to the lowest position, it is certain that the locking claws 32 are correctly engaged with the female connector 900. Thus, the operator can recognize that the locking claws 32 are engaged with the female connector 900 based on the fact that the operator has moved the lock ring 8 to the lowest position. This is advantageous in improving the reliability of the state of being connected to the female connector 900.

In Embodiment 1, the horizontal dimensions of the connector main body 3 and the male connector 2 are largest in the direction in which the male luer 10 opposes the levers 30. More specifically, the outlines (or projected shapes of the connector main body 3 and the male connector 2) of the connector main body 3 and the male connector 2 when viewed from above are substantially elliptical shapes having the major axis 15*a* in the direction in which the male luer 10 opposes the levers 30 (FIG. 2E). The lock ring 8 does not protrude outward from the above-described outline of the connector main body 3. A leading end portion (i.e., the cap 930) of the female connector 900 is housed in the hood 20. Therefore, if the male connector assembly 1 is pinned under the patient with the central axis 3*a* extending in the horizontal direction, the male connector assembly 1 can easily rotate so that the direction of the major axis 15*a* becomes the horizontal direction, and the likelihood of the weight of the patient acting on the male connector assembly 1 along the direction of the major axis 15*a* is low. Therefore, the patient is unlikely to feel pain due to the male connector assembly 1 or even develop a decubitus ulcer as a result of the male connector assembly 1 continuously pressing the skin or soft tissue of the patient. Moreover, since the likelihood of the weight of the patient acting on the operating portions 35 is low, even if the operator forgets to move the lock ring 8 to the lowest position, the likelihood of the state (locked state) in which the locking claws 32 of the levers 30 are engaged with the female connector 900 being unintentionally cancelled is low compared with that of a male connector provided with a conventional lever-type lock mechanism.

Furthermore, the operating portions 35 of the levers 30 are set back toward the central axis 3*a* from the lever base portions 39. Therefore, if the male connector assembly 1 is pinned under the patient, the likelihood of the weight of the patient being applied to the operating portions 35 of the levers 30 along the direction of the major axis 15*a* is even lower.

Moreover, an external force that is applied to the male connector assembly 1 when the male connector assembly 1 collides with a member therearound or the male connector assembly 1 is pinned under the patient's body is highly likely to be applied to the lever base portions 39, which protrude furthest outward. The likelihood of the above-described external force being applied to the operating portions 35, which are set back toward the central axis 3*a* from the lever base portions 39, is low.

As described above, since the lever base portions 39 protrude furthest outward in the radial direction, and the operating portions 35 are located nearer to the central axis 3*a* than the lever base portions 39, even if the operator forgets to move the lock ring 8 to the lowest position, the likelihood of the state (locked state) in which the locking claws 32 of the levers 30 are engaged with the female connector 900 being unintentionally cancelled is even lower.

The lock ring 8 is disposed so as to oppose the inner surfaces 352 of the operating portions 35. Thus, the lock ring 8 that does not protrude from the substantially elliptical outline of the connector main body 3 when viewed from above can be easily realized. If the male connector assembly 1 is pinned under the patient, this configuration is advantageous in rotating the male connector assembly 1 so that the direction of the major axis 15*a* becomes the horizontal direction. Also, if the male connector assembly 1 is pinned under the patient, this configuration is advantageous in reducing the patient's pain that is caused by the lock ring 8. Furthermore, this configuration is advantageous in simplifying the configuration of the lock ring 8, which functions as the lever pivotal movement prevention mechanism that prevents the levers 30 from pivoting, and also improving the reliability of the operation of the lock ring 8.

In Embodiment 1, the leading end 20*a* of the hood 20 has a circular shape that is coaxial with the central axis 3*a*. The external diameter of the hood 20 at the leading end 20*a* of the hood 20 is approximately the same as the diameter (minor diameter) of the substantially elliptical outline of the connector main body 3 in the direction of the minor axis 15*b*. As described above, the external dimension of the hood 20 at the leading end 20*a* is set at the minimum dimension that is necessary for housing the female connector 900 and positioning the female connector 900 with respect to the horizontal direction. Thus, the size of the male connector assembly 1 (in particular, the connector main body 3) can be reduced. This is advantageous in reducing the patient's pain caused by the male connector assembly 1 if the male connector assembly 1 is pinned under the patient.

In Embodiment 1, the portions of the male connector assembly 1 that protrude furthest from the central axis 3*a* in the radial direction are the lever base portions 39 (see FIG. 13B). The male connector assembly 1 has the largest horizontal dimension at the position of the lever base portions 39 (or the base 15). The locking portions 31 of the levers 30 are inclined such that the distance from the central axis 3*a* decreases as the distance from the lever base portions 39 increases. Thus, a smooth curved surface in which the outer surfaces of the locking portions 31 are continuous with the outer surface of the hood 20 can be formed in the male connector assembly 1 (in particular, the connector main body 3). This is advantageous in improving the design value of the male connector assembly 1. Also, this is advantageous in reducing the patient's pain caused by the male connector assembly 1 if the male connector assembly 1 is pinned under the patient.

The shield 6 is attached to the male luer 10. When the male connector assembly 1 is not connected to the female connector 900, the shield 6 closes the openings of the lateral holes 12 that are provided in the male luer 10 and that are in communication with the flow channel 11. Thus, when the male connector assembly 1 is not connected to the female connector 900, the liquid can be prevented from leaking to the outside through the lateral holes 12. Therefore, the shield 6 functions as a safety mechanism (fail-safe mechanism) that prevents the liquid from leaking even if all of the above-described various mechanisms that prevent unintentional cancellation of the connection between the male connector assembly 1 and the female connector 900 do not function.

Embodiment 2

Embodiment 2 of the present invention differs from Embodiment 1 mainly in the configurations of the connector main body and the lock ring. Hereinafter, Embodiment 2 will be described focusing on the differences from Embodiment 1.

1. Connector Main Body

Figure 14A:
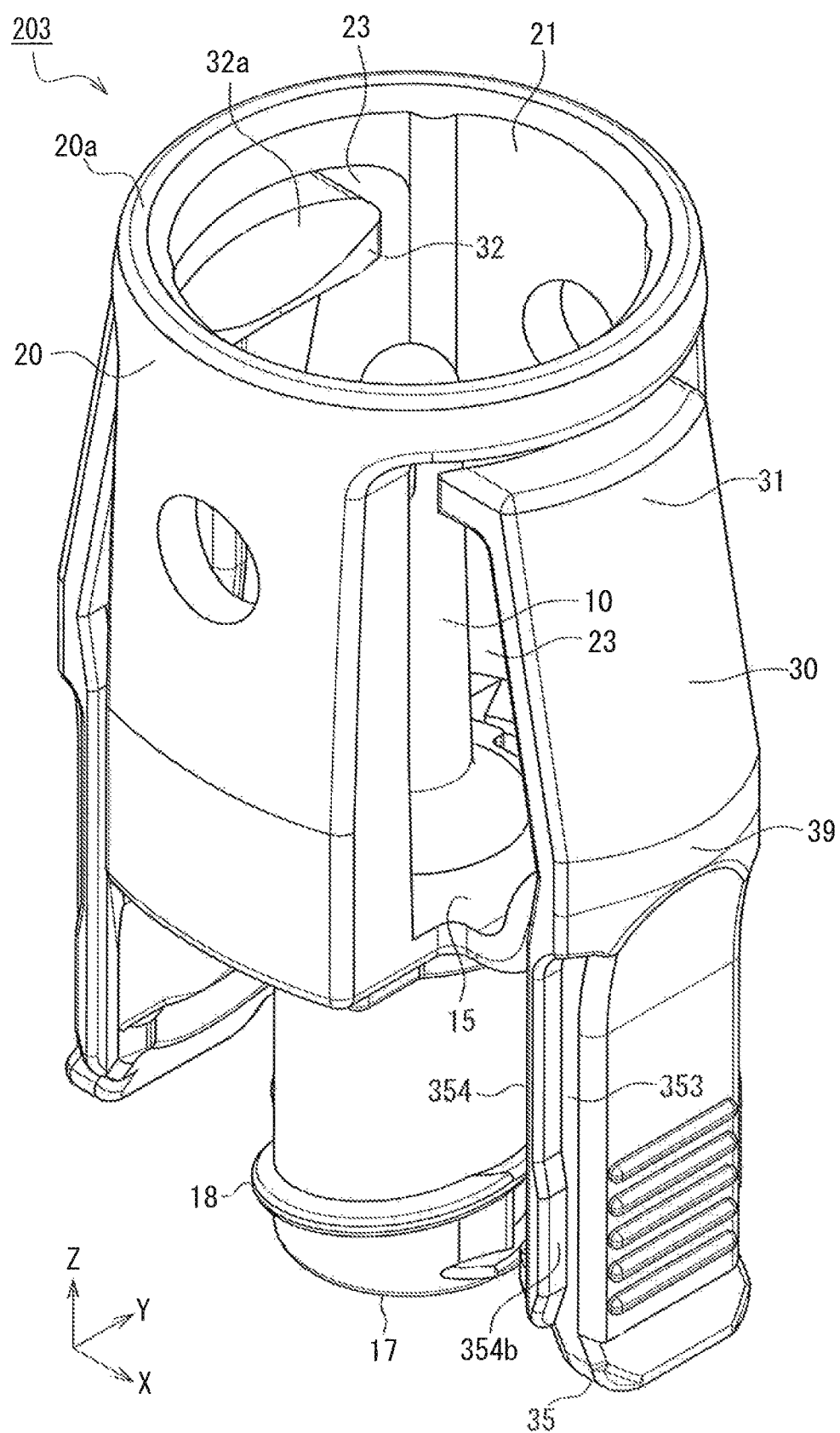
FIG. 14A is a perspective view of a connector main body according to Embodiment 2 of the present invention when viewed from above.
Figure 14B:
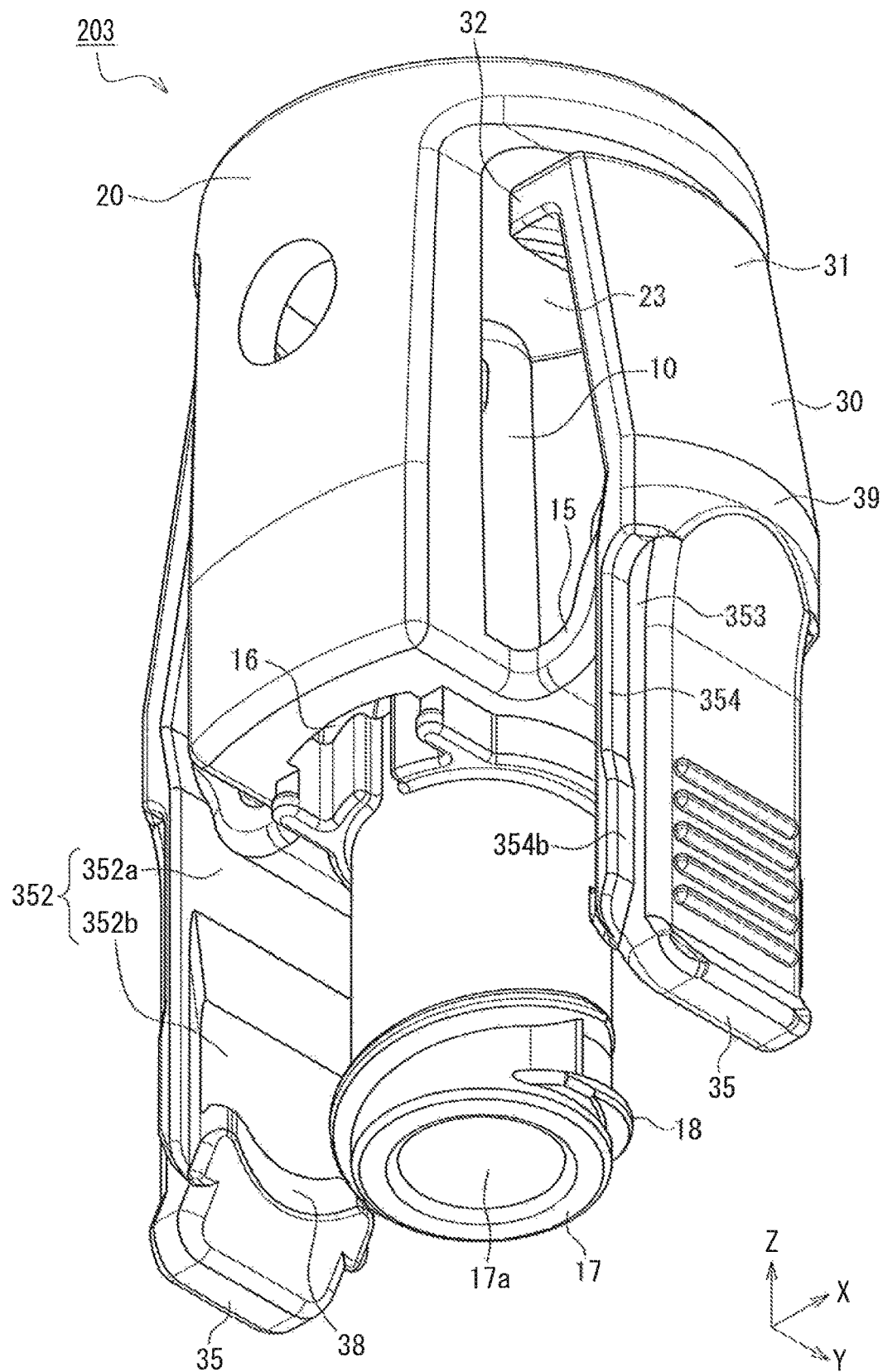
FIG. 14B is a perspective view of the connector main body according to Embodiment 2 of the present invention when viewed from below.
Figure 14C:
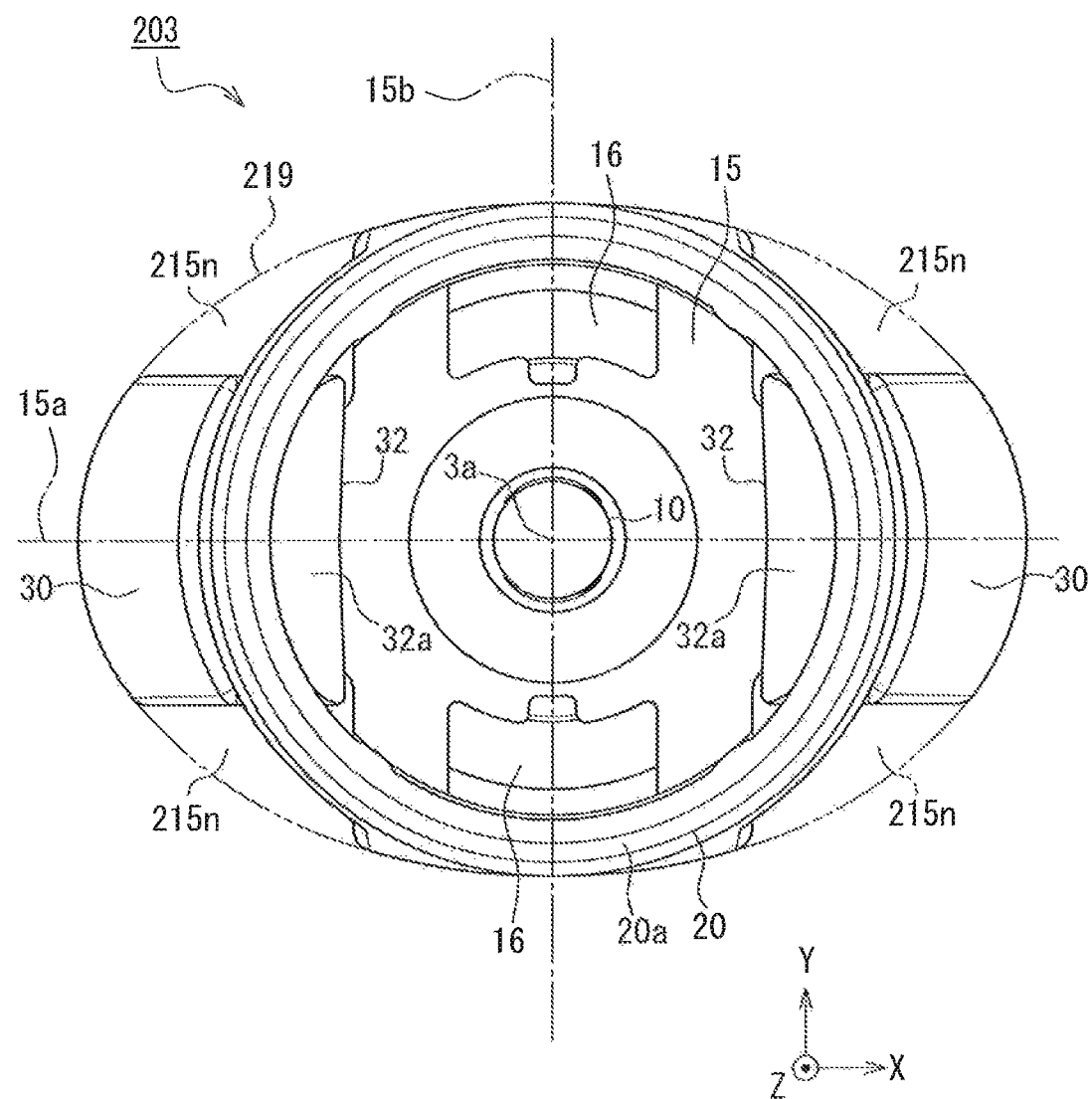
FIG. 14C is a plan view of the connector main body according to Embodiment 2 of the present invention.

FIG. 14A is a perspective view of a connector main body 203 according to Embodiment 2 when viewed from above, FIG. 14B is a perspective view of the connector main body 203 when viewed from below, and FIG. 14C is a plan view of the connector main body 203. In FIGS. 14A to 14C, members corresponding to the members shown in FIGS. 2A to 2G are denoted by the same reference numerals as those in FIGS. 2A to 2G.

As can be easily understood by comparison of FIG. 14C with FIG. 2E, four cut-outs 215$n$ are provided in the base 15 of the connector main body 203. The cut-outs 215$n$ are provided in regions of the outer end edge of the base 15 other than the portions (portions on the major axis 15$a$ and portions on the minor axis 15$b$) where the levers 30 and the hood 20 are provided. When viewed from above (in plan view) along the central axis 3$a$, the base 15 is substantially cross-shaped. The outline of the connector main body 203 in plan view is recessed at the cut-outs 215$n$. The external dimension of the connector main body 203 in plan view is largest in the direction (direction of the major axis 15$a$) in which the male luer 10 opposes the levers 30. The outline of the connector main body 203 excluding the cut-outs 215$n$ conforms to an ellipse 219 indicated by the long dashed double-short dashed line. The ellipse 219 has the major axis 15$a$ and the minor axis 15$b$ that are orthogonal to each other. The cut-outs 215$n$ are advantageous in facilitating the pivotal movement of the levers 30 while securely coupling the hood 20 to the male luer 10 via the base 15.

As shown in FIGS. 14A and 14B, the base 15 of the connector main body 203 is not a flat plate in the strict sense of the word. The base 15 has a stepped shape (or an inclined shape) such that portions near the levers 30 are located above portions near the male luer 10. This stepped shape (or inclined shape) increases the creepage distance from the male luer 10 to each lever 30 along the surface of the base 15 without changing the external dimension of the connector main body 203 in the direction of the major axis 15$a$. This is advantageous in facilitating the pivotal movement of the levers 30 because regions of the base 15 that can be elastically deformed and bent are expanded. However, the stepped shape (or inclined shape) is not indispensable to Embodiment 2. The base 15 of Embodiment 2 may also be constituted by a flat plate-shaped member that is parallel to the horizontal direction, similar to that of Embodiment 1.

As shown in FIGS. 14A and 14B, the sliding ribs 354 protrude in the Y-axis direction from the side surfaces (surfaces that are parallel to the XZ plane) 353 of the operating portions 35. The sliding ribs 354 extend substantially in the vertical direction from the base 15 to the lower ends of the operating portions 35. In Embodiment 1, the pressure contact portions 354$a$ are provided in regions near the base 15 of the sliding ribs 354 (see FIGS. 2A and 2B). In contrast, in Embodiment 2, instead of the pressure contact portions 354$a$, pressure contact portions 354$b$ are provided in regions near the lower ends of the sliding ribs 354, the pressure contact portions 354$b$ being formed by the outer surfaces (surfaces that face away from the tubular portion 17) of the sliding ribs 354 slightly protruding.

As shown in FIG. 14B, the recessed region 352$a$ and the lock region 352$b$ are provided on the inner surface 352 of each operating portion 35 as in Embodiment 1. However, the locking projections 37 (see FIG. 2B) provided in Embodiment 1 are not provided in Embodiment 2.

2. Lock Ring

Figure 15A:
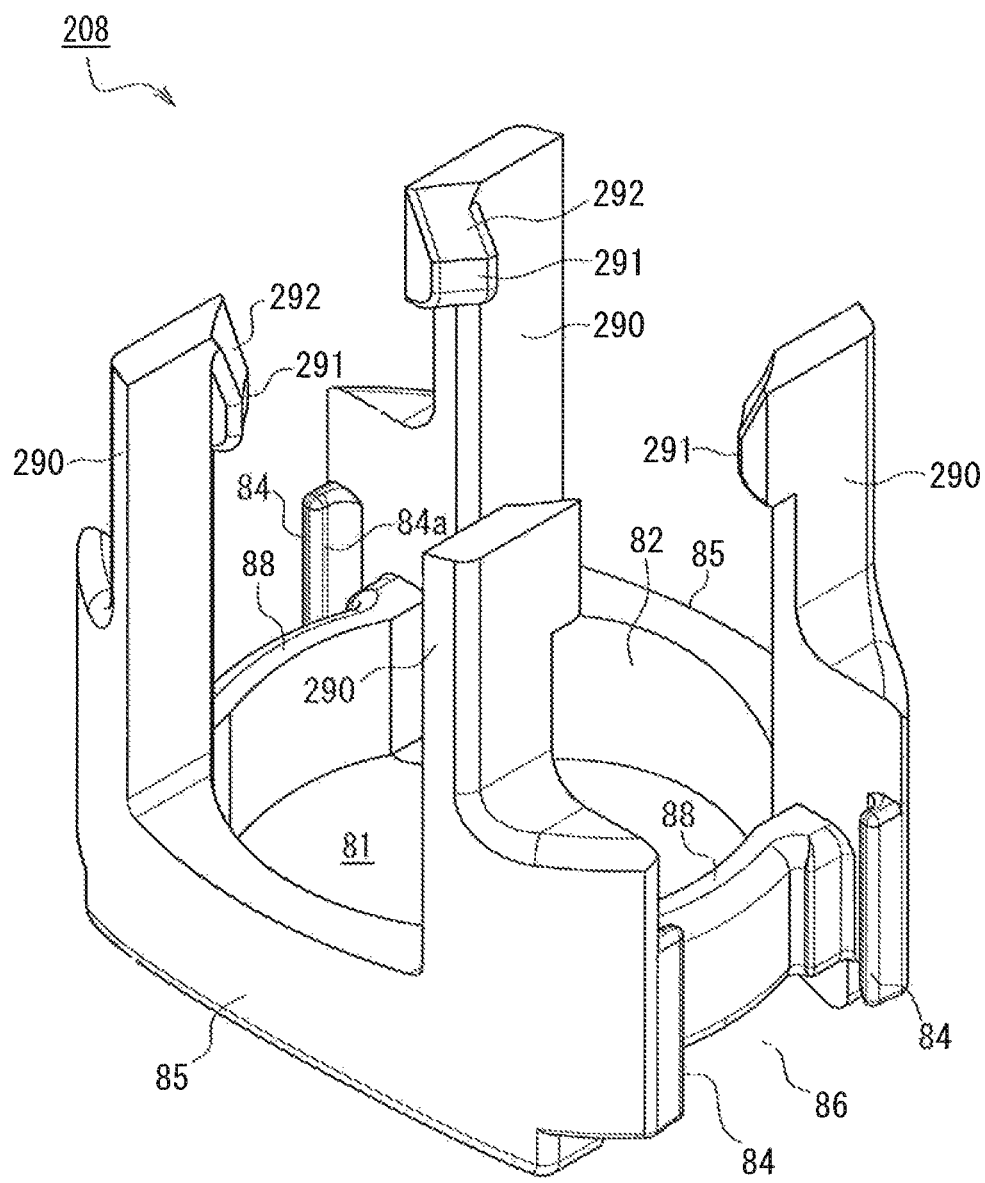
FIG. 15A is a perspective view of a lock ring according to Embodiment 2 of the present invention when viewed from above.
Figure 15B:
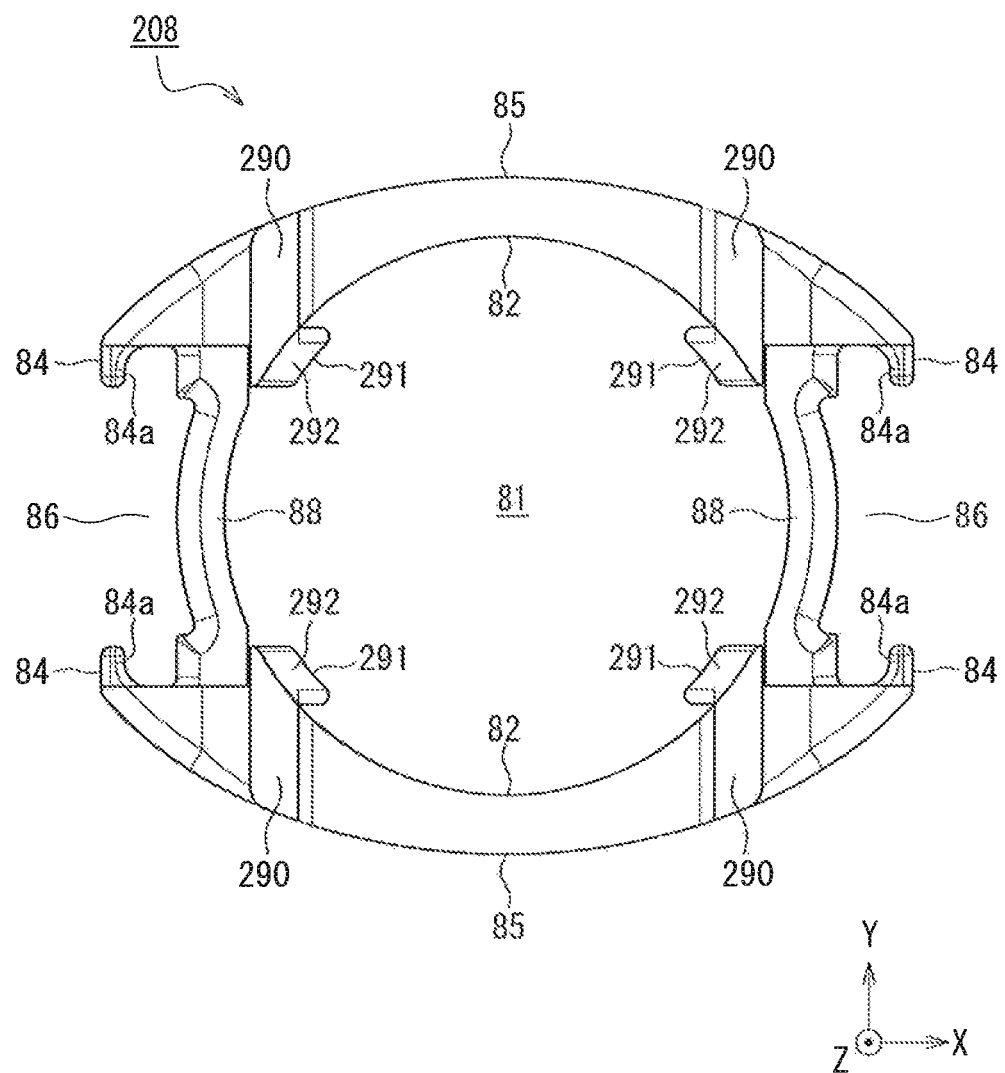
FIG. 15B is a plan view of the lock ring according to Embodiment 2 of the present invention.

FIG. 15A is a perspective view of a lock ring 208 according to Embodiment 2 when viewed from above, and FIG. 15B is a plan view of the lock ring 208.

As is the case with the lock ring 8 (see FIGS. 4A and 4B) of Embodiment 1, the lock rong 208 of Embodiment 2 includes the pair of arch-shaped portions 85 that are disposed opposing each other in the Y-axis direction and the pair of bridging portions 88 that are disposed opposing each other in the X-axis direction. The pair of bridging portions 88 couple the pair of arch-shaped portions 85 to each other. When the lock ring 208 is viewed from above (in plan view) (see FIG. 15B), the outer surfaces of the arch-shaped portions 85 conform to the same ellipse as the ellipse 219 (see FIG. 14C) that the outline of the connector main body 203 conforms to. The arch-shaped portions 85 are disposed on the minor axis of that ellipse. The bridging portions 88 are disposed on the major axis of that ellipse and at respective positions that are set back inward from that ellipse.

The lock ring 208 further includes four rods 290 that are parallel to the Z-axis. Each rod 290 extends upward from a coupling portion where a corresponding one of the arch portions 85 and a corresponding one of the bridging portions 88 are coupled to each other or near that coupling portion. A projection 291 protruding toward the opening 81 is provided at or near a leading end of each rod 290. An inclined surface 292 is provided at an upper surface of each projection 291. The inclined surface 292 is inclined so as to slope down toward the opening 81.

The lock ring 208 has two-fold rotational symmetry (when rotated 180 degrees, the lock ring 208 coincides with its state prior to rotation).

3. Male Connector (Lever Lock-Type Male Connector)

Figure 16A:
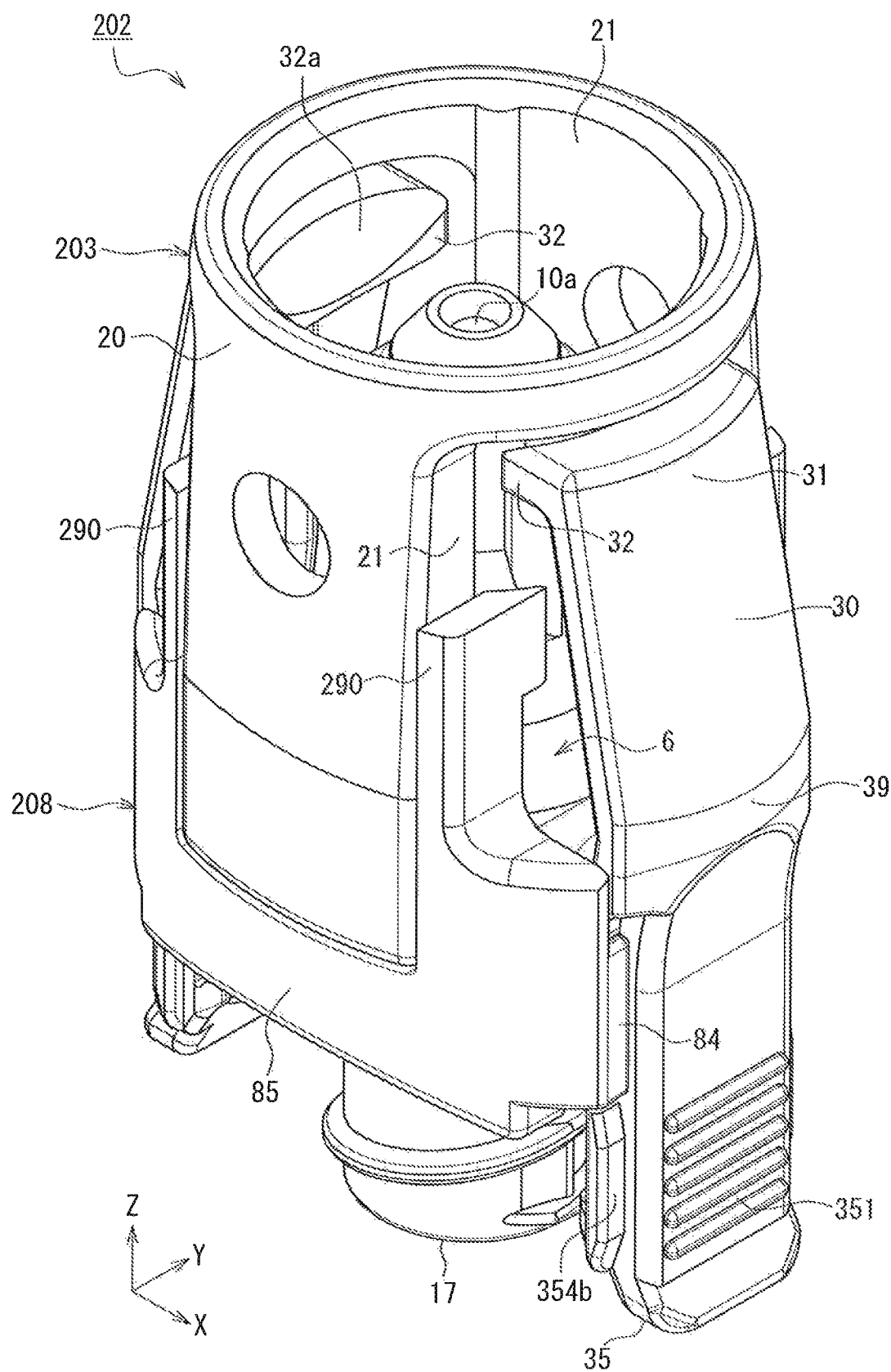
FIG. 16A is a perspective view of a lever lock-type male connector according to Embodiment 2 of the present invention when viewed from above.

As in Embodiment 1, a lever lock-type male connector (hereinafter simply referred to as "male connector") 202 of Embodiment 2 is obtained by attaching the lock ring 208 and the shield 6 (see FIG. 3A to 3C) to the connector main body 203. FIG. 16A is a perspective view of the male connector 202 when viewed from above, FIG. 16B is a perspective view of the male connector 202 when viewed from below, and FIG. 16C is a plan view of the male connector 202.

Figure 16B:
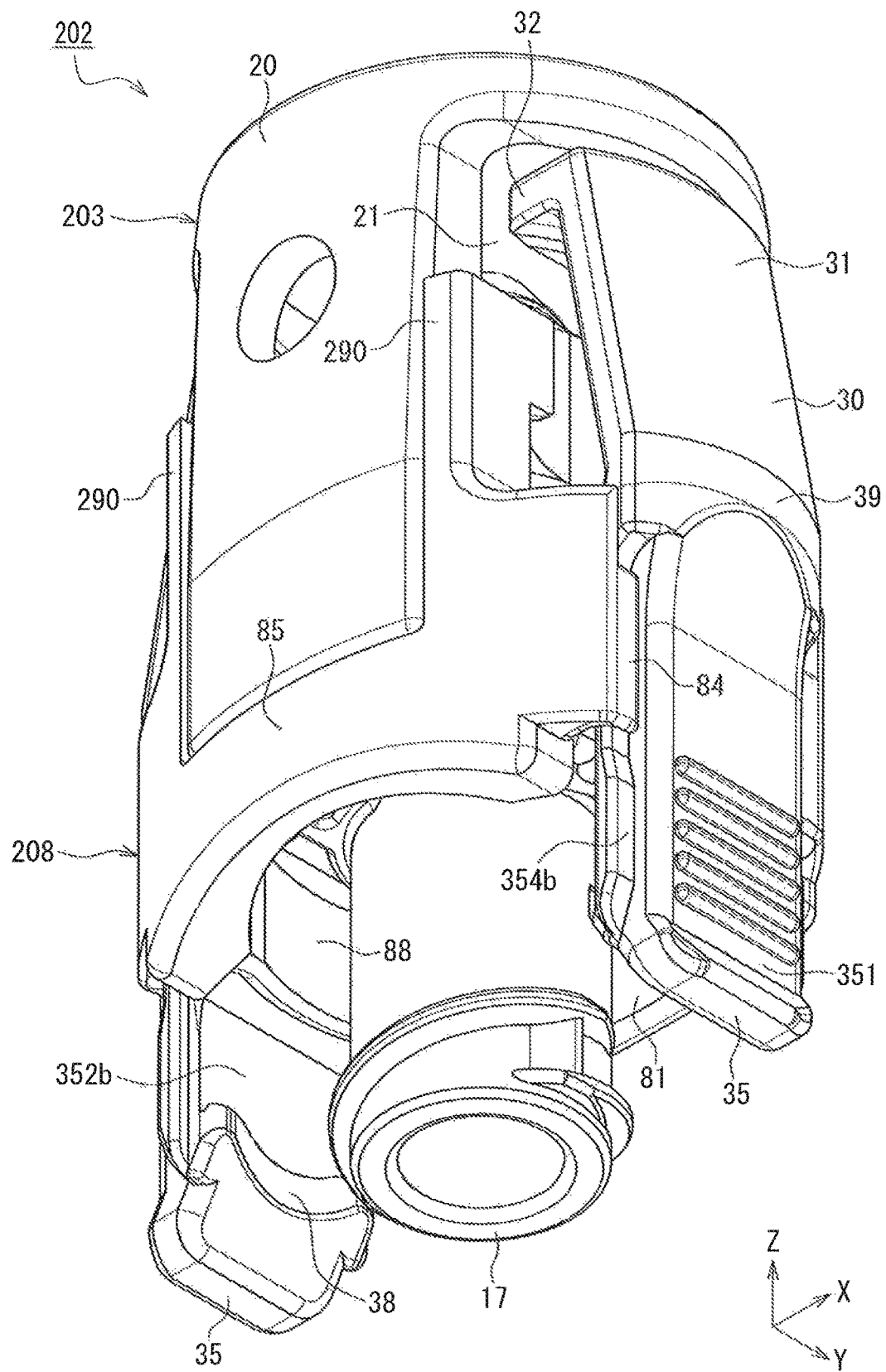
FIG. 16B is a perspective view of the lever lock-type male connector according to Embodiment 2 of the present invention when viewed from below.

As shown in FIGS. 16A and 16B, the four rods 290 of the lock ring 208 are respectively fitted into the four cut-outs 215$n$ (see FIG. 14B) that are provided in the base 15 of the connector main body 203. The rods 290 extend upward beyond the base 15 within the opening 21 of the hood 20. The projections 291 and the inclined surfaces 292 (see FIG. 15A) provided at the upper ends of the rods 290 are located above (on the male luer 10 side of) the base 15 and below (on the base 15 side of) the locking claws 32 provided in the levers 30.

Figure 16C:
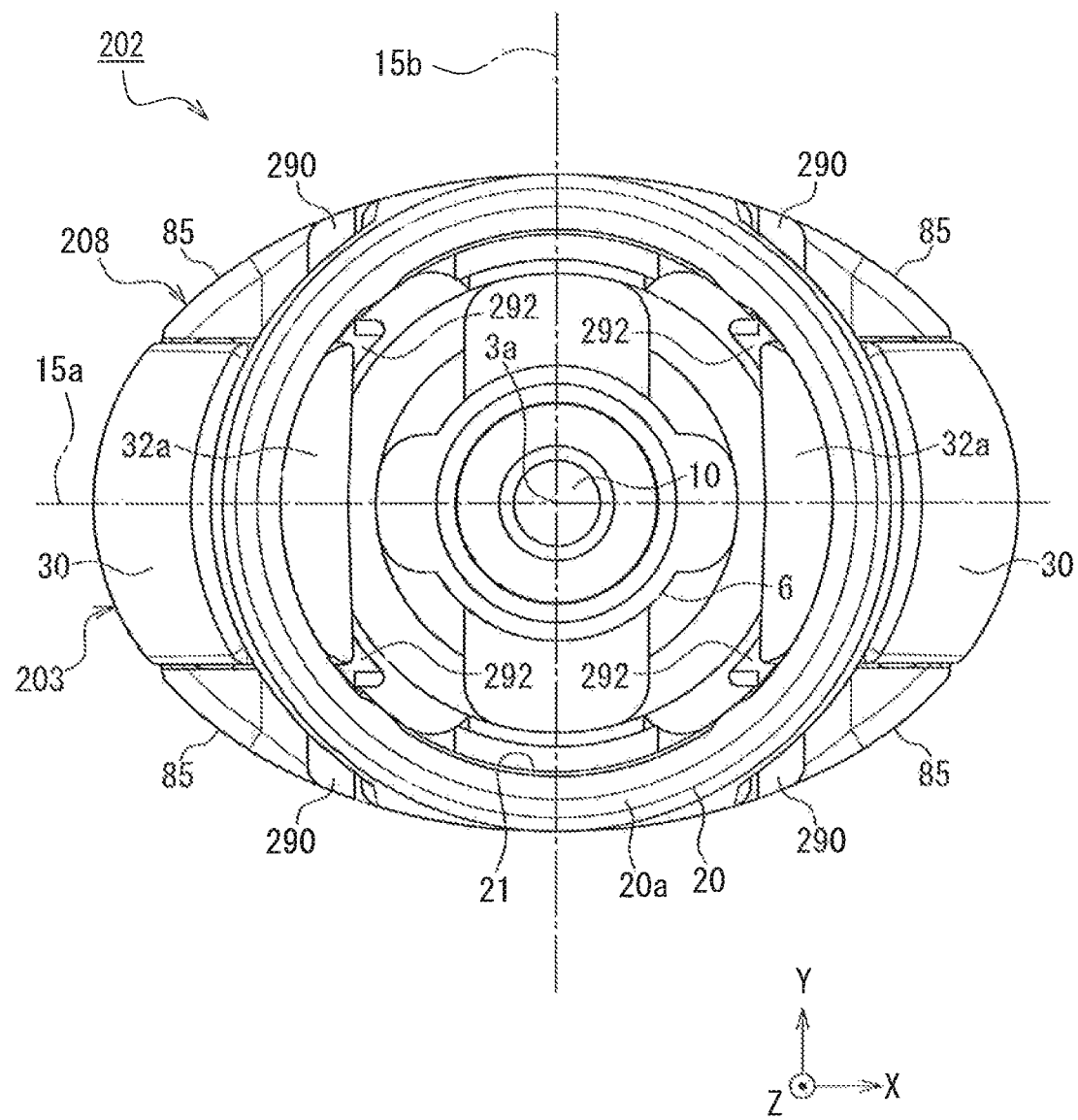
FIG. 16C is a plan view of the lever lock-type male connector according to Embodiment 2 of the present invention.

As shown in FIG. 16C, when viewed from above (in plan view) along the central axis 3*a*, in addition to the inclined surfaces 32*a* of the locking claws 30 provided in the levers 30, the inclined surfaces 292 of the projections 291 provided in the rods 290 protrude inward toward the male luer 10 from the end edge that surrounds the opening 21 of the hood 20.

The outer surfaces of the arch-shaped portions 85 of the lock ring 208 conform to an ellipse (see FIG. 15B). The ellipse that the arch-shaped portions 85 conform to coincides with the ellipse 219 shown in FIG. 14C. Therefore, as shown in FIG. 16C, when viewed from above, the outline of the male connector 202 has an elliptical shape with the major axis 15*a* and the minor axis 15*b*. The outline of this elliptical shape is constituted by the connector main body 203 and the lock ring 208. In Embodiment 2, although the cut-outs 215*n* are provided in the outer end edge of the base 15 of the connector main body 203 (see FIG. 14C), the outer surfaces of the arch-shaped portions 85 of the lock ring 208 compensate for the cut-outs 215*n*, and the outline of the male connector 202 in plan view has an elliptical shape.

As shown in FIG. 16B, the tubular portion 17 of the connector main body 203 is inserted into the opening 81 (see FIG. 15A) of the lock ring 208. Each pair of claws 84 of the lock ring 208 that oppose each other in the Y-axis direction hold a corresponding one of the operating portions 35 that is disposed therebetween from both sides.

As in Embodiment 1, the lock ring 208 is movable in the vertical direction relative to the connector main body 203. Upward movement of the lock ring 208 is restricted by the lock ring 208 (in particular, arch-shaped portions 85 thereof) colliding with the lower surface of the base 15. Downward movement of the lock ring 208 is restricted by the lock ring 208 (in particular, bridging portions 88 thereof) colliding with the stopping projections 38 provided in the operating portions 35. FIGS. 16A to 16C show a state in which the lock ring 208 has been moved to its uppermost position (highest position; first position).

When the lock ring 208 is at its highest position, the pressure contact portions 354*b* (locking projections), which protrude from the sliding ribs 354, are located directly below the respective claws 84, and the claws 84 are close to or abut against the pressure contact portions 354*b* in the vertical direction. Thus, the lock ring 208 is prevented from being lowered from the highest position due to gravity, vibrations, and the like. That is to say, the pressure contact portions 354*b* that are close to or abut against the lock ring 208 constitute a "first movement prevention mechanism" that prevents the lock ring 208 at its highest position from being unintentionally lowered.

When the lock ring 208 is at its highest position, the bridging portions 88 (see FIG. 15A) of the lock ring 208 oppose the recessed regions 352*a* (see FIG. 14B) of the operating portions 35, respectively, in the X-axis direction. As in Embodiment 1, the inner surface 352 (recessed region 352*a*) of each operating portion 35 is spaced apart from a corresponding one of the bridging portions 88 of the lock ring 208 in the X-axis direction, and the gap 356 is formed therebetween. Thus, in a state in which the lock ring 208 is at its highest position, the levers 30 can be pivoted such that the locking portions 31 and the locking claws 32 move away from the male luer 10.

The state shown in FIG. 16A to 16C, in which the lock ring 208 has been moved to its highest position, is referred to as the "initial state" of the male connector 202. In the initial state, substantially no external force acts on the levers 30, and the shield 6 is not compressively deformed in the vertical direction.

4. Method of Use

As in Embodiment 1, a male connector assembly can be configured by connecting, to the male connector 202 of Embodiment 2, the screw lock-type connector 100 (see FIGS. 8A and 8B) to which the tube 190 is connected. Since the male connector assembly of Embodiment 2 is the same as the male connector assembly 1 of Embodiment 1 except that the configuration of the male connector 202 is different, a detailed description thereof is omitted.

The male connector 202 is used connected to a female connector. The female connector may be the female connector 900 (see FIGS. 10A and 10B), which has been described in Embodiment 1.

The male connector 202 and the female connector 900 can be connected to each other in the following manner.

Figure 17:
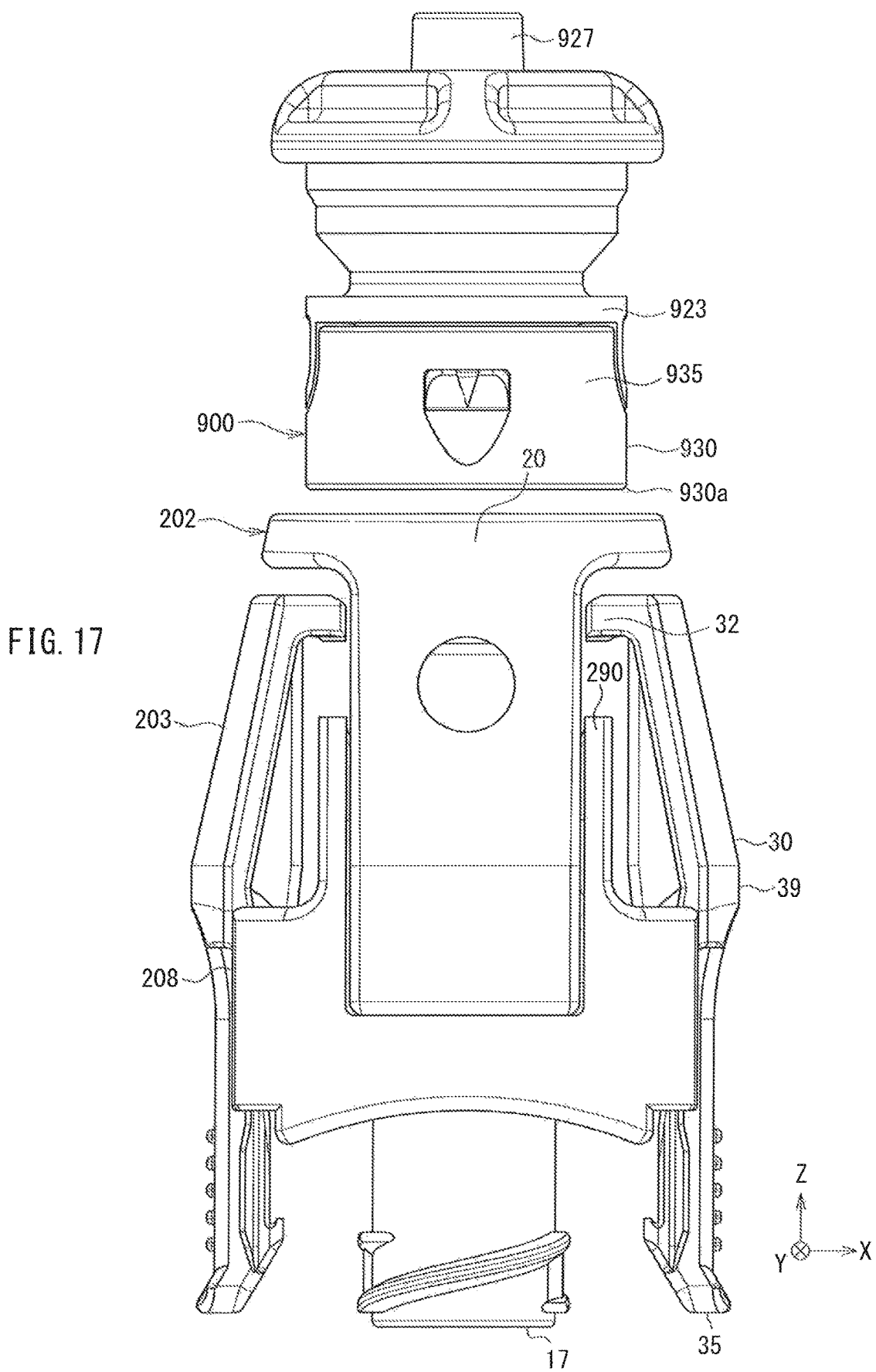
FIG. 17 is a front view of the male connector according to Embodiment 2 of the present invention immediately prior to being connected to a female connector.

First, as shown in FIG. 17, the male connector 202 and the female connector 900 are coaxially placed opposing each other. Although not shown in the drawings, a flexible tube is connected to the tubular portion 17 of the male connector 202 directly or indirectly via the screw lock-type connector 100 (see FIGS. 8A and 8B). Moreover, a flexible tube is connected to the male luer 927 of the female connector 900 directly or indirectly via a certain member.

With the connector main body 203 (for example, hood 20 thereof) being held by one hand and the female connector 900 being held by the other hand, the male connector 202 and the female connector 900 are brought close to each other. Furthermore, the cap 930 of the female connector 900 is inserted into the hood 20.

As shown in FIG. 16C, when the male connector 202 is viewed from above, the inclined surfaces 32*a* of the levers 30 and the inclined surfaces 292 of the lock ring 208 protrude into the opening 21 of the hood 20. The inclined surfaces 32*a* are located above the inclined surfaces 292.

Accordingly, first, as in Embodiment 1, the outer end edge 930*a* (see FIGS. 10A and 10B) of the top plate 931 of the cap 930 abuts against the inclined surfaces 32*a* (see FIG. 16A) of the locking claws 32. When the female connector 900 is pushed further into the hood 20 toward the base 15, the end edge 930*a* of the cap 930 elastically displaces the levers 30 so as to move the locking claws 32 away from the male luer 10. Then, the locking claws 32 slide on the peripheral wall 935 of the cap 930.

Figure 18:
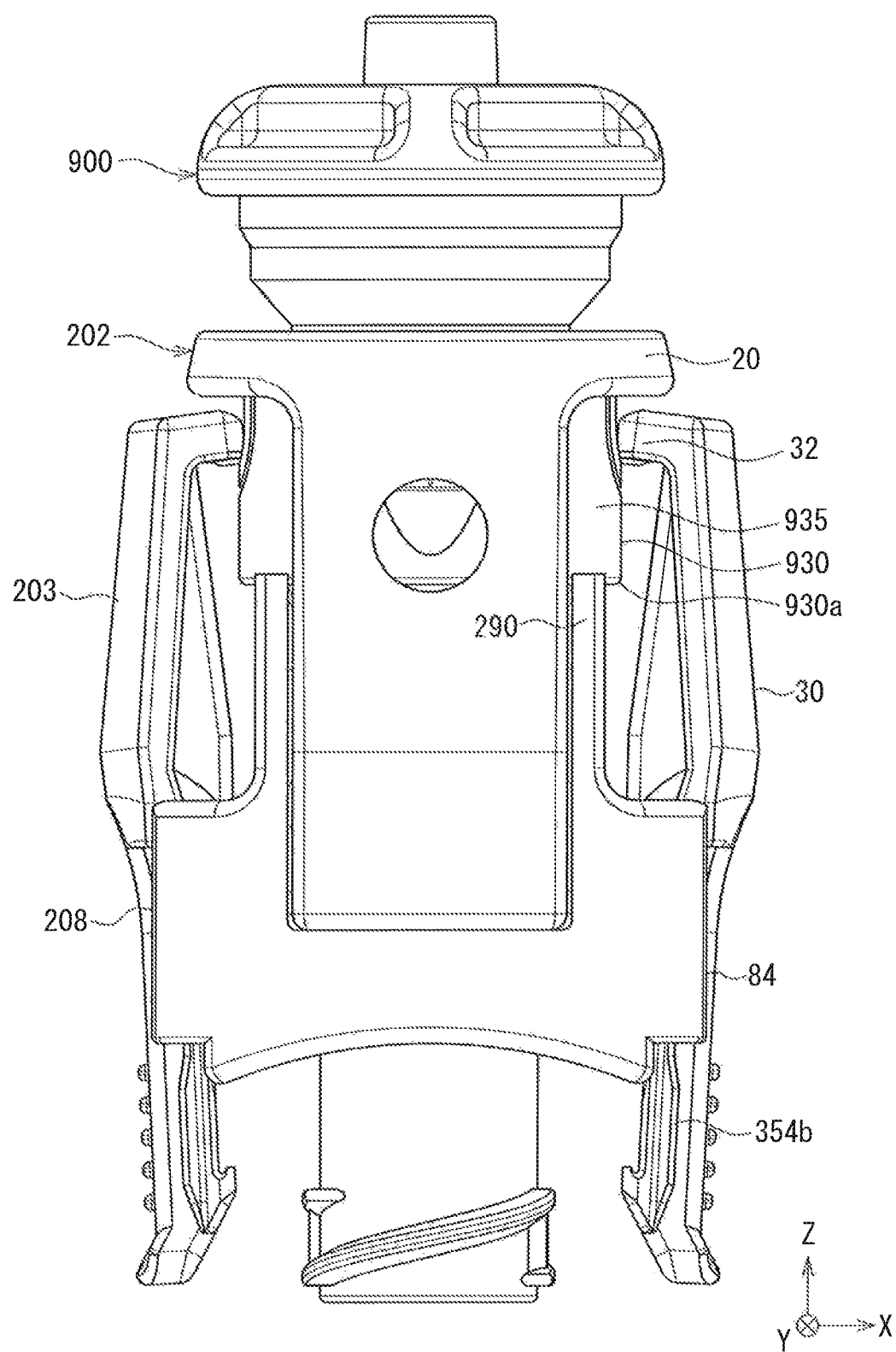
FIG. 18 is a front view of the male connector according to Embodiment 2 of the present invention in a state in which the female connector abuts against inclined surfaces at leading ends of respective rods of the lock ring.

Subsequently, the end edge 930*a* (see FIGS. 10A and 10B) of the top plate 931 of the cap 930 collides with the inclined surfaces 292 of the rods 290. FIG. 18 shows this state (in FIG. 18, the inclined surfaces 292 that are located behind the rods 290 cannot be seen). From this state, the female connector 900 is pushed further into the hood 20 toward the base 15. The lock ring 208 receives a downward force from the female connector 900, and the claws 84 of the lock ring 208 mount the respective pressure contact portions 354*b* of the lever 30 and slide thereon. That is to say, the lock ring 208 starts to move downward from its highest position against the first movement prevention mechanism. When the female connector 900 is inserted further into the hood 20, the lock ring 208 is moved downward relative to the connector main body 203 together with the female connector 900.

Figure 19A:
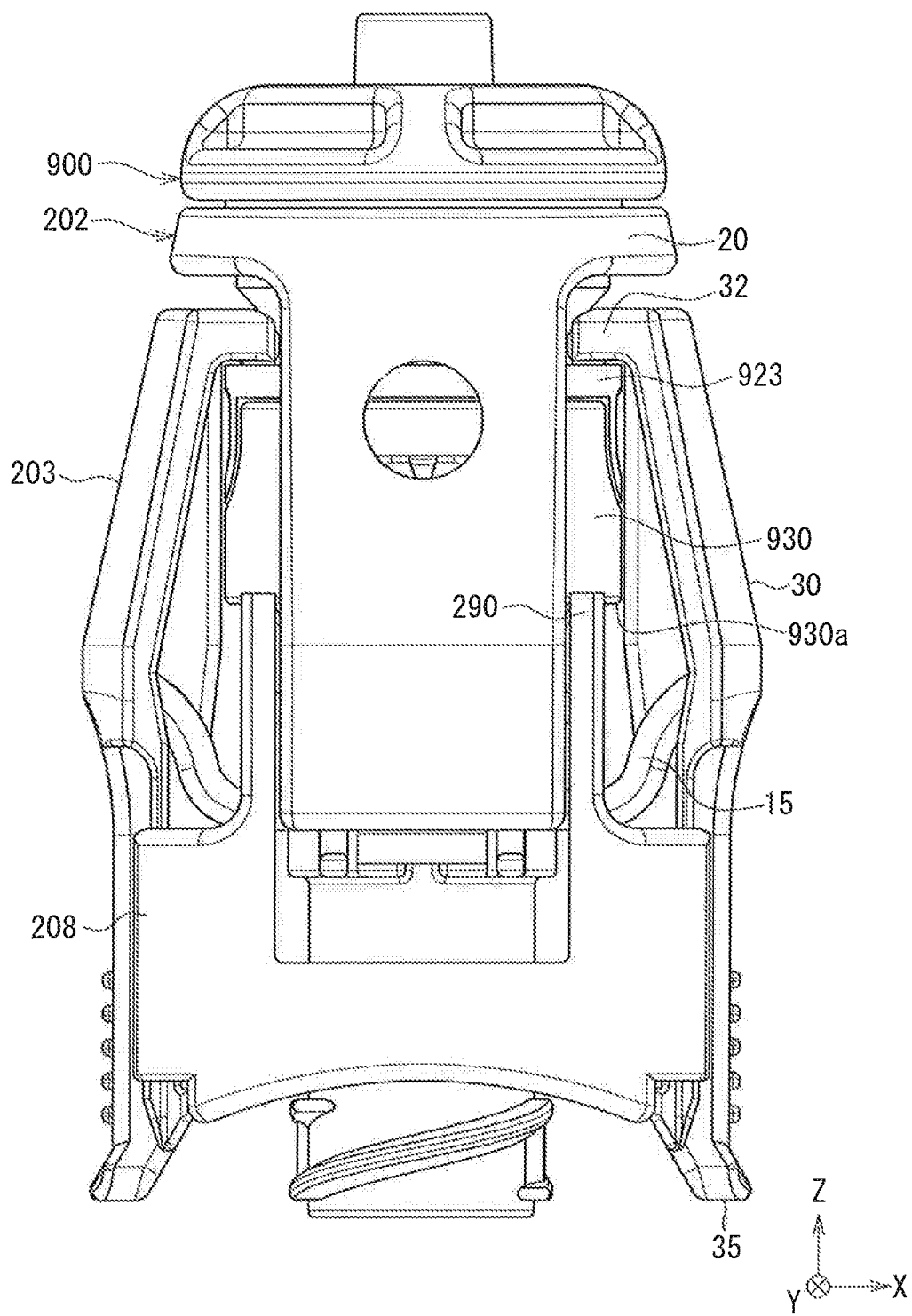
FIG. 19A is a front view of the male connector according to Embodiment 2 of the present invention in a state in which locking claws of levers are engaged with the female connector.
Figure 19B:
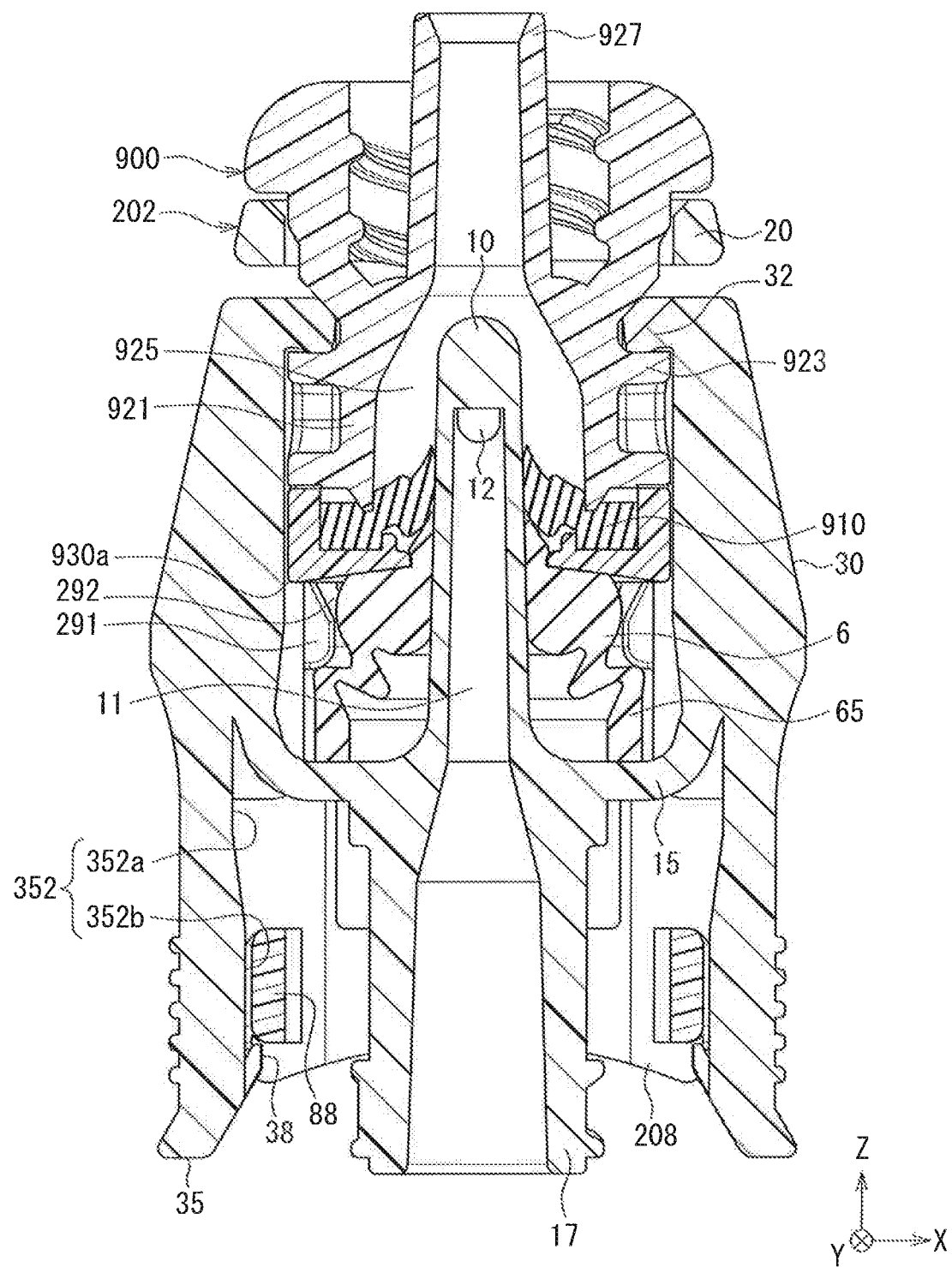
FIG. 19B is a cross-sectional view of the male connector in FIG. 19A.

While the lock ring 208 is moving downward, the locking claws 32 of the levers 30 sequentially slide on the peripheral wall 935 of the cap 930 and the annular projection 923 (see FIGS. 10A and 10B). Then, when the locking claws 32 have passed the annular projection 923, the base 15 of the connector main body 203 elastically recovers, and the locking claws 32 engage with the annular projection 923 (locked state). FIG. 19A is a side view showing this state, and FIG. 19B is a cross-sectional view thereof. The lock ring 208 has moved to its lowest position (second position).

As shown in FIG. 19B, the male luer 10 penetrates the slit 911 (see FIGS. 10A and 10B) of the septum 910, and the openings of the lateral holes 12 of the male luer 10 are exposed in the cavity 925 of the seat 921. Therefore, the flow channel 11 of the male luer 10 and the cavity 925 of the seat 921 are in communication with each other. The shield 6 receives the compressive force in the vertical direction. In particular, the outer circumferential wall 65 of the shield 6 is deformed such that its vertical dimension is reduced.

The inner surfaces 352 (in particular, lock regions 352b thereof (see FIG. 14B)) of the operating portions 35 are located close to or abut against the respective bridging portions 88 of the lock ring 208 in the X-axis direction. Therefore, the levers 30 cannot be pivoted so as to move the locking claws 32 away from the male luer 10. The lock ring 208 when located at its lowest position functions as the "lever pivotal movement prevention mechanism" that prevents the levers 30 from pivoting. For this reason, an unforeseen situation in which the locking claws 32 are unintentionally disengaged from the annular projection 923 by an external force acting on the operating portions 35, and the male connector 202 and the female connector 900 are disconnected from each other will not occur.

When the lock ring 208 is at its lowest position, the stopping projections 38 are located below the bridging portions 88 of the lock ring 208 and are located close to or abut against the bridging portions 88. The stopping projections 38 prevent the lock ring 208 from moving further downward from the lowest position and becoming dislodged downward from between the operating portions 35.

When the locking claws 32 are engaged with the female connector 900 and the lock ring 208 is at its lowest position, the end edge 930a of the cap 930 is located above the inclined surfaces 292 of the rods 290 and are located close to or abut against the inclined surfaces 292. For this reason, the lock ring 208 cannot be unintentionally moved upward from the lowest position due to vibrations, an external force, and the like. That is to say, the inclined surfaces 292 that are provided so as to oppose the female connector 900 in the vertical direction constitute the "second movement prevention mechanism" that prevents the lock ring 208 at its lowest position from being unintentionally moved upward.

The male connector 202 and the female connector 900 can be disconnected from each other in the following manner.

In the state shown in FIGS. 19A and 19B, the lock ring 208 is pushed upward relative to the connector main body 203 and the female connector 900. The upward force that is applied to the lock ring 208 acts on the female connector 900 via the inclined surfaces 292 of the lock ring 208. However, since the locking claws 32 of the levers 30 are engaged with the female connector 900, the position of the female connector 900 relative to the connector main body 203 does not change. Accordingly, the upward force acts so as to displace the inclined surfaces 292, which the end edge 930a of the female connector 900 abuts against, outward (in the direction away from the male luer 10). Thus, the inclined surfaces 292 are displaced outward while sliding on the end edge 930a, and accordingly, the rods 290 are deformed and bent so as to move the inclined surfaces 292 away from the male luer 10. When the inclined surfaces 292 are displaced outward of the end edge 930a, the lock ring 208 starts to move upward relative to the connector main body 203 and the female connector 900. The lock ring 208 moves upward while the projections 291 (see FIG. 15A) of the rods 290 slide on the peripheral wall 935 of the cap 930.

Figure 20:
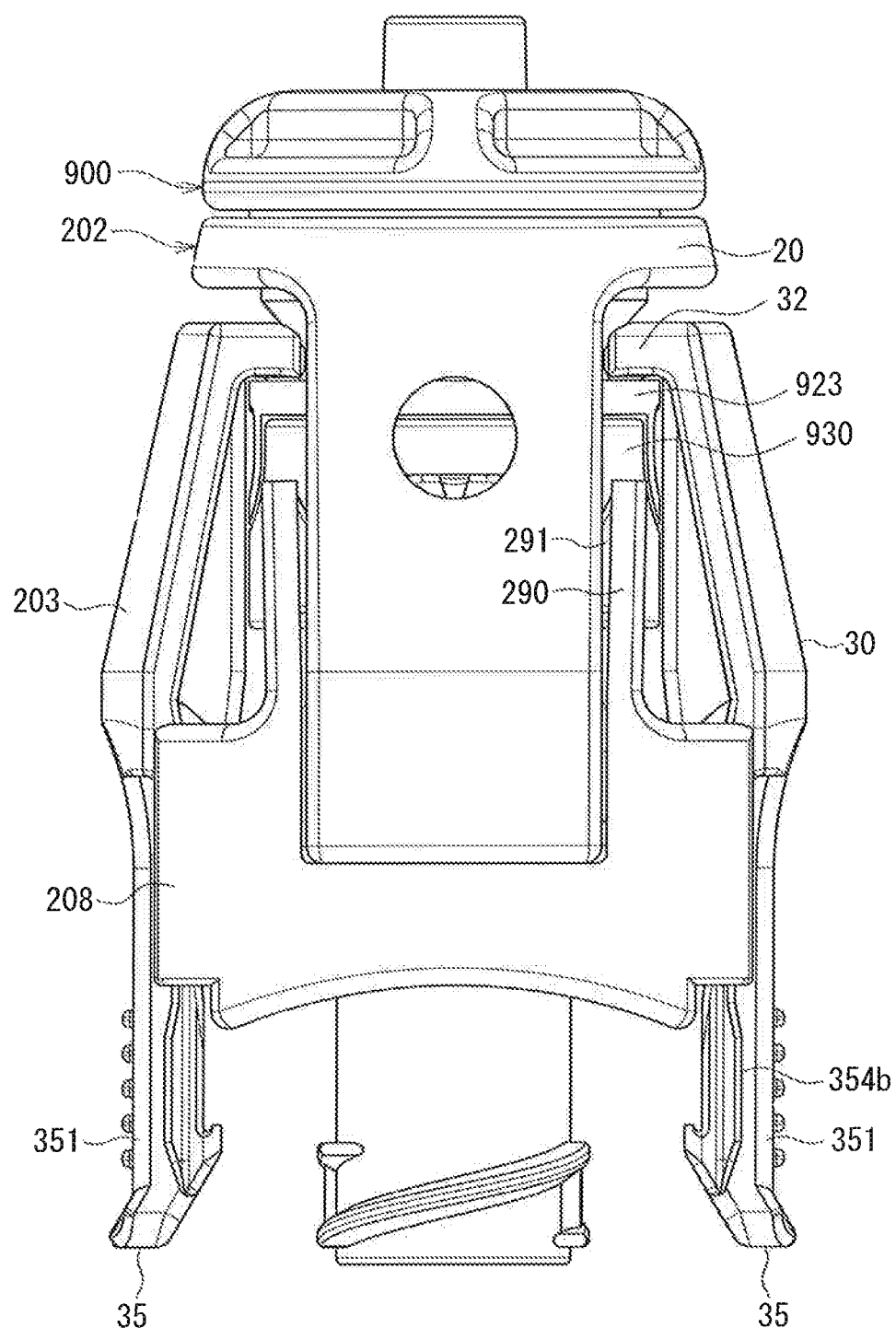
FIG. 20 is a front view of the male connector according to Embodiment 2 of the present invention in which the locking claws of the levers are engaged with the female connector and the lock ring is at the highest position.

As shown in FIG. 20, the lock ring 208 is moved up to the highest position. The projections 291 abut against the peripheral wall 935 of the cap 930 or the annular projection 923, of the female connector 900 in the radial direction, and the rods 290 are elastically deformed and bent outward. The locking claws 32 of the levers 30 are still engaged with the female connector 900.

In FIG. 20, a pressing force is applied to the outer surfaces 351 of the operating portions 35 to cause the levers 30 to pivot, and thus, the locking claws 32 are disengaged from the annular projection 923. Subsequently, in the state in which the levers 30 have pivoted, the connector main body 203 and the female connector 900 are pulled apart from each other, and thus, the male connector 202 and the female connector 900 can be disconnected from each other (see FIG. 17). The rods 290 elastically recover immediately.

5. Effects

As in Embodiment 1, the male connector 202 of Embodiment 2 includes the levers 30 including the locking claws 32, and the levers 30 function as the "lever-type lock mechanism" for maintaining (locking) the state in which the male connector 202 is connected to the female connector 900. The locking claws 32 are engaged with the female connector 900 simply by inserting the female connector 900 into the opening 21 of the hood 20 and pushing the female connector 900 further inward toward the male connector 202, and thus, connection of the male connector 202 to the female connector 900 is completed. Disengagement of the locking claws 32 from the female connector 900 can be performed simply by, as in Embodiment 1, pushing the outer surfaces 351 of the operating portions 35 and slightly pivoting the levers 30 in the state in which the lock ring 208 has been moved to the highest position. Therefore, the male connector 202 and the male connector assembly including the male connector 202 of Embodiment 2 provide excellent ease of operations for connection and disconnection to and from the female connector 900.

The male connector 202 of Embodiment 2 includes a double lock mechanism that has, in addition to the lever-type lock mechanism (first lock mechanism) for maintaining a state in which the male connector 202 is connected to the female connector 900, the lock ring 208 (second lock mechanism) for maintaining the locked state that is maintained by the lever-type lock mechanism. Thus, the likelihood of the locked state that is maintained by the lever-type lock mechanism (first lock mechanism) being unintentionally cancelled is reduced.

According to Embodiment 1, in order for the second lock mechanism to effectively function, it is necessary to move the lock ring 8 from the highest position (see FIG. 12) to the lowest position (FIGS. 13A to 13E). For this reason, there is a possibility that the operator will perform an erroneous operation in which they forget to move the lock ring 8 to the lowest position under the illusion that connection of the male connector assembly 1 and the female connector 900 has been completed due to the locking claws 32 being engaged with the female connector 900 (see FIG. 12). If the lock ring 8 is left remaining at the highest position, the locking claws 32 may unintentionally disengage from the female connector 900 due to an external force being applied to the operating portions 35.

In contrast, according to Embodiment 2, the lock ring 208 includes the rods 290 that extend toward the male luer 10 beyond the base 15. When viewed from above along the longitudinal direction of the male luer 10 (that is, along the central axis 3a), the inclined surfaces 292 of the rods 290 protrude inward toward the male luer 10 from the end edge 20a of the opening 21 of the hood 20 (see FIG. 16C). Thus, when the female connector 900 is inserted into the opening 21 of the hood 20, the female connector 900 collides with the inclined surfaces 292 of the rods 290. When the female connector 900 is inserted further into the hood 20 toward the base 15, the lock ring 208 is moved downward by the female connector 900. Then, at the same time as the locking claws 32 of the levers 30 engage with the female connector 900, the lock ring 208 reaches the lowest position. In this manner, according to Embodiment 2, in the operation of connecting the female connector 900 to the male connector 202, the lock ring 208 moves relative to the connector main body 203 in conjunction with the female connector 900. When engagement of the locking claws 32 with the female connector 900 has been completed, it is certain that the lock ring 208 has reached the lowest position. When the lock ring 208 remains at the highest position, the locking claws 32 cannot be engaged with the female connector 900. Accordingly, the erroneous operation of forgetting to move the lock ring 8 to the lowest position, which may occur in Embodiment 1, is unlikely to occur in Embodiment 2. For this reason, according to Embodiment 2, the likelihood of the locked state that is maintained by the lever-type lock mechanism being unintentionally cancelled due to an external force acting on the operating portions 35 of the levers 30 is further reduced, and thus the safety is improved.

Moreover, according to Embodiment 2, both the engagement of the locking claws 32 with the female connector 900 and the movement of the lock ring 208 from the highest position to the lowest position can be performed simply by pushing the female connector 900 inward toward the connector main body 203. During this operation, it is not necessary to exchange the connector main body 203 and the female connector 900 from one hand to the other and vice versa. Also, it is not necessary to touch the lock ring 208 in order to move the lock ring 208. Accordingly, the operation of connecting the female connector 900 to the male connector 202 can be performed even more simply and quickly than in Embodiment 1.

When the locking claws 32 are engaged with the female connector 900 and the lock ring 208 is at its lowest position, the inclined surfaces 292 serving as the second movement prevention mechanism prevents unintentional upward movement of the lock ring 208. However, when a large force acting upward is applied to the lock ring 208, the upward force causes the rods 290 to deform and curve such that the inclined surfaces 292 are displaced outward along the radial direction. Thus, the second movement prevention mechanism is released, and the lock ring 208 can be moved from the lowest position to the highest position. Therefore, the female connector 900 can be disconnected from the male connector 202 in the same manner as in Embodiment 1, by moving the lock ring 208 from the lowest position to the highest position and then disengaging the locking claws 32 from the female connector 900. Since it is necessary to perform such a two-stage operation in order to disconnect the male connector 202 and the female connector 900 from each other, the likelihood of unintentional disconnection of the male connector 202 and the female connector 900 due to an erroneous operation is reduced, and thus the safety is improved.

In order to extend the rods 290 of the lock ring 208 from the lower side to the upper side of the base 15, the cut-outs 215n are provided in the base 15. For this reason, unlike the connector main body 3 of Embodiment 1, the projection outline of the connector main body 203 (or the projected shape of the connector main body 203, see FIG. 14C) when viewed from above along the central axis 3a is not an exact elliptical shape. On the other hand, when the lock ring 208 is viewed from above, the outer surfaces of the arch-shaped portions 85 of the lock ring 208 conform to the ellipse 219 shown in FIG. 14C (see FIG. 15B). Therefore, as shown in FIG. 16C, when viewed from above along the central axis 3a, the outline of the male connector 202 has an elliptical shape with the major axis 15a and the minor axis 15b. The outline of this elliptical shape is constituted by a combination of the connector main body 203 and the lock ring 208. In this manner, even when the cut-outs 215n are provided in the outer end edge of the base 15 of the connector main body 203, the outer surface of the lock ring 208 compensates for the cut-outs 215n, and thus, the male connector 202 having an elliptical outline in plan view can be realized. As is the case with the male connector 2 and the male connector assembly 1 of Embodiment 1, if the male connector 202 or the male connector assembly using the male connector 202 is pinned under the patient with the central axis 3a extending in the horizontal direction, the male connector 202 or the male connector assembly can easily rotate so that the direction of the major axis 15a becomes the horizontal direction. Therefore, it is unlikely that the patient will feel pain or even develop a decubitus ulcer as a result of the skin or soft tissue of the patient being continuously pressed.

As described above, even if the connector main body 203 alone does not have a substantially elliptical outline, the male connector 202 that has a substantially elliptical outline can be realized by attaching the lock ring 208 to the connector main body 203. In the case where a male connector that has a substantially elliptical outline is configured by combining the connector main body with the lock ring as in Embodiment 2, at least one of the connector main body and the lock ring is not required to have a substantially elliptical outline. For this reason, it is possible to provide the cut-outs 215n in the base 15 of the connector main body 203 (see FIGS. 14A to 14C) and to provide the cut-outs 86 in the lock ring 208 (see FIGS. 15A and 15B) as in Embodiment 2, and thus, the degree of freedom of design of the connector main body and the lock ring is improved.

Embodiment 2 is the same as Embodiment 1 except for the above-described differences. The description of Embodiment 1 is also applicable to Embodiment 2 as appropriate.

A male connector may also be configured by combining the connector main body 203 of Embodiment 2 with the lock ring 8 of Embodiment 1.

6. Various Modifications

It should be understood that the foregoing embodiments are given by way of example only. The present invention is not limited to the foregoing embodiments, and modifications can be made thereto as appropriate.

The external shapes of the male connector assembly 1, the male connectors 2 and 202, and the connector main bodies 3 and 303 are not limited to those of the foregoing embodiments.

For example, the outline (shape in plan view) of the male connector when viewed along the central axis 3a may also have a substantially circular shape or may have any shape such as a substantially rectangular shape, a substantially square shape, a substantially rhombic shape, and various polygonal shapes. However, it is preferable that the outline of the male connector has the major axis 15a in the direction (first direction, that is, X-axis direction) in which the male luer 10 opposes the levers 30, and furthermore, it is preferable that the outline of the male connector has a substantially elliptical shape.

Figure 21:
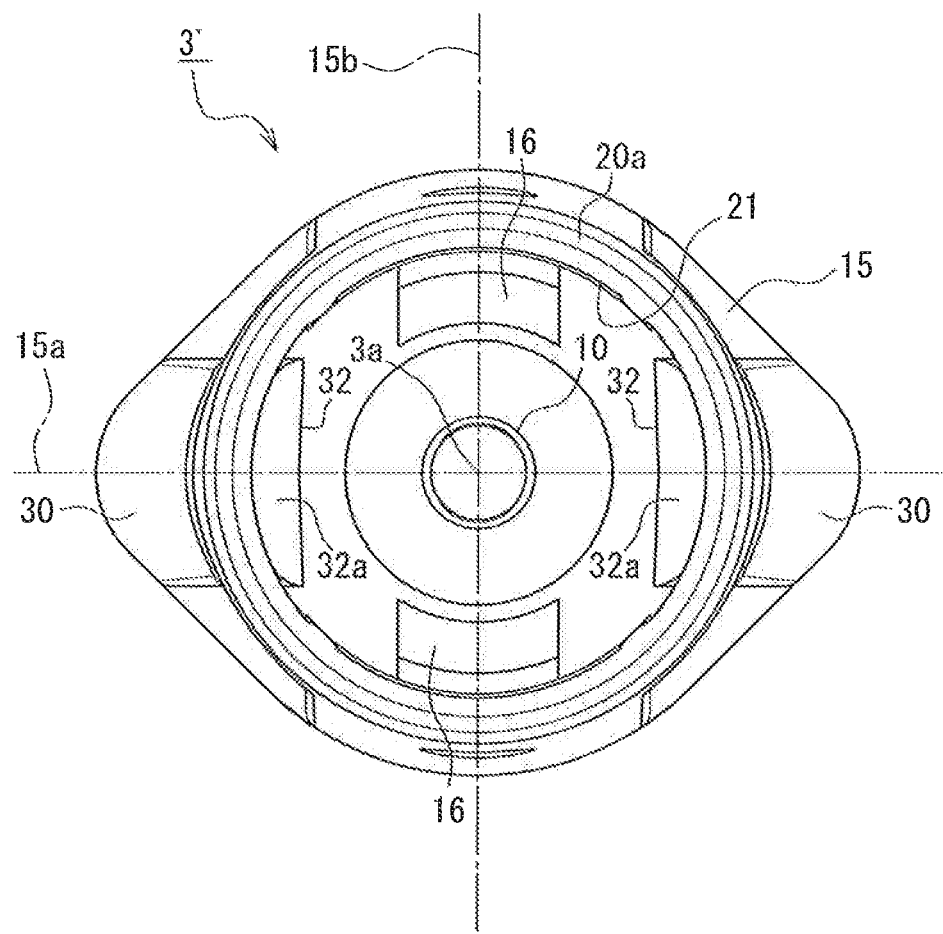
FIG. 21 is a plan view of a connector main body according to another embodiment of the present invention.
Figure 22:
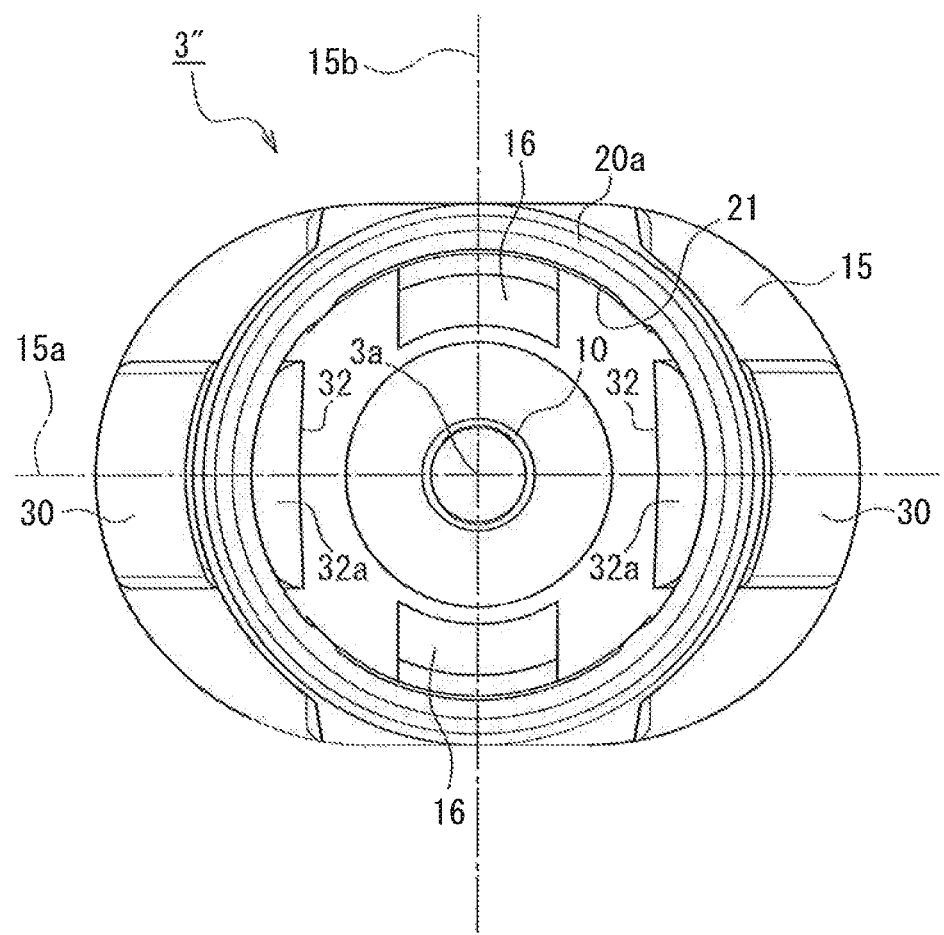
FIG. 22 is a plan view of a connector main body according to yet another embodiment of the present invention.

The "substantially elliptical shape" is not required to be an exact ellipse. FIG. 21 is a plan view of a connector main body 3' having a substantially rhombic outline, and FIG. 22 is a plan view of a connector main body 3" whose outline has a shape (hereinafter referred to as "substantially track shape") that approximates the shape of a track of an athletic field. In FIGS. 21 and 22, members that correspond to the members shown in FIG. 2E are denoted by the same reference numerals as those in FIG. 2E. As is the case with the connector main body 3 shown in FIG. 2E, the outlines of the connector main bodies 3' and 3" are defined by the outline of the base 15. The outline of the connector main body 3' in FIG. 21 is not an exact rhombus, because the four corners of a rhombus that are located on the major axis 15a and the minor axis 15b are chamfered and rounded. The outline of the connector main body 3" in FIG. 22 is constituted by two semicircles that have the same radius and that oppose each other in the direction of the major axis 15a, and two straight lines that connect the two semicircles and that are parallel to the major axis 15a. The radius of the two semicircles and the length of the two straight lines can be set as desired. For this reason, the outline of the connector main body 3" in FIG. 22 may also be a shape that is not similar to the exact shape of a track of an athletic field.

Generally, an outline having a "substantially elliptical shape" in the present invention means that, when an axis (axis extending in the direction in which the male luer 10 opposes the levers 30) which is orthogonal to the central axis 3a and on which the external dimension is largest is taken as the major axis 15a, the horizontal dimension along the major axis 15a is larger than the horizontal dimension in a direction that is perpendicular to the major axis 15a (excluding the case where the two horizontal dimensions are equal to each other). Preferably, the "substantially elliptical shape" of the present invention is symmetrical with respect to the major axis 15a. Specifically, the "substantially elliptical shape" of the present invention includes, in addition to an exact ellipse (excluding circles), a substantially rhombic shape (see FIG. 21) and a substantially track shape (see FIG. 22). It can safely be said that the outline (see FIG. 2E) of the connector main body 3 of Embodiment 1 and the outline (see FIG. 16C) of the male connector 202 of Embodiment 2 each have the shape of an exact ellipse.

In the case where a connector main body alone has a substantially elliptical outline like the connector main body 3 of Embodiment 1 and the connector main bodies 3' and 3", it is preferable that a lock ring combined with that connector main body does not protrude from the substantially elliptical outline of the connector main body in plan view. With this configuration, a male connector having a substantially elliptical outline can be easily obtained.

In the case where a connector main body alone does not have a substantially elliptical outline like the connector main body 203 of Embodiment 2 (see FIG. 14C), it is preferable that a male connector obtained by combining a lock ring with that connector main body has a substantially elliptical outline as a whole.

The base 15 of the substantially rhombic connector main body 3' shown in FIG. 21 may also be provided with cut-outs 215n that are similar to those of the connector main body 203 of the Embodiment 2. In this case, a male connector having a substantially rhombic outline in plan view can be realized by attaching a lock ring that can compensate for those cut-outs 215n to the connector main body 3'. Similarly, the base 15 of the substantially track-shaped connector main body 3" in FIG. 22 may also be provided with cut-outs 215n, and in this case as well, a male connector having a substantially track-shaped outline in plan view can be realized by attaching a lock ring that can compensate for those cut-outs 215n to the connector main body 3".

A male connector assembly can be configured in the same manner as in Embodiment 1 by using the male connector having the substantially elliptical outline. As in Embodiments 1 and 2 above, if such a male connector or a male connector assembly is pinned under the patient with the central axis 3a extending in the horizontal direction, the male connector or the male connector assembly can easily rotate so that the direction of the major axis 15a becomes the horizontal direction. Therefore, the likelihood of the patient feeling pain or even developing a decubitus ulcer as a result of the skin or soft tissue of the patient being continuously pressed can be reduced. Moreover, even if the operator forgets to move the lock ring to the lowest position, the likelihood of the state (locked state) in which the locking claws of the levers are engaged with the female connector being unintentionally cancelled can be reduced.

In Embodiments 1 and 2 above, when viewed along the Y-axis (minor axis 15b), the shape of the portion of the connector main body 3 or 203 that is located above the base 15 is a tapered shape whose horizontal dimension decreases as the distance from the base 15 increases in the upward direction (see FIGS. 2C, 13B, and 17). However, the present invention is not limited to this, and for example, this portion may also have a rectangular shape having a constant horizontal dimension. In this case, the locking portions 31 of the levers 30 extend parallel to the central axis 3a. Alternatively, the shape of the portion of the connector main body 3 or 203 that is located above the base 15 may also be an inverted trapezoidal shape whose horizontal dimension increases as the distance from the base 15 increases in the upward direction.

In Embodiments 1 and 2 above, when viewed along the X-axis (major axis 15a), the portion of the connector main body 3 or 203 that is located above the base 15 has a substantially rectangular shape having a constant horizontal dimension (see FIGS. 2D and 13C). However, the present invention is not limited to this, and for example, this portion may also have a tapered shape whose horizontal dimension decreases as the distance from the base 15 increases in the upward direction. That is to say, the external diameter of the hood 20 at the leading end 20a may be smaller than the diameter (minor diameter) of the connector main body 3 or 203 along the minor axis 15b (see FIG. 21). Alternatively, the shape of the portion of the connector main body 3 or 203 that is located above the base 15 may also be an inverted trapezoidal shape whose horizontal dimension increases as the distance from the base 15 increases in the upward direction.

In Embodiments 1 and 2 above, the outer surfaces of the operating portions 35 of the levers 30 are located nearer to the central axis 3a than the outer surfaces of the lever base portions 39 (see FIGS. 2C, 13B, and 17). However, the present invention is not limited to this. For example, when viewed along the minor axis 15b, the operating portions 35 may be located at the same positions as the lever base portions 39 with respect to the horizontal direction or may protrude outward compared with the lever base portions 39 in the horizontal direction. The further away the positions of the operating portions 35 from the central axis 3a in the horizontal direction, the higher the likelihood of an unintentional external force acting on the operating portions 35. However, when the lock ring 8 or 208 has been moved to the lowest position, even if an external force acts on the operating portion 35, there is almost no possibility that the state (locked state) in which the locking claws 32 are engaged with the female connector 900 is cancelled.

In Embodiments 1 and 2 above, the hood 20 is provided on the base 15 that connects the base end portion 13 of the male luer 10 and the levers 30. However, the method for connecting the hood 20 to the base end portion 13 is not limited to this. For example, the hood 20 may also be coupled to the male luer 10 via a member that is different from the base 15, which holds the levers 30. This configuration can make it possible to facilitate the pivotal movement of the levers 30 while securely coupling the hood 20 to the male luer 10.

The above-described connector main bodies 3, 3', 3", and 203 include the hood 20 that has the circular opening 21 at the leading end. However, in the present invention, the hood 20 can be omitted. For example, instead of the hood 20, the connector main body of the present invention may include a circular arc-shaped member having substantially the same radius as the outer circumferential surface of the female connector 900 such that the circular arc-shaped member is coaxial with the male luer 10 and does not collide with the levers 30. The circular arc-shaped member is held at the same height as or above the locking claws 32 so as to position the female connector 900 in the horizontal direction (in particular, direction of the minor axis 15b). Alternatively, the leading end of the locking claw 32 of each lever 30 may be provided with a circular arc shape having substantially the same radius as the outer circumferential surface of the female connector 900 and being coaxial with the male luer 10. It is possible to position the female connector 900 in the horizontal direction using those circular arc shapes. In this case, the above-described circular arc-shaped member can be omitted.

The number of levers 30 is not limited to two. For example, the male connector 2 may include only one lever 30. If the number of locking claws 32 is two or more, all of the locking claws 32 need to be simultaneously engaged with or disengaged from the female connector 900, and therefore, there is a possibility that the operations for connecting and disconnecting the male connector 2 or 202 to and from the female connector 900 may become complicated. If the number of levers 30 is only one, there is a possibility that the ease of the connecting and disconnecting operations may be improved.

In Embodiments 1 and 2 above, the locking claws 32 are engaged with the annular projection 923 of the female connector 900. However, the portion of the female connector 900 with which the locking claws 32 are engaged may be changed as appropriate in accordance with the configuration of the female connector 900. The shape and position of the locking claws 32 can be changed in accordance with the portions thereof that are to be engaged with the female connector 900.

The shape of the male luer 10 can be changed as desired. The number of lateral holes 12 that are in communication with the flow channel 11 is not necessarily required to be two, and may be one, or three or more. A configuration may also be adopted in which the lateral holes 12 are omitted, and the flow channel 11 is open into the leading end 10a of the male luer 10.

The configuration of the female connector to which the male connector assembly 1 is connected can be changed as desired. For example, the female connector may be a rubber stopper that seals an opening of a vial. A through hole like the slit 911 of the septum 910 is not formed in the rubber stopper in advance. Therefore, in this case, the male luer may be provided with a sharp leading end so as to be able to puncture the rubber stopper. Furthermore, in order to suppress fluctuations in air pressure within the vial when a liquid is flowing out of and into the vial, a liquid flow channel and a gas flow channel that are independent of each other may also be formed in the male luer. The levers (in particular, the locking claws 32) can be changed as appropriate so as to be engageable with a flange that surrounds the opening of the vial.

The configuration of the shield 6 can also be changed as desired. For example, the outer circumferential wall 65 may also have a bellows-like shape in which two tapered portions that are tapered in opposite directions are connected to each other. A configuration may also be adopted in which a slit similar to the slit 911 of the septum 910 is provided in an upper surface of the head portion 61, and, in a state in which the male connector is not connected to a female connector, the upward opening of the through hole 62 is closed in a liquid-tight manner. The method for fixing the shield 6 to the base 15 is not limited to the method of locking the fixing claws 69a onto the base 15, and any methods such as adhesion, welding, fitting, and the like can be used.

In the present invention, the shield 6 may be omitted.

Also, the configurations of the lock rings 8 and 208 can be changed as desired.

In Embodiment 1 above, the first movement prevention mechanism, which prevents the lock ring 8 at the highest position from moving toward the lowest position, and the second movement prevention mechanism, which prevents the lock ring 8 at the lowest position from moving toward the highest position, are respectively constituted by the engagement projections 355 and the engagement projections 37, and both of them are located close to or abut against the lock ring 8 in the vertical direction. However, the configurations of the first and second movement prevention mechanisms are not limited to this. For example, movement of the lock ring 8 may be prevented by frictional force between the lock ring 8 and the operating portions 35, or movement of the lock ring 8 may be prevented by providing recesses to which the lock ring 8 can be fitted in the operating portions 35.

Alternatively, either or both of the first movement prevention mechanism and the second movement prevention mechanism, which prevent movement of the lock ring 8, may be omitted.

Similarly, in Embodiment 2, the configuration of the first movement prevention mechanism, which prevents the lock ring 208 at the highest position from moving toward the lowest position, may be changed as appropriate, or the first movement prevention mechanism may be omitted.

The structure with which the lock ring 8 or 208 is engaged with the operating portions 35 in the X-axis direction is not limited to the engagement structure shown in Embodiments 1 and 2, which utilizes the claws 84 and the sliding ribs 354. Any engagement structure other than this can also be employed. In this case, either or both of the claws 84 and the sliding ribs 354 can be omitted. Alternatively, the engagement structure with which the lock ring 8 is engaged with the operating portions 35 in the X-axis direction may be omitted.

In Embodiment 1, a configuration may also be adopted in which, even when the locking claws 32 are not correctly engaged with the female connector 900, the lock ring 8 can be moved from the highest position to the lowest position without colliding with the inner surfaces 352 of the operating portions 35.

In Embodiment 2, the number of rods 290 is not limited to four, and may be more than or less than four. For example, two rods 290 may be disposed at symmetrical positions with respect to the male luer 10. The number and the positions of the cut-outs 215n provided in the base 15 may be changed in accordance with the rods 290. Moreover, not all of the four rods 290 necessarily include the inclined surfaces 292. For example, only two rods 290, of the four rods 290, that are disposed at symmetrical positions with respect to the male luer 10 may be provided with the inclined surfaces 292. It is also possible that the projections 291 are omitted, and the inclined surfaces 292 are provided at the upper surfaces of the rods 290. The base 15 may be provided with, instead of the cut-outs 215n, through holes into which the rods 290 are inserted. In this case, a connector main body having a substantially elliptical outline when viewed from above can be used.

The tube 190 may also be connected directly to the tubular portion 17 of the male connector 2. For example, the tube 190 can be inserted into the tubular portion 17 and fixed through adhesion or the like. In this case, the screw lock-type connector 100 is no longer necessary.

INDUSTRIAL APPLICABILITY

While there is no particular limitation on the field of use of the present invention, the present invention can be extensively used in the field of medicine as a connecting device for forming a circuit (line) in order to convey various liquids such as a medicinal solution, an infusion solution, and blood. Furthermore, the present invention can also be used in various fields in which liquids are handled, such as the field of food other than medicine.

LIST OF REFERENCE NUMERALS

1 Male connector assembly
2, 202 Lever lock-type male connector
3, 3', 3", 203 Connector main body
3a Central axis
6 Shield
8, 208 Lock ring (lever pivotal movement prevention mechanism; rotation prevention mechanism)
10 Male luer
11 Flow channel of male luer
12 Lateral hole (opening that is in communication with flow channel)
13 Base end portion of male luer
15 Base
15a Major axis
15b Minor axis
17 Tubular portion
17a Female tapered surface
18 Male thread
20 Hood
20a Leading end of hood
23 Cut-out
30 Lever
31 Locking portion
32 Locking claw
35 Operating portion
351 Outer surface of operating portion
352 Inner surface of operating portion
353 Side surface of operating portion
354 Sliding rib
354b Pressure contact portion (first movement prevention mechanism)
355 Locking projection (first locking projection; first movement prevention mechanism)
37 Locking projection (second locking projection; second movement prevention mechanism)
39 Lever base portion
81 Opening of lock ring
84 Claw of lock ring
84a Sliding surface of claw of lock ring
100 Screw lock-type connector
110 Luer main body
112a Male tapered surface
120 Lock nut
128 Female thread
290 Rod
292 Inclined surface (second movement prevention mechanism)
900 Female connector

The invention claimed is:

1. A medical lever lock-type male connector comprising a connector main body and a lock ring,
wherein the connector main body includes a male member and a lever that is connected to a base end portion of the male member via a base, and the male member includes an elongated main body that extends along a central axis of the connector main body and a liquid flow channel in the elongated main body, the liquid flow channel extending along the central axis,
the lever includes a locking portion that is disposed on the same side as the male member relative to the base such that the locking portion opposes the male member in a first direction, an operating portion that is disposed on the opposite side to the male member relative to the base, and a locking claw that protrudes toward the male member from a surface of the locking portion that is located on a side facing the male member,
the lock ring is disposed opposing an inner surface of the operating portion in the first direction,
the lock ring includes a pair of claws that oppose each other in a second direction that is perpendicular to the first direction and the central axis of the connector main body,
the lock ring is movable along the central axis of the connector main body between a first position at which the lock ring is located close to the base and a second position at which the lock ring is located away from the base, and the pair of claws hold the operating portion that is disposed therebetween such that the lock ring is not rotatable about the central axis in movement of the lock ring between the first position and the second position,
when the lock ring is at the first position, the lock ring is spaced apart from the inner surface of the operating portion in the first direction, whereby the lever is elastically pivotable such that the locking claw moves away from the male member, and
when the lock ring is at the second position, the lock ring abuts against the inner surface of the operating portion in the first direction, whereby the lock ring restricts the lever from pivoting such that the locking claw moves away from the male member.

2. The lever lock-type male connector according to claim 1, wherein the lock ring is engageable with the operating portion in the first direction.

3. The lever lock-type male connector according to claim 1, wherein a sliding rib protrudes from a side surface of the operating portion,
the sliding rib extends along a moving direction of the lock ring, and
the lock ring includes a claw that is engageable with the sliding rib.

4. The lever lock-type male connector according to claim 3, wherein the claw of the lock ring includes a sliding surface that opposes an outer surface of the sliding rib in the first direction, and
when the lock ring is at the first position, the sliding surface abuts against the outer surface of the sliding rib in the first direction.

5. The lever lock-type male connector according to claim 1, wherein, in a state in which the lock ring is at the first position, if a female connector is moved toward the base along a longitudinal direction of the male member, the locking claw collides with the female connector, and the lever pivots such that the locking claw moves away from the male member, and if the female connector is moved further toward the base, the locking claw engages with the female connector, and the lever elastically recovers, and
in a state in which the lever has pivoted and the locking claw is not engaged with the female connector, the lock ring at the first position cannot be moved to the second position.

6. The lever lock-type male connector according to claim 1, wherein, in a state in which the lock ring is at the first position, if a female connector is moved toward the base along a longitudinal direction of the male member, the locking claw collides with the female connector, and the lever pivots such that the locking claw moves away from the male member, and if the female connector is moved further toward the base, the locking claw engages with the female connector, and the lever elastically recovers, and
in a state in which the lever has pivoted and the locking claw is not engaged with the female connector, if the lock ring at the first position is moved toward the second position, the lock ring collides with the operating portion prior to reaching the second position, thereby causing the locking claw to be engaged with the female connector.

7. The lever lock-type male connector according to claim 1, wherein, in a state in which the lock ring is at the first position, if a female connector is moved toward the base along a longitudinal direction of the male member, the lock ring is moved toward the second position by the female connector, and
at the same time as the locking claw engages with the female connector, the lock ring reaches the second position.

8. The lever lock-type male connector according to claim 7, wherein, in a state in which the locking claw is engaged with the female connector, the lock ring can be moved from the second position to the first position.

9. The lever lock-type male connector according to claim 1, wherein the lock ring includes a rod that extends beyond the base toward the male member, and
the rod is configured such that at least a portion thereof that is located on a male member side relative to the base collides with a female connector.

10. The lever lock-type male connector according to claim 9, wherein an inclined surface is provided at an upper surface of the at least a portion of the rod, the inclined surface being inclined such that the distance to the base decreases as the distance to the male member decreases.

11. The lever lock-type male connector according to claim 9, wherein, in a state in which the lock ring is at the second position and the locking claw is engaged with the female connector, if a force acting toward the first position is applied to the lock ring, the rod deforms such that the at least a portion of the rod moves away from the male member.

12. The lever lock-type male connector according to claim 1, further comprising a first movement prevention mechanism that prevents the lock ring at the first position from moving toward the second position or a second movement prevention mechanism that prevents the lock ring at the second position from moving toward the first position.

13. The lever lock-type male connector according to claim 1,
wherein an opening that is in communication with the liquid flow channel is provided in an outer circumferential surface of the male member,
the male connector further includes a shield that closes the opening, and
when the male member is inserted into a female connector, the shield is compressively deformed in a longitudinal direction of the male member, and the opening is exposed.

14. The lever lock-type male connector according to claim 1,
wherein the connector main body includes two of the levers, and
the two levers are arranged at symmetrical positions with respect to a central axis passing through the male member.

15. A male connector assembly comprising the lever lock-type male connector according to claim 1 and a screw lock-type connector,
wherein the connector main body further includes a tubular portion on the opposite side to the male member relative to the base, the tubular portion being in communication with the male member,
a female tapered surface is formed on an inner circumferential surface of the tubular portion, the female tapered surface having an internal diameter that increases as the distance to a leading end of the tubular portion decreases,
a male thread is formed on an outer circumferential surface of the tubular portion,
the screw lock-type connector includes a screw lock connector main body provided with a male tapered surface that can be fitted to the female tapered surface of the tubular portion and a lock nut that is rotatable around the screw lock connector main body, and
the lock nut is provided with a female thread that can be screwed onto the male thread of the tubular portion.

16. The male connector assembly according to claim 15, wherein, in a state in which the male tapered surface of the screw lock connector main body has been fitted to the female tapered surface of the tubular portion and the female thread of the lock nut has been screwed onto the male thread of the tubular portion, if the lock ring is moved to the second position, the lock nut is disposed within the lock ring.

* * * * *